US007531625B2

(12) United States Patent
Olson et al.

(10) Patent No.: US 7,531,625 B2
(45) Date of Patent: May 12, 2009

(54) β NETRIN AND USES THEREOF

(75) Inventors: Pamela Olson, Chestnut Hill, MA (US); Dale Hunter, Hingham, MA (US); William Brunken, Hingham, MA (US); Manuel Koch, Cologne (DE); Robert Burgeson, Palm Springs, CA (US)

(73) Assignee: The General Hospital Corporation, Boston, MA (US)

( * ) Notice: Subject to any disclaimer, the term of this patent is extended or adjusted under 35 U.S.C. 154(b) by 597 days.

(21) Appl. No.: 10/831,979

(22) Filed: Apr. 26, 2004

(65) Prior Publication Data
US 2004/0248178 A1 Dec. 9, 2004

Related U.S. Application Data

(62) Division of application No. 09/795,671, filed on Feb. 28, 2001, now Pat. No. 7,390,634.

(60) Provisional application No. 60/229,893, filed on Sep. 1, 2000, provisional application No. 60/185,811, filed on Feb. 29, 2000.

(51) Int. Cl.
C07K 14/00 (2006.01)
(52) U.S. Cl. .................................................... 530/350
(58) Field of Classification Search ................. None
See application file for complete search history.

(56) References Cited

U.S. PATENT DOCUMENTS

| 5,565,331 | A | 10/1996 | Tessier-Lavigne et al. |
| 5,610,031 | A | 3/1997 | Burgeson et al. |
| 5,824,775 | A | 10/1998 | Swimmer et al. |
| 6,017,714 | A | 1/2000 | Tessier-Lavigne et al. |
| 6,096,866 | A | 8/2000 | Tessier-Lavigne et al. |
| 6,309,638 | B1 | 10/2001 | Tessier-Lavigne et al. |
| 6,670,451 | B2 | 12/2003 | Tessier-Lavigne et al. |
| 2003/0017157 | A1 | 1/2003 | St. Croix et al. |

FOREIGN PATENT DOCUMENTS

| WO | WO 95/13367 | 5/1995 |
| WO | WO 97/40064 | 10/1997 |
| WO | 00/06698 | 2/2000 |
| WO | WO 00/06698 | 2/2000 |
| WO | WO 00/53742 | 9/2000 |
| WO | WO 02/10217 | 2/2002 |

OTHER PUBLICATIONS

Lederman et al (Molecular Immunology 28:1171-1181).*
Examination Report from the European Patent Office dated Dec. 16, 2005, issued for application No. 01 914 569.7.
European Search Report for application No. 0194569.7 with the European Patent Office.
"XP-002300330," *EMBL Nucleotide Sequence Database*, retrieved from EBI accession No. EBML:HSM802277, Database accession No. AL137540 (2000).
Yin et al., "Identification and expression of mouse netrin-4," *Mechanisms of Development*, vol. 96, No. 1, pp. 115-119 (2000).
Banyai et al., "The NTR Module: Domains of Netrins, Secreted Frizzled Related Proteins, and Type I Procollagen C-Proteinase Enhancer Protein are Homologous with Tissue Inhibitors of Metalloproteases," *Protein Science*, vol. 8, pp. 1636-1642 (1999).
Kim and Wadsworth, "Positioning of Longitudinal Nerves in C. elegans by Nidogen", 2000, *Science* 288:150.
Koch et al., "A Novel Member of the Netrin Family, β-Netrin, Shares Homology . . . ", *J. Cell Biology*, vol. 151, No. 2: 221-234, 2000.
Lauderdale et al., "Axon Tracts Correlate with Netrin-1a Expression in the Zebrafish Embryo", 1997 *Mo. Cell Neurosci.* 9:293.
Lim et al., "Netrin UNC-6 and the Regulation of Branching and Extension of Motoneuron . . . ", 1999, *J Neuroscience* 19:7048.
MacLennan et al., "Immunohistochemical Localization of Netrin-1 in the Embryonic . . . ", 1997, *J. Neurosci.* 17:5466.
Meyerhardt et al., "Netrin-1: Interaction with Deleted in Colorectal Cancer (DCC) and . . . ", 1999, *Cell Growth Differ.* 10:35.
Puschel, "Divergent properties of mouse netrins", 1999, *Mech. Dev.* 83:65.
Serafini et al., "The Netrins Define a Family of Axon Outgrowth-Promoting . . . ", 1994, *Cell* 78:409.
Serafini et al., "Netrin-1 Is Required for Commissural Axon Guidance in the Developing . . . ", 1996, *Cell* 87:1001.
Skarnes et al., "Capturing genes encoding membrane and secreted proteins important for mouse development", 1995, *Proc. Nat. Acad. Sci. USA* 92:6592.
Soker et al., "Neuropilin-1 Is Expressed by Endothelial and Tumor cells as an Isoform-Specific Receptor . . . ", 1998, *Cell* 92:735.
Strahle et al., "Expression and Regulation of a Netrin Homologue in the Zebrafish Embryo", 1997, *Mech. Dev.* 62:147.
Van Raay et al., "The NTN2L Gene Encoding a Novel Human Netrin Maps to the . . . ", 1997, *Genomics* 41:279.
Vuolteenaho et al. "Structure of the Human Laminin B1 Chain Gene", (1990) *J. Biol. Chem.* 265:15611.
Wadsworth et al., "Neuroglia and Pioneer Neurons Express UNC-6 to Provide Global and . . . ", 1996, *Neuron* 16:35.
Wang et al., "Netrin-3, a Mouse Homolog of Human NTN2L, Is Highly Expressed in Sensory Ganglia and . . . ", 1999, *J. Neurosci* 19:4938.
Winberg et al., "Genetic Analysis of the Mechanisms Controlling Target Selection: Complementary and . . . ", (1998) *Cell* 93:581.
Zhang et al. (EST, Genebank Accession No. AF 119916).
International Search Report for PCT/US01/06413.
Alcantara et al., "Netrin 1 acts as an attractive or as a . . . ", 2000, *Development* 127:1359.
Bashaw and Goodman, "Chimeric Axon Guidance Receptors: The Cytoplasmic . . . ", 1999, *Cell* 97:917.
Colamarino and Tessier Lavigne, "The Axonal Chemoattractant Netrin-1 Is Also . . . ", (1995) *Cell* 81:621.
de la Terre et al., "Turning of Retinal Growth Cones in a Netrin-1 Gradient . . . ", 1997, *Neuron* 19:1211.

(Continued)

*Primary Examiner*—Christopher H Yaen
(74) *Attorney, Agent, or Firm*—Fish & Richardson P.C.

(57) ABSTRACT

β-netrin nucleic acid molecules and polypeptides are provided. Methods of using the β-netrin nucleic acid molecules and polypeptides are also provided.

9 Claims, 11 Drawing Sheets

OTHER PUBLICATIONS

Deiner et al., "Netrin-1 and DCC Mediate Axon Guidance Locally at the . . . ", 1997, *Neuron* 19:575.

Deiner and Sretavan, "Altered Midline Axon Pathways and Ectopic Neurons in the . . . ", 1999, *J Neuroscience* 19:9900.

Engel, "Laminins and Other Strange Proteins", (1992) *Biochemistry* 32:10643.

GenBank Accession No. AAA26362, Jun. 29, 2000.

GenBank Accession No. T46383, Feb. 4, 2000.

Hedgecock et al. "The unc-5, unc-6, and unc-40 Genes Guide Circumferential Migrations . . . ", 1990, *Neuron* 4:61.

Keino-Masu, "Deleted in Colorectal Cancer (DCC) Encodes a Netrin Receptor", 1996, *Cell* 87:175-185.

Kennedy et al., "Netrins Are Diffusible Chemotropic Factors for Commissural . . . ", 1994, *Cell* 78:425.

Kim et al., "SDQR migrations in *Caenorhabditis elegans* are controlled by multiple . . . ", 1999, *Development* 126:3881.

\* cited by examiner

Amino acid sequence of human and mouse β-netrin domain VI

```
                                                                    50
h MGSCARLLLL WGCTVVAAGL SGVAGVSSRC EKACNPRMGN LALGRKLWAD
m ---------- ---SA----- N----AN--- ---------- -------R--
                                                                   100
h TTCGQNATEL YCFYSENKDL TCRQPKCDKC NAAYPHLAHL PSAMADSSFR
m -M-------- F------A-- ---------- ---HS----P ----------
                                                                   150
h FPRTWWQSAE DVHREKIQLD LEAEFYFTHL IVMFKSPRPA AMVLDRSQDF
m ---------- ---------- ---------- --MV------ ----------
                                                                   200
h GKTWKPYKYF ATNCSATFGL EDDVVKKGAI CTSKYSSPFP CTGGEVIFKA
m ---------- ---------- ---------- ---R--N--- --------R-
                                                                   250
h LSPPHDTENP YSAKVQEQLK ITNLRVQLLK RQSCPCQRND LNEEPQHFTH
m ----Y-I--- ---------- ------R--- -------I-- --AK-H---H
              261
h YAIYDFIVKG S
m --V------- -
``` domain V

```
                                                                   300
h            CFCNGHADQ CIPVHGFRPV KAPGTFHMVH GKCMCKHNTA
m            ---------- -L--E----I ----A--V-- -R--------
                                                                   350
h GSHCQHCAPL YNDRPWEAAD GKTGAPNECR ACKCNGHADT CHFDVNVWEA
m ---------- ---------- -R-------- T--------- ----------
                                                                   400
h SGNRSGGVCD DCQHNTEGQY CQRCKPGFYR DLRRPFSAPD ACKPCSCHPV
m --------N N--------H ---------- ---------- ---A------
                                                                   450
h GSAVLPANSV TFCDPSNGDC PCKPGVAGRR CDRCMVGYWG FGDYGCRPCD
m ---I--FS-- ---------- --------PH ---------- ----------
              462
h CAGSCDPITG DC
m -------L-- --
```

C domain

```
                                                                   500
h            ISSHTDID WCHEVPDFRP VHNKSEPAWE WEDAQGFSAL
m            ---NA-V- -Y----T-HS M-------S-- ---E------
                                                                   550
h LHSGKCECKE QTLGNAKAFC GMKYSYVLKI KILSAHDKGT HVEVNVKIKK
m R--------- -V---P---- ---------- ---------S -A--------
                                                                   600
h VLKSTKLKIF RGKRTLYPES WTDRGCTCPI LNPGLEYLVA GHEDIRTGKL
m ---------L ---------- --N------- ---------- ----V-----
              628
h IVNMKSFVQH WKPSLGRKVM DILKRECK
m ---------- ---A---R-- H----D-V
```

FIG. 3

```
tggtctgtagctaggaaactcttgaaataagaaacagcaccattggaaagaggcttaga
ttcaagcttgaggaaattcccgaggtgatattcctaaggggcagccgaatggcagaggc
ctggtaaaaaccagaatgggagatgatttcagtgggaacactttatccgaccttcttca
cacaaggttgtagccacagaagacggacaagcaatgcaatcctgatctaggaacccagg
ttcttgagccaatgagctcattggatgtgtacatatttatgatctaagtttggtgatg
atatccctccccccgacactatctctttgtacaattctttgtgggttgcaatatgca
cacattcattcaagagggcaaaagaggtgatgtttcttgttccttgaagaaagaatat
cagataccatgataataagtctcttttccaaagtcccccattctgttggtgatatagaat
aagtgtcacataaagtatactggccttattcaggaagcagatatatattttctattag
gataataagcttgttttaaatatcctgacttttttttatcttttaccttttgtgtgtgt
gtgtgtgtgtgtgtgtgtgagagagagagagagagagagagagag ----
length of agaga--is not exact but within 10 to 20 bp------- agagagagagagagtaggaaccccagatcacctctccaccttcctcagtgctaagcac
ggttLcaacggtcagcatcttcttggtaaaacacgggttctgagggtgaagcccaggcc
ctcattgcttcgaaggctagcaccttttagacagagctatctctcccaactatttttt
aatttagaaatgtgaccctgaggatctttttttttaaacttaatactgtttgaatgt
ttcctatatgtattcaagcactaaatcttaacggcctgtaagaaatcaatacatacaaa
aagtttattctgactccaagctatgttagccagtgttacaaagctgcaggtgtgttctt
aggctacgtaagtacaagtcctagactcaaaggacactgtaagttttatttatttat
tctaattgatcacacttacagttgacttatatgtgtactgtgcaattggagtatatctg
aaaagggatgaagaagagttttccaaagcacttggagaaggtgcttaaatagagcaatc
aaacctgggttcaacgtctcagagacctaacaggtggtccgtgctttcatcccagcact
cagaagactaaggcaagaaacactaagagtttggggtcagcctgggctacatcaatagc
aggtttcaggccaggccaacctgggctatttaatgagaccttgtctcaactcttgcatg
cacgcgcgcgcgcacacacacacacatacattaaagagagaactggtatttatctgt
atagctgcaaatgtctataaagaggtagtgcacagttaaataaaaccagtgctgaaatc
gagtgatgcttttgattcttttgtttattgggatgctcagaagaaaacctgtgtgacca
atgggcagagttttcacggtgaatgaagggctccgggtagggtgagagttggggcccag
ggtcccatctgattctgaacatctttcggtcattagactttgtgctgggttttagaga
tctcttcagagctttgtggtgctttgtctctgtgctaacaggccttgggctgctggaag
attttttgctttgaaggaggatggatactgctgccatgttttgtctttacgtctgctg
tttcgccatcctcttgcttctaggctgccacagtttatccttcttctgagcaggatcc
tgttccgcttgggcttgttctcctcatacactgagccccagaaaagcaccctgcacagt
cacactgaaattggaggagaaacttaaatgtggcccagaggcgcttgggaatgaggtct
ttggtgtatggacctttagcctttctgatgtagatatatattagcggtcctgtcaacat
ccttccaagtcgtcaggaatgttctacattaaatttgtggatttgtggctttggaaaac
ctgctattgaaatcctgcaatttatccaaccctcctgtaatccatgacacctggaaag
```

FIG. 6A

```
ttctgagtcagttcttgacatttcataacacgaagacataatgagcaatgtccccacc
cggaacacatttcctcacattggccaactctcttgggtcctttttcaaaatgaaaat
ataattgtaagaatgtatactagatatgcactttaaaaaaaaaa
--- about 100bp missing ---
cttcttgcctctaccaatgactaaggttacaggcggaaaccaccacattgcgcccagac
aacatttattcgaatgctcattaccgtttctctgagctagtccacacttaaagtattgc
tgtggagagcccacattcctctagaatcctgggaatcgttcttatttcgccgctttatt
ctcagtctctattcttagcatataacaatagttttgagataactgtcaaaacatttatt
gcatgtctgacaagtgttttcagttaagaataacgagcaatgtaagaaaaaaacataa
ttgtgtcttgcatagtctaagtgtctagctgccatttaaggatcttgctgtttattaaa
ggagcgacaaaccagttacaaagcgatcaggggagtacccagcaaatgcttctgaaatt
cataatcaggcatggattagccctgcctcaacttaatatattgtctcagagattaatag
taaatactgtctttctcttctttttcttggcctgtaggctagtgtttaggctgggagc
tttagcctgttacgatccctgtcgttcattaataaaaagaacagagaagcatttag
caactgcatcagaagcatcacctgtgagagccaaaggaggctccagcgtggccagtatt
tgaaagctcagagtttgttttctaaagctggtgacggttctcatgtcgcctgccacttc
cagtactggccaaaataataatttaacgccttcccagtggattatgctaacctcaact
cagttcctttagagagatagaaacctatatgtctccagctcggtcattataaataatat
ctacgtgtgccccaaagctctaattggccccatctgtatttctgacaatttataataa
ctgaatggtatctgcaaagcagttaactttctggaaaatactcaaagacacacactgaa
tgctgcaatacagaattgccttcgactcaacgtttgccaatttctttgcatgtgtaagc
agaactatattttcagagaagttacagaagtcccaggctgaagtgctatttaatctcct
ttcataaacaccagccctgagctacaattagctgcttgtggttgctgctaaattgctcc
ccataagatatttcataactttatggttcccctgctcaccatactatgaagaatgtgtg
aatgcacctaggacccaggcattcttatgtcgatgttccagactgagatgttcttaaac
agttgattccctgatcatggatcctggtctttcaggccgtgtgagaacatctttttacac
caaaacgggtacaccttcgactcctttgggctgcaccccaaaaaggtagcagagact
taaaggaccttagcatttggtgcgcgttcactggcagtaccctaggcagaattgggggt
ctgggggtggtcctaacccagaccgtgggactcacagagaatgggtgctgtggagtggt
gttgggggagggggaaggcttgttttgctgggtgatttttgaaagtagtcgctcgcct
gtttcgcgggttttaagccccttggcatgccctgacctgatccggagggagtcaact
gctctcaggaatgttcctggagaaaggtgggagactgtttcccaggcgaggcccttggg
tgctggagggcaccgcgaggtcaggcagggagatgcgcgcagcgggggctgcagacac
cccctcccctgggcggcggcggcggcgacaatgaccggacccgcgcgtctgcaccacc
cggctgtcaagcgcggggggcgggcgggaggaagggtggaggtgcgaggggaggagga
gggctggcaccggagcgccgcggtgtcggtgcaatAAAAAtgcatcccatggaactgcc
catggAGAAGGacgggaccgagcctcggcggccacagaaggtgggaaaaGCGGAGGAGG
ACAGCCGGGAGGCGGCGGCGGCCGGGAAGTGAAAGGTCTCGCAAAGTTCAGCGTCGGCT
GCGGGCGCCGAGCCCTGGGCGAGCGGCGCACCCGCCCTCAGGGCCGCTCAGCCGGCAGC
GGCCAGGCCGGCTATGATCCCGGGGCTCCCGCCGCTGCTGAGCTGCCCGGGCCCCGCCA
GGCCGGTGCGCGACGGTCACCCCGCCGCCTGGCGCGGCCCCGGCCCGCGGCTCTGTGCC
CACGGTGCCCACTGAGCGAGCCTGGCGCTCCGGGAGGAGGAAGAACCACAGAGCCCCCG
GTGCTCCCGAGGACCACTGCCGCTTCATCCCACCCGCTCCCGCAGCTGCCCGGCCATGG
GGAGCTGCGCACGGCTGCTGCTGCTCTGGGCTGCTCCGCGGTGGCCGCAG---
2.5kb intron ---
GCTTGAATGGAGTAGCCGGAGCGAACTCCCGCTGTGAGAAGGCATGCAACCCTCGCATG
GGAAACTTGGCTTTGGGAAGAAAGCTCCGGGCAGACACTATGTGTGGCCAGAACGCCAC
CGAACTCTTCTGCTTCTACAGTGAGAATGCTGACCTCACTTGCCGGCAGCCCAAGTGTG
```

FIG. 6B

ATAAATGCAACGCTGCCCATTCTCACCTAGCTCACCCACCCTCTGCCATGGCAGACTCA
TCCTTCAGGTTTCCCCGGACATGGTGGCAGTCTGCAGAGGATGTGCACAGGGAAAAGAT
TCAGCTAGACCTGGAAGCAGAATTCTACTTCACTCACCTAATTATGGTGTTCAAGTCTC
CCAGGCCTGCAGCCATGGTGCTGGACCGGTCCCAGGACTTTGGGAAGACCTGGAAGCCT
TACAAGTACTTTGCAACAAACTGCTCGGCTACTTTTGGCCTGGAAGATGATGTTGTCAA
GAAGGGAGCTATTTGCACGTCTAGATACTCAAATCCTTTCCCGTGCACCGGAGGAGAG
---intron    -- 4-5 kb---GTTATTTTC......

FIG. 6C

β NETRIN AND USES THEREOF

CROSS-REFERENCE TO RELATED APPLICATIONS

This application is a divisional of U.S. patent application Ser. No. 09/795,671, filed on Feb. 28, 2001, which claims the benefit of Provisional Patent Application Ser. No. 60/229,893, filed on Sep. 1, 2000, and Provisional Patent Application Ser. No. 60/185,811, filed on Feb. 29, 2000. The disclosures of these prior applications are incorporated herein by reference.

BACKGROUND OF THE INVENTION

The extracellular matrix provides a complex and instructive substrate for cells in multicellular organisms. The matrix contains a multitude of proteins, some of which are structural, whereas others can further provide regulatory signals to modulate cell growth, differentiation, and migration.

In the developing nervous system, axons project considerable distances along pathways to reach their targets. Axon growth and guidance depends partially on the recognition of cell surface and extracellular matrix cues along these pathways. These compounds can play a role in when neurons grow, where neurons grow and when they should stop growing. In the cardiovascular system, the extracellular matrix can also provide signals for the development of smooth muscle for blood vessels, e.g., for angiogenesis.

SUMMARY OF THE INVENTION

The invention is based, in part, on the discovery of a nucleic acid and corresponding protein molecule, referred to herein as β-netrin molecules. The β-netrin molecules of the present invention are useful in neurite outgrowth, guidance and/or stability. In addition, the β-netrin molecules are useful in treating ovarian, renal, neurological and cardiovascular disorders as well as in modulating angiogenesis and cell proliferation.

Accordingly, in one aspect, the invention features an isolated nucleic acid molecule (e.g., cDNAs) comprising a nucleotide sequence encoding a β-netrin protein or a biologically active portion thereof, as well as, nucleic acid fragments, e.g., a 50 nucleotide, 100 nucleotide, 200 nucleotide, 300 nucleotide, or longer, fragment suitable as primer or hybridization probe for the detection of β-netrin-encoding nucleic acid (e.g., mRNA). In particularly preferred embodiments, the isolated nucleic acid molecule includes the nucleotide sequence of SEQ ID NO:1 or SEQ ID NO:4, or a complement of these nucleotide sequences. In another preferred embodiment, the isolated nucleic acid molecule includes the coding region of SEQ ID NO:1 (about nucleotides 452 to 2333 of SEQ ID NO:1, (SEQ ID NO:15)) or SEQ ID NO:4. In other particularly preferred embodiments, the isolated nucleic acid molecule of the invention includes a nucleotide sequence which hybridizes, preferably under stringent conditions, to or has at least about 60-65%, preferably at least about 70-75%, more preferably at least about 80-85%, and even more preferably at least about 90-95%, 96%, 97%, 98% or 99% sequence identity to the nucleotide sequence shown in SEQ ID NO:1, SEQ ID NO:4, or portions thereof. In other preferred embodiments, the isolated nucleic acid molecule encodes the amino acid sequence of SEQ ID NO:2 or SEQ ID NO:5. A preferred β-netrin nucleic acid encodes a protein which also preferably possesses at least one of the β-netrin activities described herein.

In another embodiment, the isolated nucleic acid molecule encodes a protein or portion thereof wherein the protein or portion thereof includes an amino acid sequence which is sufficiently homologous to an amino acid sequence of SEQ ID NO:2 or SEQ ID NO:5, e.g., sufficiently homologous to an amino acid sequence of SEQ ID NO:2 or SEQ ID NO: 5 such that the protein or portion thereof maintains a β-netrin biological activity. Preferably, the protein or portion thereof encoded by the nucleic acid molecule maintains the ability to play a role in neurite outgrowth and/or angiogenesis. In one embodiment, the protein encoded by the nucleic acid molecule has at least about 60-70%, preferably at least about 80-85%, and more preferably at least about 86, 88, 90%, and most preferably at least about 90-95%, 96%, 97%, 98% or 99% sequence identity to the amino acid sequence of SEQ ID NO:2 or SEQ ID NO:5 (e.g., the entire amino acid sequence of SEQ ID NO:2 or SEQ ID NO:5). In another preferred embodiment, the protein is a full-length protein which is substantially homologous to the entire amino acid sequence of SEQ ID NO:2 (encoded by the open reading frame shown in SEQ ID NO:3) or SEQ ID NO:5. In another embodiment, the protein is a human protein, which is substantially homologous to the amino acid sequence of SEQ ID NO:2, or a portion thereof. In another preferred embodiment, the protein is a murine protein, which is substantially homologous to the amino acid sequence of SEQ ID NO:5, or a portion thereof.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A β-netrin nucleic acid fragment can include a sequence corresponding to a domain, region, or functional site described herein. A nucleic acid fragment can also include one or more domain, region, or functional site described herein. Thus, for example, the nucleic acid fragment can include, e.g., a VI or V domain. In a preferred embodiment the fragment is at least, 50, 100, 200, 300, 400, 500, 600, 700, or 900 base pairs in length.

In a preferred embodiment, the isolated nucleic acid molecule encodes a portion of a β-netrin protein which includes a sequence encoding a laminin βN-terminal (Domain VI) domain. This domain has been identified in a large number of laminins, including the human laminin β1 chain. See Vuolteenaho et al. (1990) *J. Biol. Chem.* 265:15611-15616. In addition, this domain has been identified in several netrins, including netrin-1 and netrin-2. Preferably, a laminin βN-terminal (Domain VI) domain encoded by the nucleic acid molecule has at least about 80% or more sequence identity to the laminin βN-terminal (Domain VI) domain (i.e., about amino acid residues 1 to 261) of SEQ ID NO:2.

In another preferred embodiment, the isolated nucleic acid molecule encodes a portion of a β-netrin protein which includes a sequence encoding a laminin EGF-like domain, e.g., a laminin βEGF-like domain, e.g., a laminin βEGF-like (Domain V) domain. The laminin EGF-like domain includes a conservative pattern of about eight cysteine residues. These cysteine residues likely form disulfide bonds which are important for the structural integrity of the protein. Laminin EGF-like domains are found in a wide variety of laminins (Engel (1992) *Biochemistry* 32:10643-10651) and in various netrins. As used herein, a laminin EGF-like domain refers to an amino acid sequence of about 25 to 50, 30 to 45, 30 to 40, or 35 to 40 amino acids in length. A laminin EGF-like domain further contains at least about 2, 3, 4, 5, 6, 7, 8 conserved cysteine residues. Preferably, a laminin βEGF-like domain encoded by the nucleic acid molecule has at least about 80% or more sequence identity to the laminin βEGF-like domain (i.e., about amino acid residues 262 to 462) of SEQ ID NO:2.

In another preferred embodiment, the isolated nucleic acid molecule encodes a portion of a C-terminal of netrin β protein which includes β-netrin frz domain. Preferably, β-netrin frz domain encoded by the nucleic acid molecule has at least about 80% or more sequence identity to the netrin frz domain (i.e., about amino acid residues 463 to 628) of SEQ ID NO:2. As used herein the term "netrin frz domain" and the term "netrin C domain" are used interchangeably.

In a preferred embodiment, the isolated nucleic acid molecule encodes a polypeptide having two or more of: a laminin N-terminal (Domain VI) domain, an EGF-like domain, and a C-terminal frz domain. In a preferred embodiment, the isolated nucleic acid molecule encodes a polypeptide having a laminin N-terminal (Domain VI) domain and an EGF-like domain. In another preferred embodiment, the isolated nucleic acid molecule encodes a polypeptide having a laminin N-terminal (Domain VI) domain, an EGF-like domain, and a C-terminal frz domain.

In another preferred embodiment, the isolated nucleic acid molecule encodes β-netrin protein or portion thereof which has at least about 55% or more sequence identity to SEQ ID NO:2 or SEQ ID NO:5 and has one or more of the following activities: 1) the ability to modulate (e.g., attract or repel) neurite outgrowth, guidance, e.g., guidance of central nervous system axons and/or peripheral motor neurons, and/or stability, e.g., synapses stability; 2) ability to modulate development of the central nervous system, e.g., development of the spinal cord, development of the optic system (e.g., retina), e.g., development of the olfactory system; 3) ability to modulate development of areas of the brain; 4) ability to modulate angiogenesis, e.g., inhibit angiogenesis in tumors; 5) ability to modulate proliferative disorders, e.g., cancer, e.g., cervical, ovarian or colorectal cancer; 6) the ability to modulate development of the kidney (e.g., morphogenesis of tubules and glomeruli); 7) the ability to modulate the maturation of ovarian follicles; and 8) the ability to modulate muscular development and/or innervation (e.g., musculature of the heart, arterioles, fallopian tubes, and lamina propria), especially smooth muscle.

In another embodiment, the isolated nucleic acid molecule is at least 15 nucleotides in length and hybridizes under stringent conditions to a nucleic acid molecule comprising the nucleotide sequence of SEQ ID NO:1 or SEQ ID NO:4. Preferably, the isolated nucleic acid molecule corresponds to a naturally occurring nucleic acid molecule. More preferably, the isolated nucleic acid encodes naturally occurring β-netrin or a biologically active portion thereof. In another preferred embodiment, the isolated nucleic acid molecule encodes a recombinant β-netrin (rβ netrin). Preferably, the biologically active portion is preferably encoded by a nucleotide sequence greater than 150, 200, 300, 400, 500, 600, 700 or 1000 base pairs in length. Moreover, given the disclosure herein of β-netrin-encoding cDNA sequences (e.g., SEQ ID NO:1, SEQ ID NO:4), antisense nucleic acid molecules (i.e., molecules which are complementary to the coding strand of the β-netrin cDNA sequence) are also provided by the invention. In one embodiment, the isolated nucleic acid encodes for a β-netrin frz domain, a β-netrin laminin β Domain VI, or a β-netrin laminin β Domain V. In another embodiment, the isolated nucleic acid encodes for a β-netrin lacking the frz domain, β-netrin lacking laminin β Domain VI, or β-netrin lacking laminin β Domain V.

In a preferred embodiment, the encoded β-netrin protein differs in amino acid sequence by at least 1 to as many as (but not more than) 2, 3, 5, 10, 20 or 40 residues from a sequence in SEQ ID NO:2, or SEQ ID NO:5. In a preferred embodiment, the differences, however, are such that: the β-netrin encoded protein exhibits a β-netrin biological activity, e.g., the encoded β-netrin protein retains a biological activity of a naturally occurring β-netrin, e.g., the β-netrin protein of SEQ ID NO:2 or SEQ ID NO:5.

In preferred embodiments, the encoded polypeptide includes all or a fragment of an amino acid sequence from SEQ ID NO:2 or SEQ ID NO:5, fused, e.g., in reading frame, to additional amino acid residues, preferably to residues encoded by genomic DNA 5' to the genomic DNA which encodes a sequence from SEQ ID NO:2 or SEQ ID NO:5.

In preferred embodiments the encoded β-netrin protein includes a β-netrin sequence described herein as well as other N-terminal and/or C-terminal amino acid sequence.

In another aspect, the invention features vectors, e.g., recombinant expression vectors, containing the nucleic acid molecules of the invention and host cells into which such vectors have been introduced. In one embodiment, such a host cell is used to produce a β-netrin protein by culturing the host cell in a suitable medium. The β-netrin protein can be then isolated from the medium or the host cell.

In yet another aspect, the invention features a transgenic nonhuman animal, e.g., a rodent (e.g., a mouse), or a cow, goat, pig, rabbit or guinea pig, in which a β-netrin gene has been introduced or altered. In one embodiment, the genome of the nonhuman animal has been altered by introduction of a nucleic acid molecule of the invention encoding β-netrin as a transgene. In another embodiment, an endogenous β-netrin gene within the genome of the nonhuman animal has been altered, e.g., functionally disrupted, by homologous recombination.

In still another aspect, the invention features an isolated β-netrin protein or a portion, e.g., a biologically active portion, thereof. In a preferred embodiment, the isolated β-netrin protein or portion thereof modulates angiogenesis and/or neurite outgrowth. In another preferred embodiment, the isolated β-netrin protein or portion thereof is sufficiently homologous to an amino acid sequence of SEQ ID NO:2 or SEQ ID NO:5 such that the protein or portion thereof maintains one or more β-netrin activity. In a preferred embodiment, the invention features a portion of β-netrin, e.g., a biologically active portion, e.g., a portion which is diffusible.

In one embodiment, the biologically active portion of the β-netrin protein includes a domain or motif, preferably a domain or motif which has a β-netrin activity. The motif can be, e.g., a laminin β N-terminal (Domain VI) domain, an EGF-like domain (e.g., a laminin β EGF-like domain, e.g., a laminin β EGF-like (Domain V) domain), and/or a C-terminal frz domain.

The invention also provides an isolated preparation of a β-netrin protein. In preferred embodiments, the β-netrin protein includes the amino acid sequence of SEQ ID NO:2 or SEQ ID NO:5. In another preferred embodiment, the invention pertains to an isolated full-length protein which is substantially homologous to the entire amino acid sequence of SEQ ID NO:2 (encoded by the open reading frame shown in SEQ ID NO:3) or SEQ ID NO:5. In yet another embodiment, the protein has at least about 60-70%, preferably at least about 80-85%, and more preferably at least about 86, 88, 90%, and most preferably at least about 90-95%96%, 97%, 98% or 99% sequence identity to the entire amino acid sequence of SEQ ID NO:2 or SEQ ID NO:5. In other embodiments, the isolated β-netrin protein includes an amino acid sequence which has at least about 60-70% or more sequence identity to the amino acid sequence of SEQ ID NO:2 or SEQ ID NO:5 and has an one or more of the following activities: 1) the ability to modulate (e.g., attract or repel) neurite outgrowth, guidance, e.g., guidance of central nervous system axons and peripheral motor neurons, and/or stability, e.g., synapses stability; 2) ability to modulate development of the central nervous system, e.g., development of the spinal cord, development of the optic system (e.g., retina), e.g., development of the olfactory system; 3) ability to modulate development of areas of the brain; 4) ability to modulate angiogenesis, e.g., inhibit angiogenesis in tumors; 5) ability to modulate proliferative disorders, e.g., cancer, e.g., cervical, ovarian or colorectal cancer 6) the ability to modulate development of the kidney (e.g., morphogenesis of tubules and glomeruli); 7) the ability to modulate the maturation of ovarian follicles; and 8) the ability to modulate muscular development and/or innervation (e.g., musculature of the heart, arterioles, fallopian tubes, and lamina propria), especially smooth muscle. The ability to modulate neurite outgrowth, guidance and synaptic stability can be by, for example, haptotactic mechanisms or chemotactic mechanisms.

Alternatively, the isolated β-netrin protein can include an amino acid sequence which is encoded by a nucleotide sequence which hybridizes, e.g., hybridizes under stringent conditions, or has at least about 60-65%, preferably at least about 70-75%, more preferably at least about 80-85%, and even more preferably at least about 90-95%96%, 97%, 98% or 99% sequence identity to the nucleotide sequence of SEQ ID NO: 1 or SEQ ID NO:4. It is also preferred that the preferred forms of β-netrin also have one or more of the β-netrin activities described herein.

In a preferred embodiment, the β-netrin protein differs in amino acid sequence at least up to 1 to as many (but not more than) 2, 3, 5, 10, 20, or 40 residues, from a sequence in SEQ ID NO: 2 or SEQ ID NO:5. In other preferred embodiments, the β-netrin protein differs in amino acid sequence at up to 1, 2, 3, 5, or 10% of the residues from a sequence in SEQ ID NO:2 or SEQ ID NO:5. Preferably, the differences are such that: the β-netrin protein exhibits a β-netrin biological activity, e.g., the β-netrin protein retains a biological activity of a naturally occurring β-netrin.

In another aspect of the invention, the β-netrin protein is a recombinant β-netrin protein which differs from β-netrin isolated from tissue. For example, the recombinantly produced β-netrin (rβ netrin) can differ in amino acid sequence from naturally occurring β-netrin, e.g., a β-netrin lacking the frz domain. In another preferred embodiment, rβ netrin can differ from naturally occurring β-netrin by one or more of the following: its pattern of glycosylation, myristylation, phosphorylation, or other posttranslational modifications. In one embodiment, the recombinant β-netrin can essentially consist of the frz domain. Preferably, the recombinant frz domain retains a biological activity of a naturally occurring frz domain. The recombinant frz domain can inhibit β-netrin activity by disrupting β-netrin dimerization.

The β-netrin protein of the invention, or portions or fragments thereof, can be used to prepare anti-β netrin antibodies. Accordingly, the invention also provides an antigenic peptide of β-netrin which includes at least 8 amino acid residues of the amino acid sequence shown in SEQ ID NO:2 or SEQ ID NO:5 and encompasses an epitope of β-netrin such that an antibody raised against the peptide forms a specific immune complex with β-netrin. Preferably, the antigenic peptide includes at least 10 amino acid residues, more preferably at least 15 amino acid residues, even more preferably at least 20 amino acid residues, and most preferably at least 30, 50, 70, 80 amino acid residues. The invention further provides an antibody, e.g., a monoclonal antibody, which specifically binds β-netrin. In one embodiment, the antibody is monoclonal. In another embodiment, the antibody is coupled to a detectable substance. In yet another embodiment, the antibody is incorporated into a pharmaceutical composition comprising the antibody and a pharmaceutically acceptable carrier.

In another aspect, the invention features, a method of modulating a β-netrin mediated property of a cell, in vitro or in vivo. The method includes contacting the cell with an agent which modulates an activity of β-netrin. β-netrin activity can be modulated, e.g., transcriptionally, translationally, or post-translationally.

In a preferred embodiment, the method: modulates (e.g., attract or repel) neurite outgrowth, guidance (e.g., guidance of central nervous system axons and peripheral motor neurons), and/or stability (e.g., synapses stability); modulates development of the central nervous system, e.g., development of the spinal cord, development of the optic system (e.g., retina), e.g., development of the olfactory system; modulates development of areas of the brain; modulates angiogenesis, e.g., inhibits or increases angiogenesis; modulates proliferative disorders, e.g., cancer, e.g., cervical, ovarian or colorectal cancer; modulates tumorigenesis; e.g., modulates kidney function and/or morphogenesis; regulates the maturation of ovarian follicles; and modulates muscular development, e.g., differentiation and/or innervation of musculature of the heart, arterioles, fallopian tubes, lamina propria, and other smooth muscle.

In a preferred embodiment, the method includes treating a subject having a disorder characterized by unwanted or aberrant β-netrin protein activity or nucleic acid expression.

In a preferred embodiment, the method includes treating a subject having a disorder associated with unwanted or abnormal cellular interactions (e.g., unwanted or abnormal neurite outgrowth, guidance or stability; unwanted or abnormal angiogenesis, e.g., unwanted angiogenesis to cancer cells).

In a preferred embodiment, one or more of the activity of β-netrin is modulated by modulating: 1) an interaction, directly or indirectly, with a β-netrin receptor; 2) an interaction, directly or indirectly, with intracellular signaling proteins; 3) properties of extracellular matrix basement membrane; dimerization of β-netrin with another molecule, e.g., a netrin, e.g., another β-netrin.

In a preferred embodiment, the agent which modulates β-netrin activity can be an agent which increases β-netrin protein activity or β-netrin nucleic acid expression. Examples of agents which increase β-netrin protein activity or β-netrin nucleic acid expression include small molecules (e.g., small molecules which bind to the promoter region of β-netrin), β-netrin proteins or functional fragments thereof, and nucleic acids encoding β-netrin or functional fragments thereof that have been introduced into the cell. In another embodiment, the agent which modulates β-netrin activity can be an agent which decreases β-netrin protein activity or β-netrin nucleic acid expression. Examples of agents which inhibit β-netrin activity or expression include small molecules (e.g., small molecules that bind β-netrin, e.g., small molecules which binds a control region of β-netrin); antisense β-netrin nucleic acid molecules; β-netrin binding polypeptides, e.g., a polypeptide selected for binding by phage display or two hybrid assay; and antibodies that specifically bind to β-netrin or to its target receptor. In a preferred embodiment, the cell is present within a subject and the agent is administered to the subject.

In a preferred embodiment, the subject has a disorder of tumorigenesis. The subject is administered an agent which increases β-netrin protein or nucleic acid activity. In another preferred embodiment, the subject has a disorder of cell proliferation. The subject is administered an agent which increases β-netrin protein or nucleic acid activity. In still another preferred embodiment the subject has a disorder of excessive angiogenesis, e.g., angiogenesis which supplies nutrients to tumors. The subject is administered an agent which increases β-netrin protein or nucleic acid activity. In another embodiment, the subject has a fertility disorder, e.g., a disorder of follicle cell maturation. The subject is administered an agent which increases β-netrin protein or nucleic acid activity.

In another aspect, the invention features, a method of treating a subject having a disorder characterized by unwanted or abnormal β-netrin activity. The method includes contacting the cell with an agent which modulates the activity of β-netrin. β-netrin activity can be modulated, e.g., transcriptionally, translationally, or post-translationally.

In a preferred embodiment, the method: modulates (e.g., attracts or repels) neurite outgrowth, guidance (e.g., guidance of central nervous system axons and peripheral motor neurons), and/or stability (e.g., synapses stability); modulates development of the central nervous system, e.g., development of the spinal cord, development of the optic system (e.g., retina), e.g., development of the olfactory system; modulates development of areas of the brain; modulates angiogenesis, e.g., inhibits or increases angiogenesis; modulates proliferative disorders, e.g., cancer (e.g., cervical, ovarian or colorectal cancer); modulates tumorigenesis; e.g., modulates kidney function and/or morphogenesis; regulates the maturation of ovarian follicles; and modulates muscular development, e.g., differentiation and/or innervation of musculature of the heart, arterioles, fallopian tubes, lamina propria, and other smooth muscle.

In a preferred embodiment, one or more of the activities of β-netrin is modulated by modulating: 1) an interaction, directly or indirectly, with a β-netrin receptor; 2) an interaction, directly or indirectly, with intracellular signaling proteins; 3) properties of extracellular matrix basement membrane; 4) dimerization of β-netrin with another molecule, e.g., a netrin e.g., another β-netrin.

In a preferred embodiment, the agent which modulates β-netrin activity can be an agent which increases β-netrin protein activity or β-netrin nucleic acid expression. Examples of agents which increase β-netrin protein activity or β-netrin nucleic acid expression include small molecules (e.g., small molecules which bind to the promoter region of β-netrin), β-netrin proteins or functional fragments thereof, and nucleic acids encoding β-netrin or functional fragments thereof that have been introduced into the cell. In another embodiment, the agent which modulates β-netrin activity can be an agent which decreases β-netrin protein activity or β-netrin nucleic acid expression. Examples of agents which inhibit β-netrin activity or expression include small molecules (e.g., small molecules that bind β-netrin, e.g., small molecules which binds a control region of β-netrin); antisense β-netrin nucleic acid molecules; β-netrin binding polypeptides, e.g., a polypeptide selected for binding by phage display or two hybrid assay; and antibodies that specifically bind to β-netrin or to its target receptor. In a preferred embodiment, the cell is present within a subject and the agent is administered to the subject.

In a preferred embodiment, the disorder is a neurodegenerative disorder, e.g., multiple sclerosis, or an acute neurological disorder, e.g., mechanical trauma to the nervous system. In another preferred embodiment, the disorder is a disorder characterized by unwanted angiogenesis, e.g., angiogenesis of cancer cells, e.g., angiogenesis in tumors, or aberrant angiogenesis. The subject is administered an agent which increases β-netrin protein or nucleic acid activity.

In a preferred embodiment, the subject has a disorder of tumorigenesis. The subject is administered an agent which increases β-netrin protein or nucleic acid activity. In another preferred embodiment, the subject has a disorder of cell proliferation. The subject is administered an agent which increases β-netrin protein or nucleic acid activity. In another embodiment, the subject has a fertility disorder, e.g., a disorder of follicle cell maturation. The subject is administered an agent which increases β-netrin protein or nucleic acid activity.

In another aspect, the invention features a method of modulating β-netrin dimerization. The method includes using an agent which inhibits or enhances β-netrin frz domain dimerization. In one embodiment, the agent inhibits dimerization. In a preferred embodiment, the agent is an antibody, e.g., a monoclonal antibody, a F(ab)', a Fab, a single-chain, or a humanized antibody. The antibody can bind specifically to the β-netrin frz domain to thereby inhibit dimerization. A preferred antibody can bind to dimerized β-netrin molecules and disrupt dimerization. In another preferred embodiment, the agent is a polypeptide other than an antibody. The polypeptide can bind to the netrin frz domain to thereby inhibit or disrupt dimerization. In yet another preferred embodiment, the agent is a small organic molecule. The molecule can bind to the β-netrin frz domain to thereby inhibit or disrupt dimerization.

In another embodiment of the method of modulating β-netrin dimerization, the agent enhances dimerization. The agent can bind the dimerization interface and stabilize the interaction. Alternatively, the agent can bind to the frz domain and stabilize a preferred conformation or prevent unfolding. In a preferred embodiment, the agent is a polypeptide, e.g., a polypeptide which can bind to the β-netrin frz domain. In another preferred embodiment, the agent is an antibody, e.g., a monoclonal antibody, a F(ab)', a Fab, a single-chain, or a humanized antibody, an antibody which can bind to the β-netrin frz domain. In still another preferred embodiment, the agent is a small organic compound, which binds to the frz domain to enhance dimerization.

In another aspect, the invention features a method of reducing angiogenesis in a subject. The method includes administering to the subject an effective amount of β-netrin polypeptide or nucleic acid. In one embodiment, an effective amount of the β-netrin polypeptide is utilized. The β-netrin polypeptide or functional fragment thereof can be provided as a pharmaceutical formulation, e.g., with appropriate carriers, excipients, and the like. The polypeptide can be provided orally, parenterally, or locally (e.g., by injection or surgery, or with a targeting agent). For example, the β-netrin polypeptide can be targeted to a tumor by coupling to an antibody against a tumor specific antigen. In another embodiment, a β-netrin nucleic acid is administered, e.g. in a gene therapy vector, e.g. in a vector targeted to tumor cells.

In another aspect, the invention features a method of treating tumorigenesis in a subject. The method includes administering to the subject an effective amount of β-netrin polypeptide or nucleic acid. In one embodiment, an effective amount of the β-netrin polypeptide is utilized. The β-netrin polypeptide or functional fragment thereof can be provided as a pharmaceutical formulation, e.g., with appropriate carriers, excipients, and the like. The polypeptide can be provided orally, parenterally, or locally (e.g., by injection or surgery, or with a targeting agent). For example, the β-netrin polypeptide can be targeted to a tumor by coupling to an antibody against a tumor specific antigen. In another embodiment, a β-netrin nucleic acid is administered, e.g. in a gene therapy vector, e.g. in a vector targeted to tumor cells.

The invention also features methods for evaluating a subject at risk for a disorder. The method includes evaluating, e.g., detecting, a genetic lesion in the β-netrin gene, or evaluating, e.g., detecting, misexpression of the β-netrin gene, thereby determining if a subject is at risk for (e.g., has or is predisposed to have) a disorder. The disorder can be one which is characterized by aberrant or abnormal β-netrin nucleic acid expression and/or β-netrin protein activity. In a preferred embodiment, the method includes evaluating, e.g., in a sample of cells from the subject, the presence or absence of a genetic lesion, e.g., a lesion characterized by an alteration affecting the gene encoding a β-netrin protein, or evaluating the misexpression of the β-netrin gene. Genetic lesions can be evaluated, e.g., by contacting the sample with a nucleic acid probe capable of hybridizing to β-netrin mRNA, e.g., a labeled probe. Expression can be evaluated with an antibody capable of binding to β-netrin protein, e.g., a labeled antibody. In a preferred embodiment, the method can also be used in fetal or neonatal diagnosis.

Another aspect of the invention features methods for detecting the presence of β-netrin nucleic acid or protein in a biological sample. In a preferred embodiment, the method involves contacting a biological sample (e.g., a cell sample) with a compound or an agent capable of detecting β-netrin protein or β-netrin nucleic acid, e.g., mRNA, such that the presence of β-netrin nucleic acid or protein is detected in the biological sample. The compound or agent can be, for example, a labeled or labelable nucleic acid probe capable of hybridizing to β-netrin mRNA or a labeled or labelable antibody capable of binding to β-netrin protein. The invention further provides methods for diagnosis of a subject with, for example, a disorder associated with abnormal β-netrin expression or activity based on detection of β-netrin protein or mRNA. In one embodiment, the method involves contacting a cell or tissue sample (e.g., a biopsy sample) from the subject with an agent capable of detecting β-netrin protein or mRNA, determining the amount of β-netrin protein or mRNA expressed in the cell or tissue sample, comparing the amount of β-netrin protein or mRNA expressed in the cell or tissue sample to a control sample and forming a diagnosis based on the amount of β-netrin protein or mRNA expressed in the cell or tissue sample as compared to the control sample. Specific diagnostic tests are described in greater detail below. Kits for detecting β-netrin nucleic acid or protein in a biological sample are also within the scope of the invention.

Still another aspect of the invention features methods, e.g., screening assays, for identifying a compound for treating a disorder characterized by aberrant β-netrin nucleic acid expression and/or protein activity. These methods typically include assaying the ability of the compound or agent to modulate the expression of the β-netrin gene or the activity of the β-netrin protein, thereby identifying a compound for treating a disorder characterized by aberrant β-netrin nucleic acid expression and/or protein activity. In a preferred embodiment, the method involves contacting a biological sample, e.g., a cell or tissue sample, obtained from a subject having the disorder with the compound or agent, determining the amount of β-netrin protein expressed and/or measuring the activity of the β-netrin protein in the biological sample, comparing the amount of β-netrin protein expressed in the biological sample and/or the measurable β-netrin biological activity in the cell to that of a control sample. An alteration in the amount of β-netrin protein expression and/or β-netrin activity in the cell exposed to the compound or agent in comparison to the control is indicative of a modulation of β-netrin expression and/or β-netrin activity.

The invention also features methods for identifying a compound or agent which interacts with a β-netrin protein. In a preferred embodiment, the interaction with a β-netrin protein can be binding, phosphorylation, or otherwise interacting to form or break a bond, e.g., a covalent or non-covalent bond. A compound can include, for example, a randomly generated polypeptide which interacts with β-netrin, or a small molecule. In a preferred embodiment, the method can include the steps of contacting the β-netrin protein with the compound or agent under conditions which allow binding of the compound to the β-netrin protein to form a complex and detecting the formation of a complex of the β-netrin protein and the compound in which the ability of the compound to bind to the β-netrin protein is indicated by the presence of the compound in the complex. Methods for identifying a compound or agent can be performed, for example, using a cell free assay. For example, β-netrin can be immobilized to a suitable substrate, e.g., glutathione sepharose beads or glutathione derivatized microtitre plates, using a fusion protein which allows for β-netrin to bind to the substrate, e.g., a transferase-S-transferase/β netrin fusion protein.

In another embodiment, a compound or agent which interacts with a β-netrin protein can be identified using a cell-based assay. These methods can include identifying a compound or agent based on its ability to modulate, e.g., inhibit or promote, a biological activity of β-netrin. In a preferred embodiment, the compound modulates one or more of the following biological activities of β-netrin: 1) the ability to modulate (e.g., attract or repel) neurite outgrowth, guidance, e.g., guidance of central nervous system axons and peripheral motor neurons, and/or stability, e.g., synapses stability; 2) ability to modulate development of the central nervous system, e.g., development of the spinal cord, development of the optic system (e.g., retina), e.g., development of the olfactory system; 3) ability to modulate development of areas of the brain; 4) ability to modulate angiogenesis, e.g., inhibit angiogenesis in tumors; 5) ability to modulate proliferative disorders, e.g., cancer, e.g., cervical, ovarian or colorectal cancer; 6) the ability to modulate development of the kidney (e.g., morphogenesis of tubules and glomeruli); 7) the ability to modulate the maturation of ovarian follicles; and 8) the ability to modulate muscular development and/or innervation (e.g., musculature of the heart, arterioles, fallopian tubes, and lamina propria), especially smooth muscle.

In another aspect, the invention features methods for identifying compounds which modulate β-netrin nucleic acid expression. In a preferred embodiment, nucleic acid expression can be evaluated using a nucleic acid probe, e.g., a labeled probe, capable of hybridizing to a β-netrin nucleic acid molecule, e.g., β-netrin mRNA. In another preferred embodiment, β-netrin nucleic acid expression, e.g., DNA expression, can be evaluated by contacting a compound with a β-netrin nucleic acid molecule, e.g., a control region of a β-netrin nucleic acid molecule, and evaluating β-netrin transcription, in vitro or in vivo. β-netrin transcription can be evaluated, for example, by detecting the production of β-netrin protein, e.g., using an antibody, e.g., a labeled antibody, or by determining a cell activity, e.g., using a marker gene, e.g., a lacZ gene, fused to the control region of β-netrin and following production of the marker.

The invention further features methods for identifying a compound or agent which modulates, e.g., stimulates or inhibits, the interaction of the β-netrin protein with a target molecule, e.g., a β-netrin receptor or a protein involved in a signaling pathway. In these methods, the β-netrin protein is contacted, in the presence of the compound or agent, with the target molecule under conditions which allow binding of the target molecule to the β-netrin protein to form a complex. An alteration, e.g., an increase or decrease, in complex formation between the β-netrin protein and the target molecule as compared to the amount of complex formed in the absence of the compound or agent is indicative of the ability of the compound or agent to modulate the interaction of the β-netrin protein with a target molecule.

A "heterologous promoter", as used herein is a promoter which is not naturally associated with a gene or a purified nucleic acid.

A "purified" or "substantially pure" or isolated "preparation" of a polypeptide, as used herein, means a polypeptide that has been separated from other proteins, lipids, and nucleic acids with which it naturally occurs. Preferably, the polypeptide is also separated from substances, e.g., antibodies or gel matrix, e.g., polyacrylamide, which are used to purify it. Preferably, the polypeptide constitutes at least 10, 20, 50 70, 80 or 95% dry weight of the purified preparation. Preferably, the preparation contains: sufficient polypeptide to allow protein sequencing; at least 1, 10, or 100 μg of the polypeptide; at least 1, 10, or 100 mg of the polypeptide.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

A "treatment", as used herein, includes any therapeutic treatment, e.g., the administration of a therapeutic agent or substance, e.g., a drug.

As used herein, the term "subject" refers to human and non-human animals. In preferred embodiments, the subject is a human. The term "non-human animals" of the invention includes all vertebrates, e.g., mammals and non-mammals, such as non-human primates, ruminants, birds, amphibians, and reptiles.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

"Sequence identity or homology", as used herein, refers to the sequence similarity between two polypeptide molecules or between two nucleic acid molecules. Calculations of homology or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to a β-netrin amino acid sequence having 200 amino acid residues, at least 60, preferably at least 80, more preferably at least 100, even more preferably at least 120, and even more preferably at least 140, 160 or 180 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg-.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to beta-netrin nucleic acid molecules of the invention. BLAST protein searches can be performed with the XBLAST program, score=50, wordlength=3 to obtain amino acid sequences homologous to beta-netrin protein molecules of the invention. To obtain gapped alignments for comparison purposes, Gapped BLAST can be utilized as described in Altschul et al., (1997) *Nucleic Acids Res.* 25(17): 3389-3402. When utilizing BLAST and Gapped BLAST programs, the default parameters of the respective programs (e.g., XBLAST and NBLAST) can be used. See http://www.ncbi.nlm.nih.gov.

The terms "peptides", "proteins", and "polypeptides" are used interchangeably herein.

A "biological activity of β-netrin" refers to one or more of the following activities: 1) the ability to modulate (e.g., attract or repel) neurite outgrowth, guidance, e.g., guidance of central nervous system axons and peripheral motor neurons, and/or stability, e.g., synapses stability; 2) ability to modulate development of the central nervous system, e.g., development of the spinal cord, development of the optic system (e.g., retina), e.g., development of the olfactory system; 3) ability to modulate development of areas of the brain; 4) ability to modulate angiogenesis, e.g., inhibit angiogenesis in tumors; 5) ability to modulate proliferative disorders, e.g., cancer, e.g., cervical, ovarian or colorectal cancer.

The term "small molecule", as used herein, includes peptides, peptidomimetics, or non-peptidic compounds, such as organic molecules, having a molecular weight less than 2000, preferably less than 1000.

As used herein, the term "transgene" means a nucleic acid sequence (encoding, e.g., one or more subject β-netrin polypeptides), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic animal" is any animal in which one or more, and preferably essentially all, of the cells of the animal includes a transgene. The transgene can be introduced into the cell, directly or indirectly by introduction into a precursor of the cell, by way of deliberate genetic manipulation, such as by microinjection or by infection with a recombinant virus. This molecule may be integrated within a chromosome, or it may be extrachromosomally replicating DNA.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as mammary tissue. The term also covers so-called "leaky" promoters, which regulate expression of a selected DNA primarily in one tissue, but cause expression in other tissues as well.

"Unrelated to a β-netrin amino acid or nucleic acid sequence" means having less than 30% sequence identity, less than 20% sequence identity, or, preferably, less than 10% homology with a naturally occurring β-netrin sequences disclosed herein.

A polypeptide has β-netrin biological activity if it has one or more of the properties of β-netrin disclosed herein. A polypeptide has biological activity if it is an antagonist, agonist, or super-agonist of a polypeptide having one of the properties of β-netrin disclosed herein.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

As described herein, one aspect of the invention features a substantially pure (or recombinant) nucleic acid which includes a nucleotide sequence encoding a β-netrin polypeptide and/or equivalents of such nucleic acids. The term nucleic acid as used herein can include fragments and equivalents. The term equivalent refers to nucleotide sequences encoding functionally equivalent polypeptides. Equivalent nucleotide sequences will include sequences that differ by one or more nucleotide substitutions, additions or deletions, such as allelic variants, and include sequences that differ from the nucleotide sequences disclosed herein by degeneracy of the genetic code.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6×sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. Preferably, an isolated nucleic acid molecule of the invention that hybridizes under stringent conditions to the sequence of SEQ ID NO:1 or SEQ ID NO:4 corresponds to a naturally occurring nucleic acid molecule.

As used herein, a "naturally-occurring" nucleic acid molecule refers to an RNA or DNA molecule having a nucleotide sequence that occurs in nature (e.g., encodes a natural protein). In one embodiment, the nucleic acid encodes a natural β-netrin protein.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of β-netrin protein having less than about 30%, 20%, 10% and more preferably 5% (by dry weight), of non-β-netrin protein (also referred to herein as a "contaminating protein"), or of chemical precursors or non-β-netrin chemicals. When the β-netrin protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I-IV (D. M. Weir and C. C. Blackwell, eds., 1986); *Manipulating the Mouse Embryo,* (Cold Spring Harbor Laboratory Press, Cold Spring Harbor, N.Y., 1986).

Other features and advantages of the invention will be apparent from the following detailed description, and from the claims.

BRIEF DESCRIPTION OF THE DRAWINGS

FIGS. 1A-B depicts the cDNA sequence and predicted amino acid sequence of human β-netrin. The nucleotide sequence corresponds to nucleic acids 1 to 3626 of SEQ ID NO:1. The coding sequence (SEQ ID NO:3) corresponds to nucleic acids 452 to 2333 of SEQ ID NO:2. The amino acid sequence corresponds to amino acids 1 to 628 of SEQ ID NO:2.

FIG. 2 depicts a partial cDNA sequence of murine β-netrin. The nucleotide sequence corresponds to nucleic acids 1 to 2048 of SEQ ID NO:4.

FIG. 3 depicts an alignment of the amino acid sequences of human β-netrin (top row)(corresponding to amino acids 1 to 628 of SEQ ID NO:2) and murine β-netrin (bottom row) (corresponding to amino acids 1 to 628 of SEQ ID NO:5). The percent identity between human and murine β-netrin (i.e., about 89% identity) is indicated by a dash in the bottom row. Cysteine residues in the human β-netrin amino acid sequence are underlined.

FIGS. 6A-C depicts the mouse β-netrin promoter sequence.

DETAILED DESCRIPTION OF THE INVENTION

Figure 4:
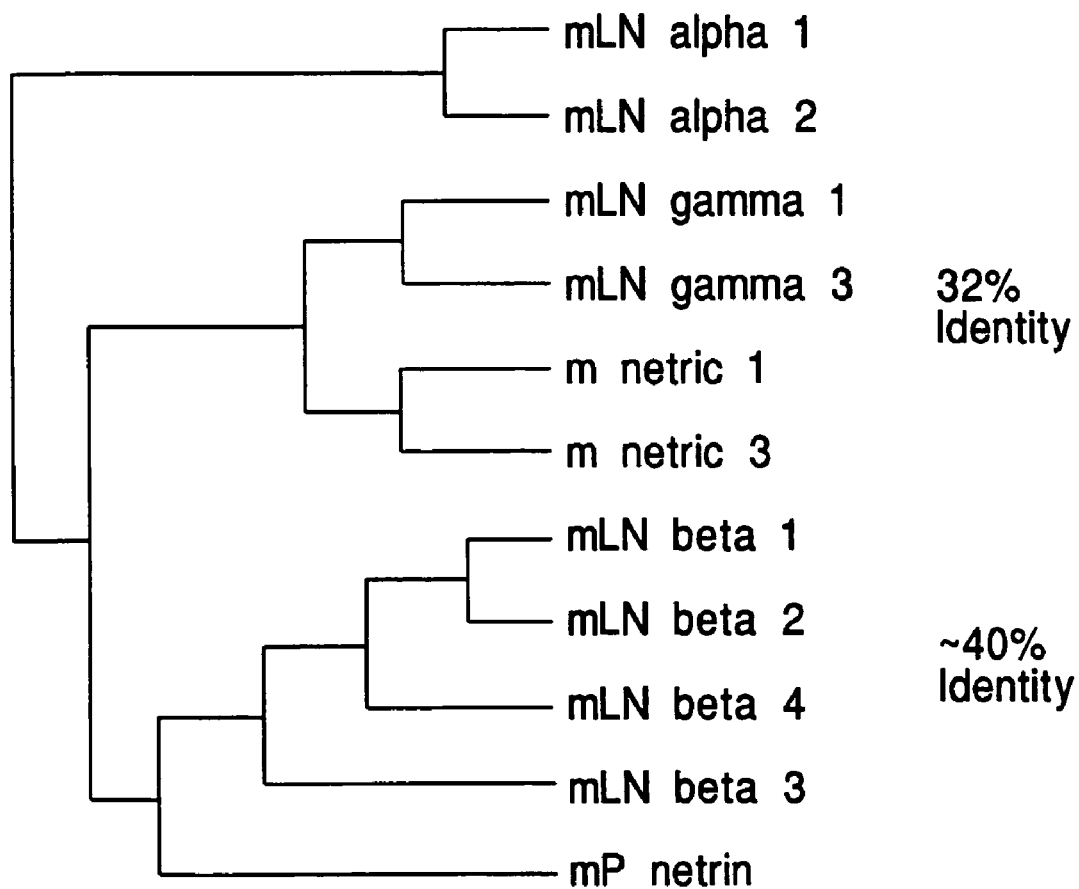
FIG. 4 depicts a phylogenic tree analysis of netrins based on the homology between the laminin VI and V domains and the laminin N-terminal (Domain VI) domain and the laminin EGF-like (Domain V) domain of various netrins. β-netrin has about 40% sequence identity with the laminin β domains VI and V and netrins 1 and 3 have about 32% sequence identity with the laminin β domains VI and V.

The present invention is based on the discovery of novel molecules, referred to herein as β-netrin nucleic acid and protein molecules, which play a role in neurite outgrowth and angiogenesis.

Axonal guidance during the development of the nervous system is highly regulated through the interactions of axons with attractive, repulsive and trophic cues. Similar mechanisms regulate axonal regeneration after injury. The netrins, e.g., netrins 1-3, have been implicated as axonal guidance cues for several developing neurons including interneurons. For example, the expression of several netrins has been found in muscle subsets where they attract some axons and repel others, thus controlling the ability of motor axons to recognize their appropriate targets (see Winberg et al. (1998) *Cell* 93:581-591).

Netrins comprise a family of structurally related secreted molecules involved in axon guidance. Axons sense netrins as either attractants or repellents, depending upon which netrin receptors are expressed on their growth cones (Hedgecock et al., 1990, *Neuron* 4:61-85; Serafini et al., 1994, *Cell* 78:409-424; Colamarino and Tessier Lavigne, (1995) *Cell* 81:621-

629; Winberg et al., 1998, supra), or differences in the cellular signal transduction machinery (Bashaw and Goodman, 1999, Cell 97:917-926).

To date, several netrins have been described. A single netrin, UNC-6, has been identified in *C. elegans* (Ishii et al., 1992, Neuron 9:873-881); two have been described in *Drosophila*: Netrin-A and Netrin-B (Harris et al., 1996; Neuron 17:217-228; Mitchell et al., 1996, Neuron 17:203-215). Three netrins have been identified in vertebrates: netrin-1 has been identified in chicken (Serafini et al., 1994, supra), mouse (Serafini et al., 1996, Cell 87:1001-1014), *Xenopus* (de la Terre et al., 1997, Neuron 19:1211-1224), zebrafish (Lauderdale et al., 1997 Mo. Cell Neurosci. 9:293-313; Strahle et al., 1997, Mech. Dev. 62:147-160), and human (Meyerhardt et al., 1999, Cell Growth Differ. 10:35-42); netrin-2 in chicken (Serafini et al., 1994, supra); netrin-3 in human (NTN2L, Van Raay et al., 1997, Genomics 41:279-282) and mouse (Wang et al., 1999, J. Neurosci 19:4938-4947). Netrins 1, 2 and 3 are all structurally related to the short arms of laminin γ chains, and contain a laminin VI domain and three epidermal growth factor-like (EGF-like) repeats similar to the laminin V domain (V-1, V-2 and V-3); they also contain a positively charged heparin-binding C-terminal domain termed "domain C" (Serafini et al., 1994, supra; Keino-Masu, 1996, Cell 87:175-185).

Mutations in the netrin genes in *C. elegans* (unc-6) (Hedgecock et al., 1990, supra), *Drosophila* (NetA/B) (Winberg et al., 1998, Cell 93:581-591), and mouse (netrin-1) (Skarnes et al., 1995, Proc. Nat. Acad. Sci. USA 92:6592-6596; Serafini et al., 1996, supra) produce defects in axon guidance affecting circumferential and commissural growth. Studies in vitro show that netrin-1 can act from a distance within a collagen gel to cause the outgrowth of spinal cord axons; implicating chemoattraction as the mechanism of action of netrins (Kennedy et al., 1994, Cell 78:425-435).

In mouse and chicken, the RNA transcripts encoding the netrins are widely distributed throughout the organism (Wang et al., 1999, J. Neurosci. 19:4938-4947). Netrin RNAs are prominent in embryonic muscle and the bronchi of lung; transcripts are also present in the condensing mesenchyme of the limb and esophagus. However, netrin RNA location has been most extensively documented in the CNS. Netrin-1 is strongly expressed in the developing spinal cord, in the floorplate and the ventral ventricular zone (Serafini et al., 1996, supra; Wang et al. 1999, supra; Puschel, 1999, Mech. Dev. 83:65-75). Netrin-2 is expressed throughout the spinal cord and in the dorsal root ganglia, but not in the floor plate (Wang et al., 1999, supra). Netrin-3 is expressed more limitedly in the dorsal root ganglia and the motor column of the ventral spinal cord (Wang et al., 1999, supra; Puschel, 1999, supra).

The effect of netrins upon axon extension in vitro, together with the tightly restricted regional expression of netrin RNAs within targets of axon outgrowth, support the generally held hypothesis that netrins act as diffusible attractants or repellants for responsive axons. However, localization of netrin-1 protein in the chicken brain, retina, and spinal cord appear to contradict this concept (MacLennan et al., 1997, J. Neurosci. 17:5466-5479). For example, in the spinal cord, although netrin-1 RNA is localized where the commissural fibers cross in the floorplate, netrin-1 protein is not concentrated within the floor plate. Rather, netrin-1 protein is deposited in or near the basement membrane of the spinal cord. Similarly, Netrin-A and Netrin-B proteins are localized at the *Drosophila* midline in a manner analogous to that in the chicken spinal cord (Harris et al., 1996, supra). Thus, these netrins function through a haptotactic, rather than chemoattractive mechanism (MacLennan et al., 1997, supra). The ability of netrins to bind heparin through the C domain (Serafini et al., 1994, supra; Keino-Masu et al., 1996, supra) is consistent with a haptotactic function, as this binding suggests that netrins may be immobilized in tissues, either to cell surfaces or to components of the extracellular matrix.

β-netrin is expressed in various areas of the nervous system including the whole brain, retina and olfactory bulb and has been found to play a role in neurite outgrowth in various neural tissues including the retina and olfactory bulb. Thus, β-netrin proteins or polypeptides of the invention play a role in the development and/or regeneration of the nervous system in one or more of the following activities: 1) the ability to modulate (e.g., attract or repel) neurite outgrowth, guidance, e.g., guidance of central nervous system axons and peripheral motor neurons, and/or stability, e.g., synapses stability; 2) ability to modulate development of the central nervous system, e.g., development of the spinal cord, development of the optic system (e.g., retina), e.g., development of the olfactory system; 3) ability to modulate development of areas of the brain; 4) ability to modulate angiogenesis, e.g., inhibit angiogenesis in tumors; 5) ability to modulate proliferative disorders, e.g., cancer, e.g., cervical, ovarian or colorectal cancer; 6) the ability to modulate development of the kidney (e.g., morphogenesis of tubules and glomeruli); 7) the ability to modulate the maturation of ovarian follicles; and 8) the ability to modulate muscular development and/or innervation (e.g., musculature of the heart, arterioles, fallopian tubes, and lamina propria), especially smooth muscle.

The present invention includes β-netrin polypeptides and fragments thereof which can be deposited into the extracellular milieu, e.g., into the basement membrane, and which modulate a process described herein. For example, the polypeptides are contacted by a cell and provide a haptotactic signal to modulate a cellular process. Also contemplated by the present invention are β-netrin polypeptides or soluble fragments thereof which are diffusible agents that modulate a process described herein. For example, the polypeptides provide a chemotactic signal to modulate a cellular process.

β-netrin has also been found to be strongly localized in the smooth muscles of blood vessels. Thus, the β-netrin proteins or polypeptides of the invention likely play a role in modulating, e.g., increasing or decreasing, angiogenesis, e.g., by modulating smooth muscle formation of a blood vessel. In particular, β-netrin can play a role in inhibiting angiogenesis and, thus, may be useful in preventing angiogenesis, for example, to tumor cells.

Isolation and Cloning of Human and Murine β-netrin cDNA

Figure 1A-1:
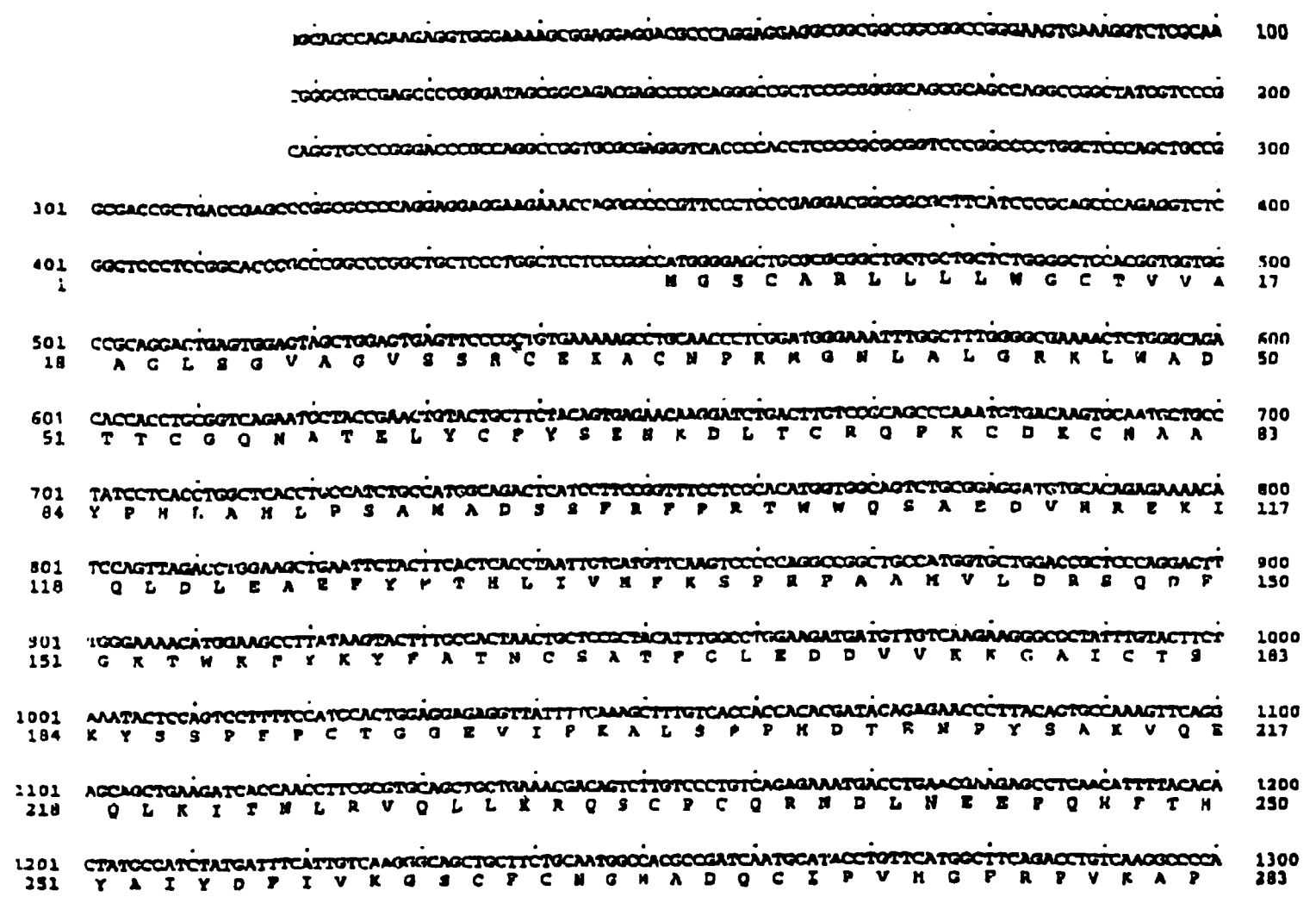
Figure 1A-2:
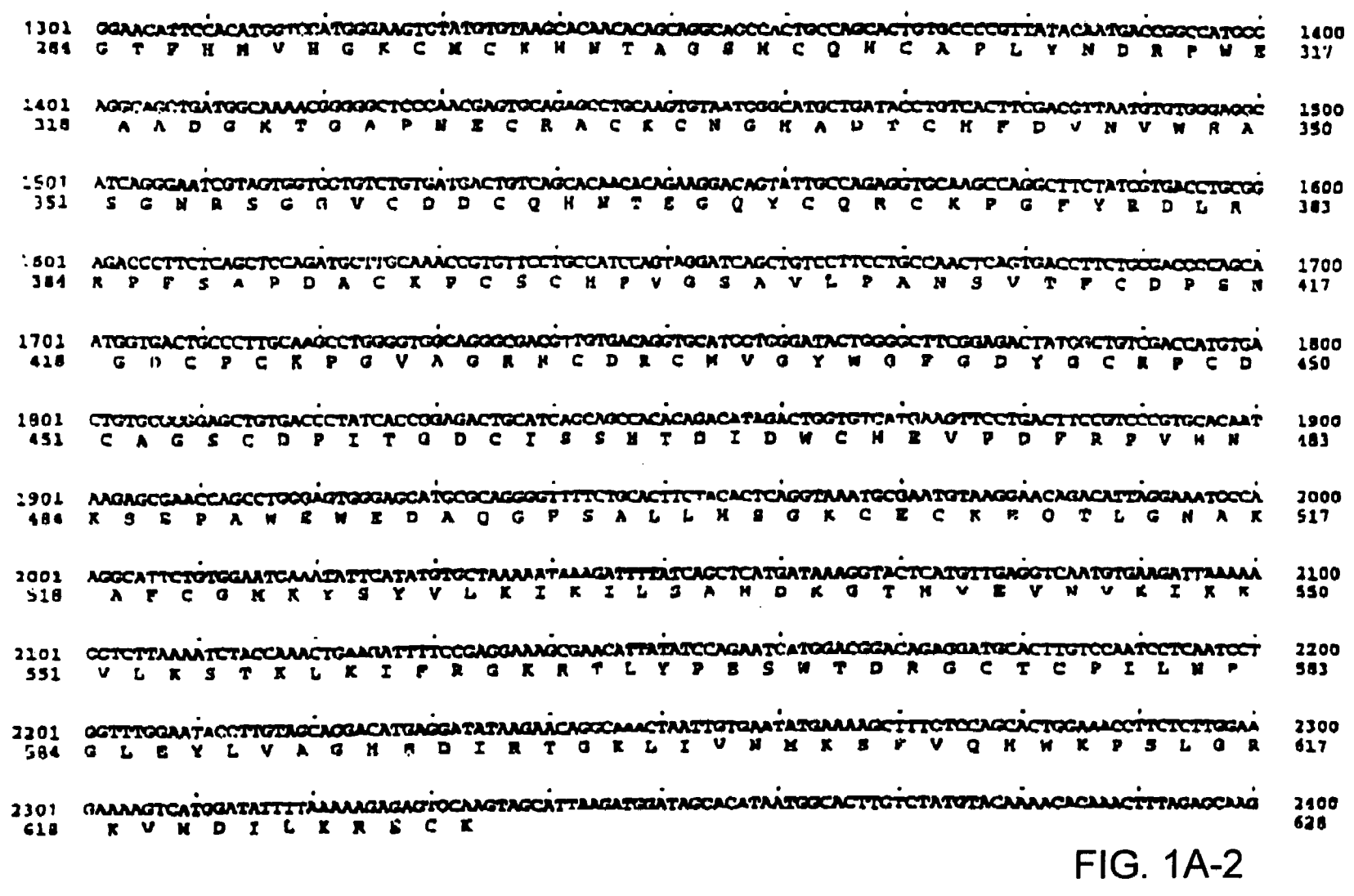
Figure 1B:
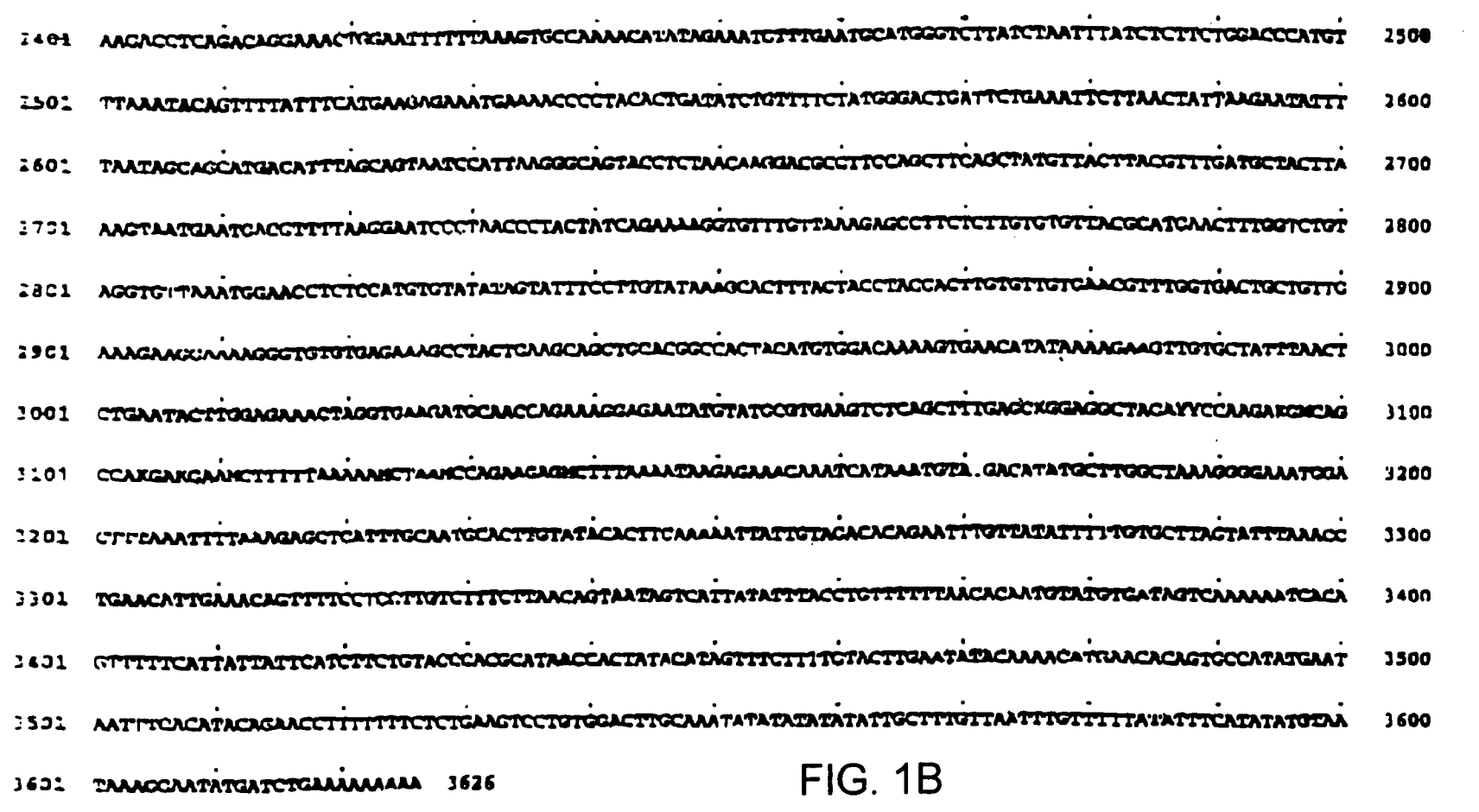

Human β-netrin: A unique partial cDNA sequence was identified in the dBEST sequence database by searching for sequences homologous to laminin EGF-like repeats. Clone # AA584649 was obtained and the sequence was extended using rapid amplification of cDNA ends (RACE), resulting in the full length human cDNA. The full-length human β-netrin cDNA was obtained as shown in FIG. 1 (SEQ ID NO:1). Specific primers for 5' or 3' extension were deduced from that expressed sequence tag and nested polymerase chain reactions (PCR) were performed on human 7-8 week fetal cDNA or human placental cDNA to extend the clone, using "Marathon Ready cDNA" (Clontech; Palo Alto, Calif.) following the manufacturer's instructions. For PCR, the Long Expand PCR Kit (Boehringer Mannheim; Indianapolis, Ind.) was used with the following conditions: denaturation, 94° C. for 3 min; 10 cycles of 94° C. for 30 s, 63° C. (−0.5° C. per cycle) for 30 s, 68° C. for 4 min; 25 cycles of 94° C. for 30 s, 58° C. for 30 s, 68° C. for 4 min (+10 s per cycle); a final extension period at 68° C. of 8 min.

Mouse β-netrin: To clone the mouse β-netrin, nested PCR was performed on reverse-transcribed embryonic day. 15.5 (E15.5) mouse RNA using, for the first PCR round, the primers Fv1 (5'dCTGAAACGACAGTCTTGTCCCTG (SEQ ID NO:6)) and Rv1 (5'-dTAATGTCTGTTCCTTACTTCGCA (SEQ ID NO:7)), and, for the second PCR round, nested primers Nfv2 (5'-dCATTGTCAAGGGCAGCTGCTTCTG (SEQ ID NO:8)) and NRv2 (5'-dGCCACCCCAGGCTTG-CAAGGGCA (SEQ ID NO:9). The PCR conditions were as follows: 1 U Taq-polymerase (Fisher Scientific); denaturation, 94° C. for 3 min; 10 cycles of 94° C. for 30 s, 50° C. (−0.5° C. per cycle) for 30 s, 72° C. for 1 min; 25 cycles of 94° C. for 30 s, 60° C. for 30 s, 72° C. for 1 min; a final extension period at 72° C. of 5 min. The 500 bp PCR product was purified on an agarose gel and directly sequenced. The sequence information was used to generate primers which were used in nested polymerase chain. reactions (PCR) using embryonic day 17 (E17) mouse cDNA (Marathon-Ready; Clontech, Palo Alto, Calif.) to elongate the 3' and 5' ends of the mouse β-netrin cDNA.

To generate a genetic distance map of the netrins and laminins, the N-termini of protein sequences, were analyzed with the GrowTree program (SeqWeb: Genetics Computer Group Inc., Wisconsin); the following laminin and netrin protein sequences were used: netrin-1 (AF128865); netrin 3 (AF128866); laminin a1 chain (504064); laminin a2 chain (MMU12147); laminin p1 chain (M15525); laminin p2 chain (AH006792); laminin p3 chain (U43298); laminin y1 chain (503484); laminin f1 chain (AF079520). Protein sequence starting from the VI domain through the 3 laminin-EGF modules in domain IV were analyzed. The Jukes-Cantor method was chosen to correct the distances for multiple substitutions at a single site; the tree was created with the unweighted pair group method using arithmetic averages (UPGMA) algorithm.

Nucleotide sequences were determined with a Thermo Sequenase cycle sequencing kit and $^{33}$P-ddNTPs (Amersham Pharmacia, Arlington Heights, Ill.) using either M13 forward or reverse primers or gene-specific primers. A 1.5:1 ratio of inosine to guanosine was included in the sequencing mix. Sequence data were assembled and manipulated using Genetyx-Max 8.0 and Genestream-1 at http://www2.igh.cnrs.fr/ (Software Development Co., Ltd.; EERI, France). The signal peptide cleavage site was predicted using software services available at http://genome.cbs.dtu.dk/services/SignalP/ (Nielsen, et al., 1997).

Figure 2:
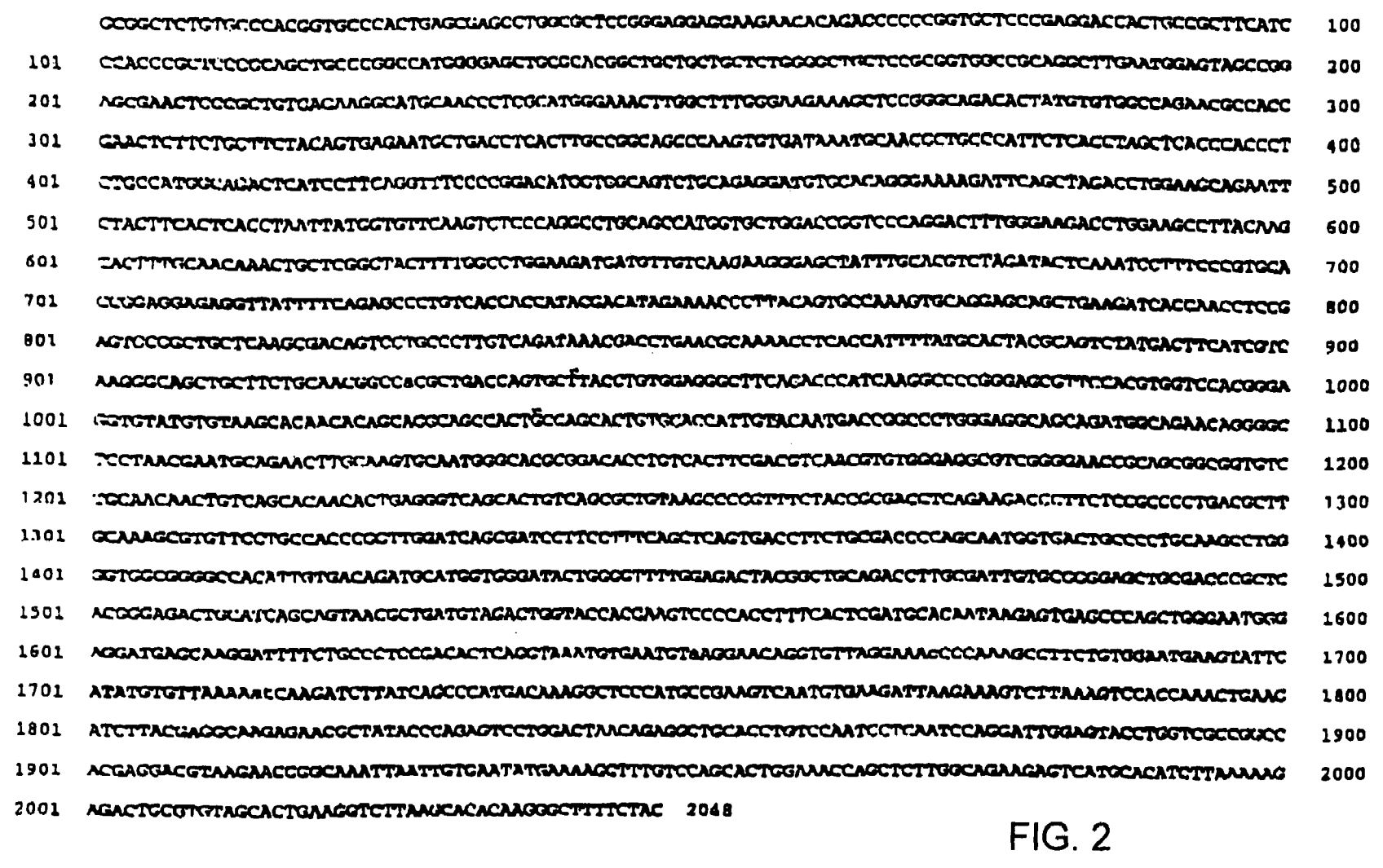

The mouse β-netrin cDNA sequence was obtained by nested PCR at low annealing temperatures, and nearly full length sequence was obtained, missing the polyadenylation site as shown in FIG. 2 (SEQ ID NO:4). The mouse β-netrin promoter as shown in FIG. 6 was obtained by RACE on mouse genomic DNA. It includes 5 kb of sequence prior to the ATG start site.

The sequence predicts a secreted molecule with an N-terminal domain similar to laminin β1 chain domain VI, a central domain containing an EGF-like domain similar to laminin β1 domain V, and a C-terminal domain homologous to netrin frz domains. The predicted amino acid sequence of human β-netrin and murine β-netrin as shown in FIG. 3 demonstrates the overall structure to be similar to a class of molecules known as netrins. Three netrins (netrins 1-3) have been previously described. All of netrins 1-3 contain two domains with homology to laminin β chain domains V and VI, and a C-terminal frz domain. β-netrin was so named because it has highest homology with the laminin P chains in contrast to netrins 1-3 which are homologous to the β chains.

The phylogenetic tree analysis of netrins shows β-netrin (also referred to as "mβnetrin") as shown in FIG. 4 to be about 40% identical to laminin β chains, while netrins 1-3 are about 32% identical to laminin β chains. Mouse β-netrin has about 31% sequence identity with mouse netrin-1.

Recombinant Expression of β-netrin

The following fragments of laminin chain cDNAs were amplified by PCR and subcloned into an episomal expression vector: human laminin γ2 short arm (per Amano et al., 2000, *J. Biol. Chem.*, advanced electronic publication); mouse laminin γ3 short arm, AF079520, nucleotide 1-3122 of SEQ ID NO:4; mouse laminin β2 short arm, NM_008483, nucleotide 174-3659 of SEQ ID NO:4. The following full lengths or fragments of netrin coding sequences were similarly obtained: mouse netrin-1, U65418, nucleotide 46-1812 of SEQ ID NO:4; mouse β-netrin, AF278532, nucleotide 311-2143 of SEQ ID NO:4; mouse β netrin-ΔC, AF278532, nucleotide 311-1672 of SEQ ID NO:4. 1 µg of total RNA from whole mouse embryo (day 17) was reverse transcribed and PCR was performed following the manufacturer's instructions (Pfu Turbo DNA Polymerase; Stratagene). The PCR product was purified on an agarose gel (Qiagen) and subcloned (rapid DNA ligation kit; Roche Diagnostics Gmbh) into a modified PCEP-4 expression vector. For convenience, a six histidine tag followed by a stop codon was introduced at the 3' end of the laminin γ2 and γ3 chains sequences, adjacent to the BamHI site of the PCEP-4 vector, and a six histidine tag followed by a thrombin cleavage site was included adjacent to the NheI site of the β-netrin, netrin1, and laminin β2 chain sequences. The ligated DNA was transformed into TOP 10 cells (Invitrogen). Plasmids were isolated from the bacteria (Qiagen) and sequenced with gene specific primers (Thermo Sequenase cycle sequencing kit; Amersham Pharmacia). In the case of the netrin-1 clone, a single amino acid-substitution, V to L, was detected at position nucleotide 295-7 of SEQ ID NO:1 (present in all the sequenced. clones, each of which were independent PCR products). 293-EBNA cells (Invitrogen) were transformed (FuGene; Roche Diagnostics Gmbh) with the expression vector and selected after two days with Puromycin (Sigma).

Stably transfected 293-EBNA cells were subcloned and the highest protein producing clones expanded for large scale production. Two liters of supernatant from these cells was collected and supplemented with 0.5 mM phenylmethylsulfonyl fluoride. After ammonium sulfate precipitation (45%), the precipitate was collected by centrifugation and then dialyzed against the binding buffer (200 mM NaCl, 20 mM Tris-HCl pH 8). The dialyzed protein was applied onto a Ni-chelated Sepharose column (Amersham Pharmacia Biotech AB) and washed and eluted with binding buffer containing increasing concentrations of imidazole (10-80 mM imidazole). In some cases, the histidine tag was digested with thrombin (isolated from bovine plasma; Sigma) according to the protocol from Novagen, Inc. The digested protein was again applied to a Ni-chelated Sepharose column and eluted with increasing imidazole concentration. The protein was dialyzed against PBS and the protein concentration was determined according to the protocol from Whitaker et al. (1980).

Full length recombinant β-netrin (rβ-N) including a His tag and thrombin cleavage site (rβ-N+His) was expressed using a mammalian expression vector in 293-EBNA cells. A shortened form of β-netrin lacking the C domain (rβ-NΔC), and full length recombinant mouse netrin-1 (rN1) were similarly produced. The expressed products were purified using a Ni$^{2+}$ containing column, and the His tag was removed in some cases by thrombin cleavage.

The calculated mass of rβ-N+His is 68 kDa; it migrates with an electrophoretic mobility predicting a final mass of 70 kDa. rβ-NΔC+His has electrophoretic mobility consistent with a mass of 56 kDa, which corresponds well with a predicted mass of 53 kDa. Removal of the His tag by thrombin cleavage reduces the apparent molecular weight slightly as expected. rβ-N+His and rβ-NAC+His, as well as recombinant laminin β2 short arm containing a His tag are all recognized by an anti-His antibody, but there is no reactivity against rβ-N following removal of the His tag.

Dimerization of β-netrin

Visualization of rβ-N by transmission electron microscopy following rotary shadowing indicates that the recombinant molecule is folded into structures resembling images of portions of laminin short arms. The VI domain measures about 8 nm in diameter and the short rod contributed by the EGF-like repeats and the C domain measures about 8.6 nm, giving an overall length of about 17 nm. The micrographs indicate that 44% (n=788) of the observed molecules associate to form dimers, and to a lesser extent (1.5%), higher order assemblies. The overall length of the dimer averages 24.6 nm, of which the two VI domains contribute 16 nm, leaving the VI domains separated by about 8.6 nm. Therefore, the images are consistent with dimerization occurring through anti-parallel linear alignment of the V and C domains. In rotary shadowed preparations of rβ-NΔC, on the other hand, most molecules appear to be monomeric globules with a short rod-like projection. This result suggests that the C domains are essential for β-netrin and are likely to interact with the V domain.

The rotary-shadowed images are most consistent with dimerization occurring via interactions in the C domain of one molecule with the V domain of its partner, as the VI domains are separated by the approximate length of one, but not two, V and C domains. If p-netrin dimerizes, in vivo, this could have implications for signal transduction. Dimerization can cluster β-netrin receptors on cells or can bridge two cells expressing such receptors. Dimerization of netrin receptors is a critical feature of signaling as the heterodimerization of Unc5h2 and DCC netrin receptors is necessary and sufficient to convert netrin attraction to repulsion (Hong et al. (1999), *Cell* 97:927-941). Alternatively dimerization can reduce activity and reduce the availability of effector binding sites.

Production and Characterization of Polyclonal and Monoclonal Antibodies to β-netrin Rabbits and mice were immunized with rβ-N+His. Three rabbits (R29, R32, and R33) and mice were immunized with rβ netrin. The rabbit antisera were purified using protein G to obtain IgG, and the isolated antibodies were affinity purified by column affinity chromatography using CNBr-activated Sepharose with attached rβ-NΔC from which the His tag had been removed by thrombin cleavage. The product of this protocol is termed pAbR33.

Hybridomas were produced from the mouse spleenic lymphocytes and clones 9F11 and 61 were determined to react with rp netrin and with rβ-N netrin and with rβ-NΔC netrin by ELISA and Western analysis.

All three antibody preparations; pAbR33, InAb9F11 and rnAb61, react identically by Western blot analysis. Specifically, all three react with a single band in the supernatants from cultured 293-EBNA cells expressing either rβ-N+His or rβ-NΔC+His. Coomassie blue staining of these culture supernatants shows multiple bands with the same or greater intensity than seen for the expression product. The identified bands have electrophoretic mobilities identical to rβ-N+His or rβ-NΔC+His. Removal of the His tag has no effect upon the antibodies ability to recognize either recombinant protein.

None of the antibodies react with recombinant laminin β2 short arm (which includes the His tag) by Western analysis. Thus, all three antibody preparations clearly recognize epitopes in domains V and VI of the molecule.

Given the high amino acid identity among the laminins and in the netrins in the V and VI domains, the reactivity of antibody preparations was compared to known expression patterns of laminin chains. Although all of the antibodies are useful in immunohistochemistry, none reacts with the basement membrane at the dermal-epidermal junction of skin by immunohistochemistry. Therefore, none of these antibodies cross-reacts with the laminin β1, β3, γ1, or γ2 chains. The distribution of β-netrin in the retina is also different than the distribution of either the laminin β2 or γ3 chain; therefore, the antibodies do not cross-reacting with these laminin chains.

The monoclonal anti-rβ-N antibody, 9F11, recognizes a conformation-specific epitope. No reactivity of 9F11 is seen following disulfide-bond reduction of the electrophoretic sample. The β-netrin species identified by 9F11 were not reduced, whereas those identified with the monoclonal 61 or pAbR33 were disulfide-bond reduced products. The species identified by the antibodies have the same electrophoretic mobilities, indicating that the molecules are not associated into disulfide-bonded aggregates. These data indicate that the β-netrin dimers visualized by rotary shadowing are not stabilized covalently.

Tissue Distribution of β-netrin cDNA

RT-PCR Analysis: RNA was isolated from animal tissues using the RNeasy kit (Qiagen), and cDNA was reverse-transcribed using an RT-PCR kit (Clontech) from the isolated RNA. PCR was performed on these using a long cDNAs expand PCR kit (Boehringer Mannheim) with GAPDH primers (forward: 5'-pTGAAGGTCGGTGTGAACGGA (SEQ ID NO:10); reverse: 5'-dGATGGCATGGACTGTGGTCA (SEQ ID NO:11)) and the amount of template was normalized for each tissue. A range of cycle numbers was tested to ensure the amounts were normalized in the linear range of the reaction. With the gene-specific primers (forward: 5'dGTAAGC-CCGGTTTCTACCGCGACC (SEQ ID NO:12; reverse: 5'dCCCTTGTGTGCTTAAGACCTTCAG (SEQ ID N:13)); another PCR was performed with the normalized cDNA templates using the following conditions: denaturation, 2 min; 94° C. 10 cycles of 94° C. for 30 seconds, 65° C. (−0.5° C. per cycle), for 30 seconds, 68° C. for 2 min; 22 cycles of 94° C. for 30 seconds, 60° C. for 30 seconds, 68° C. for 2 min (+10 seconds per cycle); and a final extension period at 68° C. for 5 min. The pair of gene-specific primers was selected from four pairs, which were each tested on the cDNAs for optimal amplification/cycle number. PCR products were confirmed by sequencing.

Northern Analysis: A 1.7 kbp PCR product (nucleotide 1114-nucleotide 2946) was labeled with $^{33}$P-dCTP (New England Nuclear) using the rediprime DNA labeling system (Amersham). Northern and dot blots (Clontech) were prehybridized in 50% formamide, 5×SSPE, 1×Denhardt's, 1% SDS, 10% Dextran-sulfate, 0.1 mg/ml salmon sperm DNA (Gibco BRL) at 42° C. for 2 h. Without further purification, the probe was denatured in the same buffer plus 1/10 v/v human Cot-1 DNA (Boehringer Mannheim), and 1/10 v/v sheared salmon testis DNA (Gibco BRL) at 94° C. for 5 min, placed on ice, added to the blots and hybridized for 20 h. Blots were washed three times in 2×SSC, 1% SDS at 42° C. and two times in 0.1×SSC, 1% SDS at 42° C. Blots were placed on BioMax MR film (Kodak, Rochester, N.Y.) with a BioMax TranScreen-LE intensifying screen (Kodak) for 20 h at −70° C.

RNA expression analysis using Northern blots of in human tissues probed with β-netrin showed that β-netrin is most highly expressed in kidney, spleen, mammary gland, aorta, heart, ovary, prostate, and fetal spleen. Next, semi-quantitative RT-PCR was also performed on various mouse tissues and confirmed that, as in humans, β-netrin expression is high in kidney; heart and ovary. In mouse, β-netrin expression was observed in neural tissues as well. A strong signal was obtained from whole brain and retina. Further analysis of the brain specific expression revealed that β-netrin was expressed at a low levels in most regions, with the exception of the olfactory bulb, where a high level expression was observed, approaching that seen in kidney, heart, and ovary.

Northern analysis showed β-netrin is most highly expressed in kidney, spleen, prostate, testis, ovary, mammary gland, heart and thymus. By PCR analysis, β-netrin cDNA was amplified from mouse neural tissue. A weak signal was seen everywhere with higher levels in whole brain, retina, and olfactory bulb, approaching the levels obtained from mouse kidney, heart and ovary.

In situ hybridization of large blood vessels demonstrated that β-netrin mRNA is localized to cells of the smooth muscle wall of vessels, as is the protein. β-netrin protein can be isolated from the supernatants of primary cultures of smooth muscle cells.

Tissue Distribution of β-netrin Protein

Tissue distribution of β-netrin was determined by indirect immunofluorescence using rat tissues. Basement membranes were stained in testis, ovary (during maturation of the follicles), the basement membranes and glomerulus of the kidney, and surrounding smooth muscle vasculature except in the brain. Some cell bodies in the brain do stain, but they have not yet been identified. Staining was also seen around the myoblasts of the heart.

Tissue distribution of β-netrin protein was determined by indirect immunofluorescence in various rat tissues and the cellular sources of β-netrin were determined by in situ hybridization. β-netrin is expressed in the basement membranes of a variety of tissues. In kidney, β-netrin protein is expressed in the basement membranes of all tubules. The major arteries and arterioles were prominently reactive with the anti-β-netrin antibody; as were the afferent arterioles. Particularly clear was the reactivity in the basal lamina surrounding the smooth muscle cells in the wall of the vessels. In addition, β-netrin immunoreactivity was present in the basement membrane of the rat glomerulus. This pattern of immunoreactivity is different than that reported for the laminin β2 chain (Hunter et al., 1989), further supporting a lack of cross-reactivity between these molecules. β-netrin transcripts, as judged by in situ hybridization, are localized to all cells in the kidney: tubular epithelial, vascular endothelial, mesangial and 'Bowman 's capsule cells; an equally well labeled probe with similar G-C content showed no hybridization. These observations suggest that β-netrin is a prominent element of the basement membrane and that both the epithelium and the mesenchyme contribute to its production.

RNA expression suggested high levels of β-netrin expression in the ovary. The tissue distribution of β-netrin was examined the distribution of β-netrin in the female reproductive system. β-netrin immunoreactivity was prominent in the ovary and the fallopian tube. For example, the basement membrane of the fallopian tube and the arterial smooth muscle in the lamina propria had high levels of β-netrin protein. In addition to the basal reactivity, there is some β-netrin immunoreactivity at the apical surface of the epithelium, suggesting the fallopian epithelium is at least one source of the molecule. In situ hybridization confirmed this; and demonstrated that β-netrin transcripts are localized to the apical and basal ends of the fallopian endothelium.

The ovary expresses β-netrin was also observed in the ovary. However, in contrast to both kidney and fallopian tube, in the ovary, β-netrin protein expression was developmentally regulated. Specifically, β-netrin immunoreactivity was only seen in the basement membrane of the secondary or mature follicles; primary follicles were not reactive with the anti-β-netrin antibody. Similarly, dense alkaline phosphate staining of the localizing RNA transcripts for β-netrin were observed in the large maturing follicles whereas the primary follicles were more lightly stained. Sections assayed for RNA transcripts for a control probe did not label the ovary.

Figure 5:
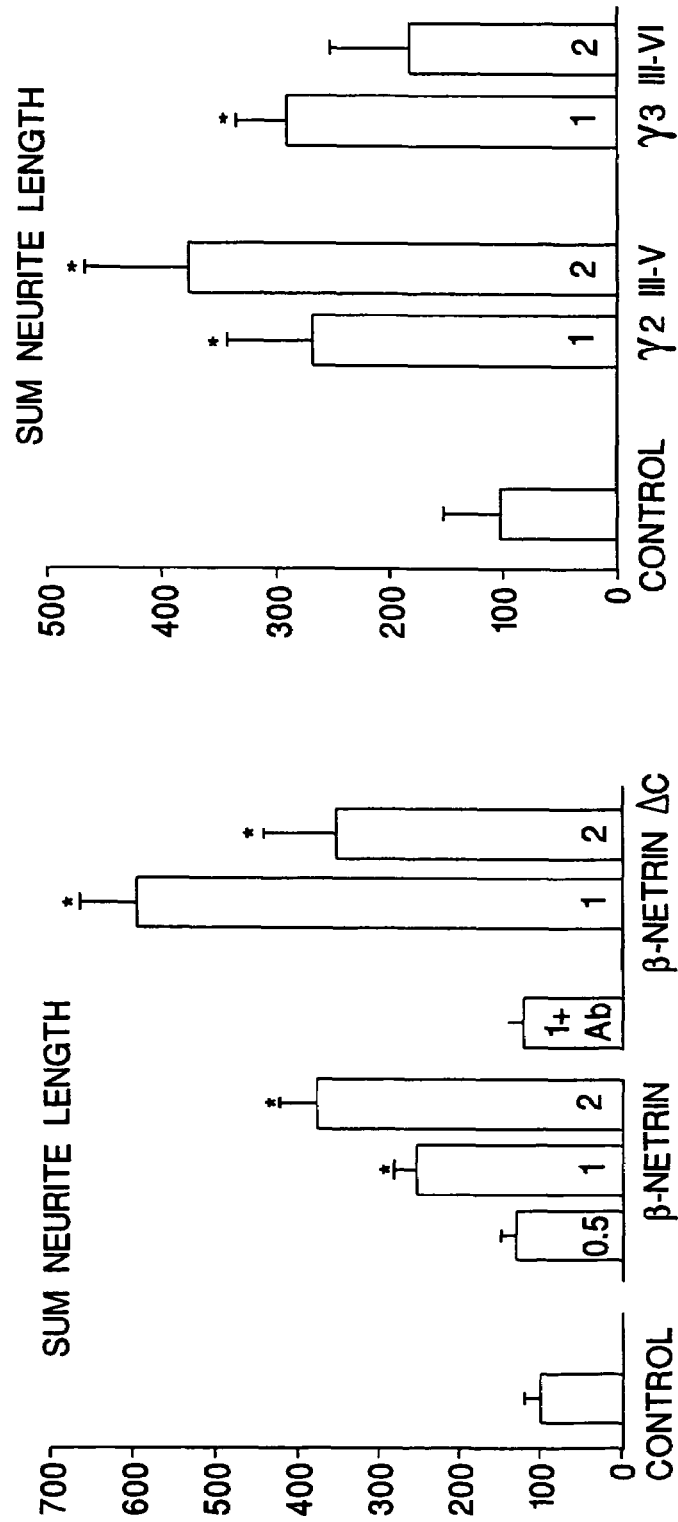
FIG. 5 shows graphs of neurite outgrowth of rat olfactory explants in the presence of β-netrin and the short arms of laminin β2 and β3. The graphs show the summed neurite length as compared to the percent of neurite length of control neurite outgrowth.

Immunoreactivity was also present in the perimysium of the heart where b-netrin is expressed surrounding individual muscle cells; in situ hybridization localizes transcripts to the cardiac wall and the aorta during embryonic development, ED 15.5. β-netrin is prominently expressed in spleen, e.g., in splenocytes (FIG. 5). There appeared to be more reactivity in red pulp than in white.

β-netrin was is not expressed in the developing spinal cord along with netrins 1 and 2 at E11.5 (embryonic day 11.5) to E17.5 mouse embryos and found only diffuse immunoreactivity indistinguishable from control sections whereas Netrin-1 was expressed at high levels in the floor plate; expression levels are above background in the ventricular epithelium to the midpoint of the dorsal-ventral axis and wnt-1 was expressed in a small number of cells in the roofplate.

As RT-PCR showed high levels of expression of β-netrin mRNA in the brain, β-netrin protein expression was studied in this tissue. The protein was observed in the olfactory bulb. In situ hybridization confirmed the presence of β-netrin transcripts within the olfactory bulb; specifically, in the periglomerular cells and the lateral olfactory tract; in addition, the ventricular epithelium showed considerable binding of the β-netrin antisense probes and some expression was detected in the mitral cell layer. Immunohistochemistry demonstrated β-netrin immunoreactivity within the lateral olfactory tract as well as in the perinerium of the vomeronasal nerve; only a weak, diffuse immunoreactivity was seen in the glomeruli of the olfactory bulb. Finally, there was strong deposition of β-netrin immunoreactivity in the basement membranes of the vascular supply of the brain, as well as in capillary beds throughout the brain; β-netrin mRNA was also detected by in situ hybridization in vascular endothelial cells and the choroid plexus at embryonic ages (ED 15.5).

Effects of β-netrin on Tumor Growth and Angiogenesis

β-netrin inhibits tumor growth and angiogenesis in tumors. β-netrin can have a critical role in central nervous system angiogenesis. The human epidermoid carcinoma cell cline A431 was obtained from the ATCC (Rockville Md.). The A431 cells were transfected with a PCEP4 expression vector with no insert and with a PCEP4 vector with the full length β-netrin cDNA insert. Transfected cells were selected with the PCEP4 constructs. The cells were subcloned. Two control lines and one line expressing β-netrin were expanded. Approximately $2 \cdot 10^6$ cells of each cell line were injected intradermally into the flanks of 8 week old female Balb/C (nu/nu) mice. Five mice were used for each cell cone and two sites were used on each mouse. Tumor diameters were measured weekly with digital calipers. The tumor volumes were calculated using the formula:

$$\text{Volume} = \frac{4 \cdot \pi \cdot (0.5 \cdot smaller diameter)^2 \cdot (0.5 \cdot larger diameter)}{3}$$

Mice were sacrificed after 3 weeks or earlier if the largest tumor diameter exceeded 20 mm.

N); values in the presence of all but the lowest concentration of rβ-N were statistically different from control values (p<0.05). The addition of an affinity purified preparation of pooled anti-β-netrin antisera antagonized this effect, reducing neurite length and number to control levels. The parameter most affected by β-netrin addition is the number of neurites produced (Table 1).

TABLE 1

Outgrowth from olfactory bulb explants
Percent of Control

| | Number of Experiments | Number of Explants | Sum neurite Length | Average neurite Length | Neurite Area | Neurites per Circumference | Number of Neurites |
|---|---|---|---|---|---|---|---|
| Control | 24 | 52 | 100 +/− 14 | 100 +/− 4 | 100 +/− 10 | 100 +/− 11 | 100 +/− 11 |
| rβ-netrin | | | | | | | |
| 7 nM | 6 | 11 | 127 +/− 31 | 109 +/− 7 | 143 +/− 23 | 108 +/− 28 | 131 +/− 25 |
| 14 nM | 20 | 41 | 246 +/− 32* | 139 +/− 11* | 160 +/− 8* | 188 +/− 18* | 189 +/− 17* |
| 28 nM | 10 | 16 | 368 +/− 39* | 154 +/− 10* | 197 +/− 25* | 265 +/− 26* | 265 +/− 17* |
| 14 nM + ab | 6 | 12 | 108 +/− 18# | 121 +/− 15 | 112 +/− 18# | 90 +/− 15# | 100 +/− 13# |
| rβ-netrin ΔC | | | | | | | |
| 19 nM | 4 | 8 | 587 +/− 63− | 168 +/− 11* | 235 +/− 18* | 344 +/− 68* | 370 +/− 48* |
| 38 nM | 4 | 8 | 355 +/− 91* | 135 +/− 16 | 136 +/− 26 | 285 +/− 70* | 279 +/− 46* |
| 190 nM | 5 | 15 | 65 +/− 10 | 85 +/− 18 | 64 +/− 18 | 84 +/− 9 | 78 +/− 11 |
| rγ2 | | | | | | | |
| 15 nM | 10 | 20 | 217 +/− 50* | 113 +/− 9 | 136 +/− 25 | 178 +/− 23* | 185 +/− 29* |
| 30 nM | 9 | 24 | 225 +/− 60 | 130 +/− 18 | 139 +/− 26 | 151 +/− 24 | 166 +/− 27 |
| 60 nM | 3 | 8 | 82 +/− 48 | 106 +/− 15 | 65 +/− 31 | 68 +/− 27§ | 91 +/− 53 |
| rγ3 | | | | | | | |
| 9 nM | 0 | 3 | 215 +/− 45* | 122 +/− 14 | 146 +/− 26 | 172 +/− 28* | 177 +/− 28* |
| 18 nM | 10 | 23 | 139 +/− 27 | 102 +/− 5 | 96 +/− 13 | 117 +/− 18 | 140 +/− 24 |
| 36 nM | 2 | 7 | 47 +/− 19§ | 150 +/− 65 | 49 +/− 31§ | 58 +/− 0§ | 42 +/− 32§ |
| rβ2 | | | | | | | |
| 8 nM | 3 | 8 | 65 +/− 14 | 70 +/− 6* | 51 +/− 8* | 99 +/− 22 | 89 +/− 19 |
| 16 nM | 6 | 23 | 124 +/− 12 | 103 +/− 12 | 107 +/− 26 | 132 +/− 34 | 123 +/− 31 |
| 32 nM | 3 | 10 | 188 +/− 77 | 128 +/− 16§ | 192 +/− 81 | 164 +/− 58 | 166 +/− 43 |

*p < 0.05 vs. control
p < 0.05 vs. 7 nM rβ-netrin
§p < 0.05 vs. 15 nM rγ2, 9 nM rγ3, or 8 nM rβ2

Figure 7:
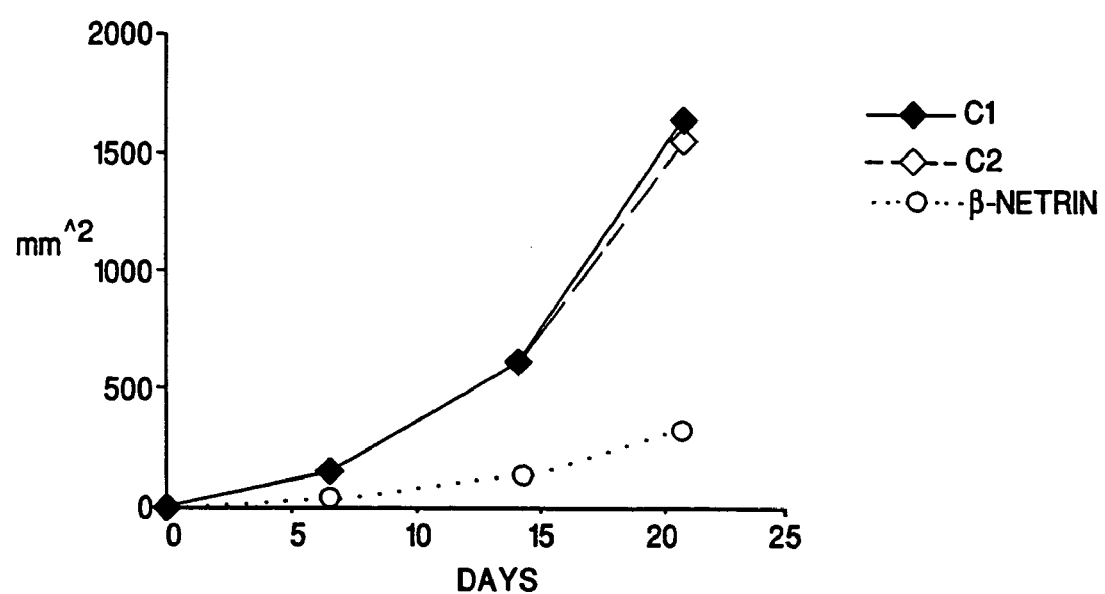
FIG. 7 is a graph of the tumor size against the time in days after injection. The plot of tumors from the cell line transformed with vector alone is show as diamonds, whereas tumors from the cell line transformed with vector with β-netrin insert is shown as open circles.

After twelve days, a large difference in tumor size between control and β-netrin expressing cells was evident. β-netrin expressing tumors were significantly smaller. After 20 days, the β-netrin expressing tumors were less than 15% of the size of control tumors (FIG. 7). Fewer blood vessels supplied the β-netrin expressing tumor relative to control tumors; further the blood vessels present were less bifurcated. β-netrin expressing tumors were encapsulated by a basement membrane which incorporated the expressed β-netrin.

Effects of β-netrin on Neurite Outgrowth

Explants of E15 rat olfactory bulb were dissected, embedded in collagen gels, and incubated with soluble recombinant full length and truncated β-netrin (rβ-N and rβ-NΔC). In control cultures, neurites extend around the circumference of the explant. Treatment with rβ-netrin increased both the neurite length and the number of neurites extending from cultures. Neurite outgrowth was measured by the following parameters: total number of neurites; average neurite length; total length of neurites (sum neurite length); total neurite area (Table 1). By all measures, addition of rβ-N produced an increase in neurite outgrowth. With the addition of rβ-N, there was a dose-dependent increase in both the sum length of all neurites and the number of neurites (normalized to explant circumference) of up to 400% of control measurements (rβ-

The addition of the truncated version of β-netrin missing the C domain, rβ-NΔC, to explants also increased the total neurite length and the number of neurites extending from the explants (FIG. 5). However, with increased concentrations of the truncated form of the molecule, neurite length and number returned to control levels; biphasic responses to netrin application are well documented in the literature (e.g., Serafini et al 1994). Short arm fragments of both laminin γ2 and γ3 chains, as well as similar fragments of the laminin β2 chain were expressed and tested in the system. The addition of recombinant fragments of the laminin γ2 or γ3 chains increased neurite extension, measured either as sum length or number of neurites but both γ chain short arms were slightly less effective at stimulating outgrowth than β-netrin. Interestingly, increasing the dose of added larninin γ chain short arms had decreased efficacy on neurite stimulation, similar to that seen with rβ-NΔC. On the other hand, the short arm fragment of the laminin p2 chain had no statistically significant effect on neurite extension over the concentration range tested.

Chromosomal Localization

β-netrin was localized to human chromosome 12, region q22-q23. Nearby this site are several genes associated with human ovarian cancer. β-netrin cDNA sequences have also shown sequence homology to nucleic acid sequences identified in the dbEST databases which are derived from ovarian and cervical cancers, and multiple sclerosis.

The Netrins are a Family of Laminin-Like Molecules

The netrins are a family of molecules related to the N-termini of laminin chains. Netrins 1-3 all are laminin γ chain-like molecules, whereas the molecule reported here, β-netrin, is structurally related to the laminin β chains. Given that there are three laminin chain isoforms (α, β, and γ), there are likely to be additional members of the netrin family, as there have been no laminin α chain netrin analogs reported as yet. Indeed, two transmembrane domain-containing netrin-like molecules have been identified. These molecules have laminin-like domains VI and V resembling the laminin short arm. These molecules do not have the C-domain of the netrins and thus are a likely to form a novel sub-family. The full identification of these molecules will be reported elsewhere; however, their existence suggests that a large family of laminin short arm related molecules exist and that they are broadly distributed and may have diverse functions beyond the oft-studied axonal guidance properties of the netrins.

Structurally, β-netrin is similar is most respects to the other members of the netrin family. β-netrin was found to form dimers. The rotary-shadowed images are most consistent with dimerization occurring via interactions in the C domain of one molecule with the V domain of its partner, as the VI domains are separated by the approximate length of one, but not two, V and C domains. If β-netrin dimerizes, in vivo, this could have implications for signal transduction. Such dimerization could either cluster β-netrin receptors on individual cells, or it could bridge two cells expressing β-netrin receptors. Indeed, the dimerization of netrin receptors appears to be a critical feature of netrin signaling as the heterodimerization of the Unc5h2 and DCC netrin receptors is necessary and sufficient to convert netrin attraction to repulsion (Hong et al., 1999, *Cell* 97:927-941). Alternatively, the biologically active sites defined as dimerization sites may reduce activity (see below) and the availability of effector binding sites.

Of the previously reported netrins, only two (netrins 1 and 3) have been identified in mouse (Wang et al., 1999, *J Neuroscience* 19:4938-4947; Puschel, 1999, *Mech Dev* 83:65-75); netrin 2 has not. Although much of the work on netrins 1 and 2 has focused on the role of these molecules in neural development, they are widely expressed outside the nervous system. This new member of the family is expressed primarily outside the nervous system, most abundantly in the vasculature, kidney, ovary and heart. Netrin-3 is highly expressed in somatic tissues particularly lung and heart (Wang et al., supra; Puschel, 1999, supra).

Within the nervous system, expression of β-netrin is limited largely to the retina and olfactory bulb. β-netrin is expressed within the CNS vasculature, both in large muscular arteries as well as small capillaries, and in the ventricular ependymal cells. Thus, β-netrin is likely to have an important role in CNS angiogenesis; indeed its expression outside of the nervous system in somatic vasculature supports this suggestion.

β-Netrin is a Basement Membrane Molecule

Three antibody preparations have been produced which reliably detect β-netrin on both blots and tissue sections and have demonstrated where β-netrin protein is deposited. Befitting its origin as a laminin-like molecule, β-netrin is deposited in the basement membranes of a variety of tissues, most prominently the kidney, ovary, heart and vasculature. While the location of a netrin is these regions may be surprising to some, it is not without precedent, as the localization of netrin-1 to the perimeter of the spinal cord in the region of the pia, a basement membrane-like structure in the CNS, has been reported in the chicken (MacLennan et al., 1997, *J Neuroscience* 17:5466-79) seemingly at odds with the chemoattractant hypothesis of netrin action. Specifically, β-netrin is deposited in close apposition to the source of synthesis. For example, β-netrin RNA is expressed in the tubules of the kidney and epithelium of the fallopian tube and β-netrin protein is deposited in the subjacent basement membranes. In situ hybridization on large blood vessels show that β-netrin message is localized to the smooth muscle wall of the vessels, as is β-netrin protein. Smooth muscle has been confirmed as one source of this protein by isolating the protein from supernatants of primary cultures of smooth muscle cells; however, we cannot exclude the endothelium as another source.

The co-localization of β-netrin RNA expression and protein deposition is less consistent with the chemoattractive or chemorepulsive mechanisms which have been suggested for the other netrins. Gradients of protein expression have been postulated for these molecules (Kennedy et al., 1994, *Cell* 78:425-435; Serafini et al., 1994, *Cell* 78:409-24). In the case of netrin-1 such a gradient may exist across the spinal cord, as there is a point source for netrin-1 in the floor plate and netrin-1 protein appears to be localized to the perimeter of the spinal cord and the adjoining pial basement membrane. Thus, given a source (floor plate) and an apparent sink (in the pial basement membrane), there may be a gradient, the grade of which will be determined by the turnover of the molecule at both source and sink. In contrast, in the CNS, β-netrin RNA and β-netrin protein are present in immediately adjacent structures. For example, RNA transcripts are seen in the lateral olfactory tract and protein is deposited there. Thus, there does not appear to be the possibility of a gradient of β-netrin expression; unless it is a very steep one. Nonetheless, β-netrin may be important in axon guidance or pathfinding in the CNS. Disruptions of basement membranes, netrins, ECM elements, and their receptors produce a wide variety of disruptions in axon guidance and neuronal migration. These processes, although conceptually different, may differ formally only by the translocation, or lack thereof, of the nucleus. For example, mutations that disrupt the expression of the basement membrane component, nidogen, in *C. elegans* result in axons that fasciculate properly but grow in the wrong locations (Kim and Wadsworth, 2000, *Science* 288:150-154). The basement membranes traversed by the misdirected axons appeared normal by transmission electron microscopy, and served as substrates for the outgrowth of those axons that were correctly targeted. Therefore, basement membrane components participate directly in determining the pathways of subsets of axons. β-netrin may be another basement membrane component which provides such guidance cues. Functional disruptions of β-netrin using genetic systems or other approaches will resolve this speculation. β-netrin knockout mice have been produced which appear viable.

β-Netrin Affects Neurite Outgrowth

A step in defining the role of β-netrin was taken in this study. The localization of β-netrin within the lateral olfactory tract, and the well-documented ability of netrins to direct neurite outgrowth, prompted us to determine if β-netrin supported neurite extension. Indeed, the addition of purified β-netrin to our culture system promoted neurite elongation. Specifically, the parameter most affected was apparently initiation of elongation, that is, the number of neurites produced, in contrast to any measure of length of neuritis.

This finding suggests that β-netrin is a permissive signal and stimulates neurite elongation. Coupled with the expression data, it suggests that β-netrin acts by stabilizing the extending axons in some way. Since outgrowth frequently occurs by the overgrowth of pioneering axons by secondary axons, perhaps β-netrin is stabilizing the contacts between these jointly growing neurites, contributing to fasciculation. Indeed, β-netrin immunoreactivity is associated with the basal laminae in the perineurium of both the vomeronasal neve and the optic nerve. Alternatively, the incorporation of β-netrin into these basement membranes may contribute a inhibitory boundary function to these structures, similar to what has been proposed for netrin-1 which is localized in the perimeter of the spinal cord (MacLennan et al., supra). However, the stimulatory effect seen upon axon outgrowth from olfactory bulb explants suggests that β-netrin may be functioning in a fashion similar to netrin-1 which is expressed along the optic pathway (Deiner and Sretavan, 1999, *J Neuroscience* 19:9900-12) and disruptions of which disrupt ganglion cell routing (Deiner et al., 1997, *Neuron* 19:575-589).

β-netrin, and the short arm domains of the laminin γ2 and γ3 chains all have similar effects upon axon outgrowth from olfactory bulb explants in vitro. The positive effects of γ2 short arms are particularly informative, as γ2 totally lacks the VI domain and contains only three and one-half EGF-like repeats in domain V. Thus, the γ2 chain and β-netrin share amino acid identity in only the second and third EGF-like repeats of laminin domains V. These findings strongly suggest that the outgrowth activity of β-netrin and of laminins themselves may be mediated by EGF-like repeats within the V domain. In fact, the EGF-like repeat, V-2, is the most highly conserved among the mouse netrins, suggesting that the outgrowth-promoting activity may reside within this region of the molecule. Others have made similar suggestions in *C. elegans* (Wadsworth et al., 1996, *Neuron* 16:35-46) and shown that the C-terminal region is not necessary to rescue the netrin-1 deletion (Lim et al., 1999, *J Neuroscience* 19:7048-7056). It is interesting that while β2 short arm is the molecule with greatest identity to that-of β-netrin, the β2 short arm has no statistically significant effect on neurite extension or elongation, in contrast to other laminin short arms. This is despite a slight trend towards increased neuritogenesis in treated cultures.

Two other points deserve attention. First, all species of molecule applied in our assay inhibited neurite extension if applied at a high concentration. This suggests that response of neurons to laminin short arms and the netrins is biphasic; similar data have been reported for netrin-1 (Serafini et al., 1994; supra). The biphasic response may reflect multiple receptors for these molecules or multiple signal transduction cascade mechanisms. Responses to netrin-1 are complex and can be repulsive as well as attractant for both axons and migrating neurons (Colamarino and Tessier-Lavigne, 1995; *Cell* 81:621-629; Serafini et al., 1994, supra; Kim et al., 1999, *Development* 126:3881-3890; Alcantara et al., 2000, *Development* 127:1359-1372). Second, it is worthy to note that β-netrin lacking the C domain has greater activity in our neurite extension assay on a molar basis than does full length β-netrin. This may reflect the observation that full length, but not truncated βnetrin forms dimmers. In this assay, dimer formation may reduce the apparent activity of β-netrin. In *C. elegans*, while a truncated form of the netrin-1 molecule (unc6ΔC) can rescue the UNC6(-/-) phenotype, it produces aberrant branching (Lim et al., 1999, supra) which might be related to increased activity of truncated form of β-netrin that we have observed in vitro.

β-Netrin May have Significant Roles Outside of the Nervous System

In addition to its expression in the nervous system, β-netrin is deposited around the smooth muscle cells of all somatic muscular arteries, between cardiac myocytes and in the basement membrane of brain capillaries. Together, these data suggest a role for β-netrin in vascular development. Several recent studies document that some molecular species are active in both nervous and vascular development. For example, neuropilin-1 has been shown to be a receptor for vascular endothelial growth factor (VEGF) and to be expressed by endothelial cells (Soker et al., 1998, *Cell* 92:735-745). Mice deficient in neuropilin-1 expression demonstrate vascular insufficiency and disorganization. Similarly, the putative neural guidance molecules, the ephs and ephrins, are expressed in the vascular system. Ephrin-B2 has been found on the surfaces of arteries, but not on veins (Wang et al., 1998, *Cell* 93:741-753), and a complementary expression of its receptor Eph-B4 was found on veins but not arteries. These findings support the concept that these neuroactive signaling molecules may be crucial for morphogenesis of the vascular tree.

Similarly, it is likely that β-netrin functions in both the nervous system and in the vasculature. In both systems, the protein product is near its site of synthesis, suggesting that in both systems β netrin is not instructive in either axonal guidance or vascular development but may be permissive, promoting axonal or vascular development. The localization of β-netrin in basement membranes suggests β-netrin may stabilize growing and mature elements, or provide positive growth cues along established axon or vascular highways.

Treatments

Based upon its localization and upon its structural similarities to netrins, β-netrin plays a role in outgrowth guidance and/or stability of neurites. β-netrin administration or upregulation of its endogenous expression, alone or combination with other molecules, are useful for the regeneration of neurons and for directional outgrowth of neurons. Thus, the β-netrin molecules of the invention can be used to treat neurological disorders, e.g., neurodegenerative disorders, e.g., Alzheimer's, or acute neurological disorders, e.g., mechanical trauma to the nervous system.

β-netrin can be anti-angiogenic. Thus, the β-netrin molecules of the invention or antagonists thereof can be used to inhibit unwanted angiogenesis, e.g., angiogenesis to cancer cells, or promote angiogenesis, e.g., to treat ischemia.

β-netrin production can also be diagnostic of certain cancers, e.g., ovarian, cervical or colorectal cancer, or multiple sclerosis.

Analogs of Beta-Netrin

Analogs can differ from naturally occurring β-netrin in amino acid sequence or in ways that do not involve sequence, or both. Non-sequence modifications include in vivo or in vitro chemical derivatization of β-netrin. Non-sequence modifications include changes in acetylation, methylation, phosphorylation, carboxylation, or glycosylation.

Preferred analogs include β-netrin (or biologically active fragments thereof) whose sequences differ from the wild-type sequence by one or more conservative amino acid substitutions or by one or more non-conservative amino acid substitutions, deletions, or insertions which do not abolish the β-netrin biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from Table 2 below.

TABLE 2

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-fle, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Tbr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

Gene Therapy

The gene constructs of the invention can also be used as a part of a gene therapy protocol to deliver nucleic acids encoding either an agonistic or antagonistic form of a β-netrin polypeptide. The invention features expression vectors for in vivo transfection and expression of a β-netrin polypeptide in particular cell types so as to reconstitute the function of, or alternatively, antagonize the function of a β-netrin polypeptide in a cell in which that polypeptide is misexpressed. Expression constructs of β-netrin polypeptides, may be administered in any biologically effective carrier, e.g. any formulation or composition capable of effectively delivering the β-netrin gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or CaPO$_4$ precipitation carried out in vivo.

A preferred approach for in vivo introduction of nucleic acid into a cell is by use of a viral vector containing nucleic acid, e.g. a cDNA, encoding a β-netrin polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) Blood 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150: 4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 d1324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) *Curr. Topics in Micro. and Immunol.* 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

In addition to viral transfer methods, such as those illustrated above, non-viral methods can also be employed to cause expression of a β-netrin polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject β-netrin gene by the targeted cell. Exemplary gene delivery systems of this type include liposomal derived systems, poly-lysine conjugates, and artificial viral envelopes.

In a representative embodiment, a gene encoding a β-netrin polypeptide can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547-551; PCT publication WO91/06309; Japanese patent application 1047381; and European patent publication EP-A-43075).

In clinical settings, the gene delivery systems for the therapeutic β-netrin gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by Stereotactic injection (e.g. Chen et al. (1994) *PNAS* 91: 3054-3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

Transgenic Animals

The invention provides non-human transgenic animals. Such animals are useful for studying the function and/or activity of a β-netrin protein and for identifying and/or evaluating modulators of β-netrin activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous β-netrin gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a β-netrin protein to particular cells. A transgenic founder animal can be identified based upon the presence of a β-netrin transgene in its genome and/or expression of β-netrin mRNA in tissues or cells of the animals. A transgenic founder animal can then be used to breed additional animals carrying the transgene. Moreover, transgenic animals carrying a transgene encoding a β-netrin protein can further be bred to other transgenic animals carrying other transgenes.

β-netrin proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed herein.

Production of Fragments and Analogs

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Generation of Analogs: Production of Altered DNA and Peptide Sequences by Random Methods Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11-15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp 273-289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386-390; Roberts et al. (1992) *PNAS* 89:2429-2433; Devlin et al. (1990) *Science* 249: 404-406; Cwirla et al. (1990) *PNAS* 87: 6378-6382; as well as U.S. Pat. Nos. 5,223, 409, 5,198,346, and 5,096,815).

Generation of Analogs: Production of Altered DNA and Peptide Sequences by Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1-3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081-1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci.* USA, 75: 5765[1978]).

Cassette Mutagenesis

Another method for preparing variants, cassette mutagenesis, is based on the technique described by Wells et al. (*Gene,* 34:315[1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. For example, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, neurite outgrowth, angiogenesis, and binding to natural ligands or substrates, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid (interaction trap) assays such as the system described above (as with the other screening methods described herein), can be used to identify fragments or analogs (see e.g., U.S. Pat. No. 5,283,317; PCT publication WO94/10300; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). These may include agonists, superagonists, and antagonists. (The subject protein and a protein it interacts with are used as the bait protein and fish proteins.). These assays rely on detecting the reconstitution of a functional transcriptional activator mediated by protein-protein interactions with a bait protein. In particular, these assays make use of chimeric genes which express hybrid proteins. The first hybrid comprises a DNA-binding domain fused to the bait protein. e.g., a β-netrin molecule or a fragment thereof. The second hybrid protein contains a transcriptional activation domain fused to a "fish" protein, e.g. an expression library, e.g., a neural tissue expression library. If the fish and bait proteins are able to interact, they bring into close proximity the DNA-binding and transcriptional activator domains. This proximity is sufficient to cause transcription of a reporter gene which is operably linked to a transcriptional regulatory site which is recognized by the DNA binding domain, and expression of the marker gene can be detected and used to score for the interaction of the bait protein with another protein.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) Bio/Technology 9:1370-1371; and Goward et al. (1992) TIBS 18:136-140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical E. coli filamentous phages M13, fd., and f1 are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) J. Biol. Chem. 267:16007-16010; Griffiths et al. (1993) EMBO J. 12:725-734; Clackson et al. (1991) Nature 352:624-628; and Barbas et al. (1992) PNAS 89:4457-4461).

A common approach uses the maltose receptor of E. coli (the outer membrane protein, LamB) as a peptide fusion partner (Charbit et al. (1986) EMBO 5, 3029-3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) Vaccines 91, pp. 387-392), PhoE (Agterberg, et al. (1990) Gene 88, 37-45), and PAL (Fuchs et al. (1991) Bio/Tech 9, 1369-1372), as well as large bacterial surface structures have served as vehicles for peptide display. Peptides can be fused to pilin, a protein which polymerizes to form the pilus-a conduit for interbacterial exchange of genetic information (Thiry et al. (1989) Appl. Environ. Microbiol. 55, 984-993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) Bio/Tech. 6, 1080-1083). Surface proteins of other bacterial species have also served as peptide fusion partners. Examples include the Staphylococcus protein A and the outer membrane protease IgA of Neisseria (Hansson et al. (1992) J. Bacteriol. 174, 4239-4245 and Klauser et al. (1990) EMBO J. 9, 1991-1999).

In the filamentous phage systems and the LamB system described above, the physical link between the peptide and its encoding DNA occurs by the containment of the DNA within a particle (cell or phage) that carries the peptide on its surface.

Capturing the peptide captures the particle and the DNA within. An alternative scheme uses the DNA-binding protein LacI to form a link between peptide and DNA (Cull et al. (1992) *PNAS USA* 89:1865-1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89-1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378-6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med. Chem.* 37(9):1233-1251). These particular biases are not a factor in the Lac display system.

The number of small peptides available in recombinant random libraries is enormous. Libraries of $10^7$-$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3-6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233-1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204, 357-364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of interest is identified, it is routine to perform for one skilled in the art to obtain analogs and fragments.

Peptide Mimetics

The invention also provides for reduction of the protein binding domains of the subject β-netrin polypeptides to generate mimetics, e.g. peptide or non-peptide agents. See, for example, "Peptide inhibitors of human papillomavirus protein binding to retinoblastoma gene protein" European patent applications EP-412,762A and EP-B31,080A.

Non-hydrolyzable peptide analogs of critical residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), 13-turn dipeptide cores (Nagai et al. (1985) *Tetrahedron Lett* 26:647; and Sato et al. (1986) *J Chem Soc Perkin Trans* 1:1231),and β-aminoalcohols (Gordon et al. (1985) *Biochem Biophys Res Commun* 126:419; and Dann et al. (1986) *Biochem Biophys Res Commun* 134:71).

Antibodies

The invention also includes antibodies specifically reactive with a subject β-netrin polypeptide. Anti-protein/anti-peptide antisera or monoclonal antibodies can be made as described herein by using standard protocols (See, for example, *Antibodies: A Laboratory Manual* ed. by Harlow and Lane (Cold Spring Harbor Press: 1988)).

Antibodies which specifically bind β-netrin epitopes can also be used in immunohistochemical staining of tissue samples in order to evaluate the abundance and pattern of expression of β-netrin. Anti β-netrin antibodies can be used diagnostically in immuno-precipitation and immuno-blotting to detect and evaluate β-netrin levels in tissue or bodily fluid as part of a clinical testing procedure.

Another application of antibodies of the present invention is in the immunological screening of cDNA libraries constructed in expression vectors such as λgt11, λgt18-23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a subject polypeptide can then be detected with antibodies, as, for example, reacting nitrocellulose filters lifted from infected plates with antibodies of the invention. Phage, scored by this assay, can then be isolated from the infected plate. Thus, the presence of homologs can be detected and cloned from other animals, and alternate isoforms (including splicing variants) can be detected and cloned from human sources.

Antisense Nucleic Acid Molecules, Ribozymes and Modified Beta-Netrin Nucleic Acid Molecules In another aspect, the invention features, an isolated nucleic acid molecule which is antisense to β-netrin. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire β-netrin coding strand, or to only a portion thereof (e.g., the coding region of human β-netrin). In another embodiment, the antisense nucleic acid molecule is antisense to a "noncoding region" of the coding strand of a nucleotide sequence encoding β-netrin (e.g., the 5' and 3' untranslated regions).

An antisense nucleic acid can be designed such that it is complementary to the entire coding region of β-netrin mRNA, but more preferably is an oligonucleotide which is antisense to only a portion of the coding or noncoding region of β-netrin mRNA. For example, the antisense oligonucleotide can be complementary to the region surrounding the translation start site of β-netrin mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a β-netrin protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. A ribozyme having specificity for a β-netrin-encoding nucleic acid can include one or more sequences complementary to the nucleotide sequence of a β-netrin cDNA disclosed herein and a sequence having known catalytic sequence responsible for mRNA cleavage (see U.S. Pat. No. 5,093,246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a beta-netrin-encoding mRNA. See, e.g., Cech et al. U.S. Pat. No. 4,987,071; and Cech et al. U.S. Pat. No. 5,116,742. Alternatively, beta-netrin mRNA can be used to select a catalytic RNA having a specific ribonuclease activity from a pool of RNA molecules. See, e.g., Bartel, D. and Szostak, J. W. (1993) *Science* 261:1411-1418.

β-netrin gene expression can be inhibited by targeting nucleotide sequences complementary to the regulatory region of the β-netrin (e.g., the β-netrin promoter and/or enhancers) to form triple helical structures that prevent transcription of the β-netrin gene in target cells. See generally, Helene, C. (1991) *Anticancer Drug Des.* 6(6):569-84; Helene, C. et al. (1992) *Ann. N.Y. Acad. Sci.* 660:27-36; and Maher, L. J. (1992) *Bioassays* 14(12):807-15. The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A β-netrin nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) Bioorganic & Medicinal Chemistry 4 (1): 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670-675.

PNAs of β-netrin nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of β-netrin nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) Bio-Techniques 6:958-976) or intercalating agents. (See, e.g., Zon (1988) Pharm. Res. 5:539-549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a β-netrin nucleic acid of the invention, two complementary regions one having a fluorophore and one a quencher such that the molecular beacon is useful for quantitating the presence of the β-netrin nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

β-netrin Chimeric or Fusion Proteins

In another aspect, the invention provides β-netrin chimeric or fusion proteins. As used herein, a β-netrin "chimeric protein" or "fusion protein" includes a β-netrin polypeptide linked to a non-β-netrin polypeptide. A "non-β-netrin polypeptide" refers to a polypeptide having an amino acid sequence corresponding to a protein which is not substantially homologous to the β-netrin protein, e.g., a protein which is different from the β-netrin protein and which is derived from the same or a different organism. The β-netrin polypeptide of the fusion protein can correspond to all or a portion e.g., a fragment described herein of a β-netrin amino acid sequence. In a preferred embodiment, a β-netrin fusion protein includes at least one (or two) biologically active portion of a β-netrin protein. The non-β-netrin polypeptide can be fused to the N-terminus or C-terminus of the β-netrin polypeptide.

The fusion protein can include a moiety which has a high affinity for a ligand. For example, the fusion protein can be a GST-β-netrin fusion protein in which the β-netrin sequences are fused to the C-terminus of the GST sequences. Such fusion proteins can facilitate the purification of recombinant β-netrin. Alternatively, the fusion protein can be a β-netrin protein containing a heterologous signal sequence at its N-terminus. In certain host cells (e.g., mammalian host cells), expression and/or secretion of β-netrin can be increased through use of a heterologous signal sequence.

Fusion proteins can include all or a part of a serum protein, e.g., an IgG constant region, or human serum albumin.

The β-netrin fusion proteins of the invention can be incorporated into pharmaceutical compositions and administered to a subject in vivo. The β-netrin fusion proteins can be used to affect the bioavailability of a β-netrin substrate. β-netrin fusion proteins may be useful therapeutically for the treatment of disorders caused by, for example, (i) aberrant modification or mutation of a gene encoding a β-netrin protein; (ii) mis-regulation of the β-netrin gene; and (iii) aberrant post-translational modification of a β-netrin protein.

Moreover, the β-netrin-fusion proteins of the invention can be used as immunogens to produce anti-β-netrin antibodies in a subject, to purify β-netrin ligands and in screening assays to identify molecules which inhibit the interaction of β-netrin with a β-netrin substrate.

Expression vectors are commercially available that already encode a fusion moiety (e.g., a GST polypeptide). A β-netrin-encoding nucleic acid can be cloned into such an expression vector such that the fusion moiety is linked in-frame to the β-netrin protein.

Variants of β-netrin Proteins

In another aspect, the invention also features a variant of a β-netrin polypeptide, e.g., which functions as an agonist (mimetics) or as an antagonist. Variants of the β-netrin proteins can be generated by mutagenesis, e.g., discrete point mutation, the insertion or deletion of sequences or the truncation of a β-netrin protein. An agonist of the β-netrin proteins can retain substantially the same, or a subset, of the biological activities of the naturally occurring form of a β-netrin protein. An antagonist of a β-netrin protein can inhibit one or more of the activities of the naturally occurring form of the β-netrin protein by, for example, competitively modulating a β-netrin-mediated activity of a β-netrin protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the β-netrin protein.

Variants of a β-netrin protein can be identified by screening combinatorial libraries of mutants, e.g., truncation mutants, of a β-netrin protein for agonist or antagonist activity.

Libraries of fragments e.g., N terminal, C terminal, or internal fragments, of a netrin protein coding sequence can be used to generate a variegated population of fragments for screening and subsequent selection of variants of a β-netrin protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify β-netrin variants (Arkin and Yourvan (1992) *Proc. Natl. Acad. Sci. USA* 89:7811-7815; Delgrave et al. (1993) *Protein Engineering* 6(3):327-331).

Cell based assays can be exploited to analyze a variegated β-netrin library. For example, a library of expression vectors can be transfected into a cell line, e.g., a cell line, which ordinarily responds to β-netrin in a substrate-dependent manner. The transfected cells are then contacted with β-netrin and the effect of the expression of the mutant on signaling by the β-netrin substrate can be detected, e.g., by measuring β-netrin activity. Plasmid DNA can then be recovered from the cells which score for inhibition, or alternatively, potentiation of signaling by the β-netrin substrate, and the individual clones further characterized.

In another aspect, the invention features a method of making a β-netrin polypeptide, e.g., a peptide having a non-wild type activity, e.g., an antagonist, agonist, or super agonist of a naturally occurring β-netrin polypeptide, e.g., a naturally occurring β-netrin polypeptide. The method includes: altering the sequence of a β-netrin polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a β-netrin polypeptide a biological activity of a naturally occurring beta-netrin polypeptide. The method includes: altering the sequence, e.g., by substitution or deletion of one or more residues, of a β-netrin polypeptide, e.g., altering the sequence of a non-conserved region, or a domain or residue described herein, and testing the altered polypeptide for the desired activity.

Informatics

The sequence of a beta-netrin molecule is provided in a variety of media to facilitate use thereof. A sequence can be provided as a manufacture, other than an isolated nucleic acid or amino acid molecule, which contains a beta-netrin. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, beta-netrin full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device. As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network).

Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing beta-netrin, e.g., analyzing structure, function, or relatedness to one or more other nucleic acid or amino acid sequences. The method includes: providing a beta-netrin nucleic acid or amino acid sequence; comparing the beta-netrin sequence with a second sequence, e.g., one or more preferably a plurality of sequences from a collection of sequences, e.g., a nucleic acid or protein sequence database to thereby analyze beta-netrin. The method can be performed in a machine, e.g., a computer, or manually by a skilled artisan.

The method can include evaluating the sequence identity between a beta-netrin sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a beta-netrin sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features a method of analyzing a sequence. The method includes: providing a beta-netrin sequence, or record, in machine-readable form comparing a second sequence to the beta-netrin sequence; thereby analyzing a sequence Comparison can include comparing to sequences for sequence identity or determining if one sequence is included within the other, e.g., determining if the beta-netrin sequence includes a sequence being compared. In a preferred embodiment the beta-netrin or second sequence is stored on a first computer, e.g., at a first site and the comparison is performed, read, or recorded on a second computer, e.g., at a second site. E.g., the beta-netrin or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region In another aspect, the invention provides a machine-readable medium for holding instructions for performing a method for determining whether a subject has a beta-netrin-associated disease or disorder or a pre-disposition to a beta-netrin-associated disease or disorder, wherein the method comprises the steps of determining beta-netrin sequence information associated with the subject and based on the beta-netrin sequence information, determining whether the subject has a beta-netrin-associated disease or disorder or a pre-disposition to a beta-netrin-associated disease or disorder and/or recommending a particular treatment for the disease, disorder or pre-disease condition.

The invention further provides in an electronic system and/or in a network, a method for determining whether a subject has a beta-netrin-associated disease or disorder or a pre-disposition to a disease associated with a beta-netrin wherein the method comprises the steps of determining beta-netrin sequence information associated with the subject, and based on the beta-netrin sequence information, determining whether the subject has a beta-netrin-associated disease or disorder or a pre-disposition to a beta-netrin-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the beta-netrin sequence of the subject to the beta-netrin sequences in the database to thereby determine whether the subject as a beta-netrin-associated disease or disorder, or a pre-disposition for such.

The present invention also provides in a network, a method for determining whether a subject has a beta-netrin associated disease or disorder or a pre-disposition to a beta-netrin-associated disease or disorder associated with beta-netrin, said method comprising the steps of receiving beta-netrin sequence information from the subject and/or information related thereto, receiving phenotypic information associated with the subject, acquiring information from the network corresponding to beta-netrin and/or corresponding to a beta-netrin-associated disease or disorder (e.g., a beta-netrin-mediated disorder as described herein), and based on one or more of the phenotypic information, the beta-netrin information (e.g., sequence information and/or information related thereto), and the acquired information, determining whether the subject has a beta-netrin-associated disease or disorder or a pre-disposition to a beta-netrin-associated disease or disorder. The method may further comprise the step of recommending a particular treatment for the disease, disorder or pre-disease condition.

The present invention also provides a method for determining whether a subject has a beta-netrin-associated disease or disorder or a pre-disposition to a beta-netrin-associated disease or disorder, said method comprising the steps of receiving information related to beta-netrin (e.g., sequence information and/or information related thereto), receiving phenotypic information associated with the subject, acquiring information from the network related to beta-netrin and/or related to a beta-netrin-associated disease or disorder, and based on one or more of the phenotypic information, the beta-netrin information, and the acquired information, determining whether the subject has a beta-netrin-associated disease or disorder or a pre-disposition to a beta-netrin-associated disease or disorder. The method may further comprise the step of recommending a particular treatment for the disease, disorder or pre-disease condition.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express a beta-netrin protein (e.g., via a recombinant expression vector in a host cell in gene therapy applications), to detect a beta-netrin mRNA (e.g., in a biological sample) or a genetic alteration in a beta-netrin gene, and to modulate beta-netrin activity, as described further below. The beta-netrin proteins can be used to treat disorders characterized by insufficient or excessive production of a beta-netrin substrate or production of beta-netrin inhibitors. In addition, the beta-netrin proteins can be used to screen for naturally occurring beta-netrin substrates, to screen for drugs or compounds which modulate beta-netrin activity, as well as to treat disorders characterized by insufficient or excessive production of beta-netrin protein or production of beta-netrin protein forms which have decreased, aberrant or unwanted activity compared to beta-netrin wild type protein. Such disorders include those characterized by aberrant signaling or aberrant, e.g., hyperproliferative, cell growth. Moreover, the anti-beta-netrin antibodies of the invention can be used to detect and isolate beta-netrin proteins, regulate the bioavailability of beta-netrin proteins, and modulate beta-netrin activity.

A method of evaluating a compound for the ability to interact with, e.g., bind, a subject beta-netrin polypeptide is provided. The method includes: contacting the compound with the subject beta-netrin polypeptide; and evaluating ability of the compound to interact with, e.g., to bind or form a complex with the subject beta-netrin polypeptide. This method can be performed in vitro, e.g., in a cell free system, or in vivo, e.g., in a two-hybrid interaction trap assay. This method can be used to identify naturally occurring molecules which interact with subject beta-netrin polypeptide. It can also be used to find natural or synthetic inhibitors of subject beta-netrin polypeptide. Screening methods are discussed in more detail below.

Screening Assays:

The invention provides methods (also referred to herein as "screening assays") for identifying modulators, i.e., candidate or test compounds or agents (e.g., proteins, peptides, peptidomimetics, peptoids, small molecules or other drugs) which bind to beta-netrin proteins, have a stimulatory or inhibitory effect on, for example, beta-netrin expression or beta-netrin activity, or have a stimulatory or inhibitory effect on, for example, the expression or activity of a beta-netrin substrate. Compounds thus identified can be used to modulate the activity of target gene products (e.g., beta-netrin genes) in a therapeutic protocol, to elaborate the biological function of the target gene product, or to identify compounds that disrupt normal target gene interactions.

In one embodiment, the invention provides assays for screening candidate or test compounds which are substrates of a beta-netrin protein or polypeptide or a biologically active portion thereof. In another embodiment, the invention provides assays for screening candidate or test compounds which bind to or modulate the activity of a beta-netrin protein or polypeptide or a biologically active portion thereof.

The test compounds of the present invention can be obtained using any of the numerous approaches in combinatorial library methods known in the art, including: biological libraries; peptoid libraries [libraries of molecules having the functionalities of peptides, but with a novel, non-peptide backbone which are resistant to enzymatic degradation but which nevertheless remain bioactive] (see, e.g., Zuckermann, R. N. et al. *J. Med. Chem.* 1994, 37: 2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a cell-based assay in which a cell which expresses a beta-netrin protein or biologically active portion thereof is contacted with a test compound, and the ability of the test compound to modulate beta-netrin activity is determined. Determining the ability of the test compound to modulate beta-netrin activity can be accomplished by monitoring, for example, β-netrin activity, e.g., promotion of axonal or vascular development. The cell, for example, can be of mammalian origin, e.g., human.

The ability of the test compound to modulate beta-netrin binding to a compound, e.g., a beta-netrin substrate, or to bind to beta-netrin can also be evaluated. This can be accomplished, for example, by coupling the compound, e.g., the substrate, with a radioisotope or enzymatic label such that binding of the compound, e.g., the substrate, to beta-netrin can be determined by detecting the labeled compound, e.g., substrate, in a complex. Alternatively, beta-netrin could be coupled with a radioisotope or enzymatic label to monitor the ability of a test compound to modulate beta-netrin binding to a beta-netrin substrate in a complex. For example, compounds (e.g., beta-netrin substrates) can be labeled with $^{125}$I, $^{35}$S, $^{14}$C, or $^3$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a beta-netrin substrate) to interact with beta-netrin with or without the labeling of any of the interactants can be evaluated. For example, a microphysiometer can be used to detect the interaction of a compound with beta-netrin without the labeling of either the compound or the beta-netrin. McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and beta-netrin.

In yet another embodiment, a cell-free assay is provided in which a beta-netrin protein or biologically active portion thereof is contacted with a test compound and the ability of the test compound to bind to the beta-netrin protein or biologically active portion thereof is evaluated. Preferred biologically active portions of the beta-netrin proteins to be used in assays of the present invention include fragments which participate in interactions with non-beta-netrin molecules, e.g., fragments with high surface probability scores.

Soluble and/or membrane-bound forms of isolated proteins (e.g., beta-netrin proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPS O), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

In one embodiment, assays are performed where the ability of an agent to modulate or promote axonal or vascular development is evaluated.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the beta-netrin protein to bind to a target molecule can be accomplished using real-time Biomolecular Interaction Analysis (BLA) (see, e.g., Sjolander, S, and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either beta-netrin, an anti beta-netrin antibody or its target molecule to facilitate separation of complexed from uncomplexed forms of one or both of the proteins, as well as to accommodate automation of the assay. Binding of a test compound to a beta-netrin protein, or interaction of a beta-netrin protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/beta-netrin fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or beta-netrin protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of beta-netrin binding or activity determined using standard techniques.

Other techniques for immobilizing either a beta-netrin protein or a target molecule on matrices include using conjugation of biotin and streptavidin. Biotinylated beta-netrin protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with beta-netrin protein or target molecules but which do not interfere with binding of the beta-netrin protein to its target molecule. Such antibodies can be derivatized to the wells of the plate, and unbound target or beta-netrin protein trapped in the wells by antibody conjugation. Methods for detecting such complexes, in addition to those described above for the GST-immobilized complexes, include immunodetection of complexes using antibodies reactive with the beta-netrin protein or target molecule, as well as enzyme-linked assays which rely on detecting an enzymatic activity associated with the beta-netrin protein or target molecule.

Alternatively, cell free assays can be conducted in a liquid phase. In such an assay, the reaction products are separated from unreacted components, by any of a number of standard techniques, including but not limited to: differential centrifigation (see, for example, Rivas, G., and Minton, A. P., *Trends Biochem Sci* 1993 Aug.; 18(8):284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard, N. H., *J Mol Recognit* 1998 Winter; 11(1-6):141-8; Hage, D. S., and Tweed, S. A. *J Chromatogr B Biomed Sci Appl* 1997 Oct. 10;699(1-2):499-525). Further, fluorescence energy transfer may also be conveniently utilized, as described herein, to detect binding without further purification of the complex from solution.

In a preferred embodiment, the assay includes contacting the beta-netrin protein or biologically active portion thereof with a known compound which binds beta-netrin to form an assay mixture, contacting the assay mixture with a test compound, and determining the ability of the test compound to interact with a beta-netrin protein, wherein determining the ability of the test compound to interact with a beta-netrin protein includes determining the ability of the test compound to preferentially bind to beta-netrin or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the beta-netrin genes herein identified. In an alternative embodiment, the invention provides methods for determining the ability of the test compound to modulate the activity of a beta-netrin protein through modulation of the activity of a downstream effector of a beta-netrin target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), e.g., a substrate, a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the beta-netrin proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with beta-netrin ("beta-netrin-binding proteins" or "beta-netrin-bp") and are involved in beta-netrin activity. Such beta-netrin-bps can be activators or inhibitors of signals by the beta-netrin proteins or beta-netrin targets as, for example, downstream elements of a beta-netrin-mediated signaling pathway.

The two-hybrid system is based on the modular nature of most transcription factors, which consist of separable DNA-binding and activation domains. Briefly, the assay utilizes two different DNA constructs. In one construct, the gene that codes for a beta-netrin protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: beta-netrin protein can be the fused to the activator domain.) If the "bait" and the "prey" proteins are able to interact, in vivo, forming a beta-netrin-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the beta-netrin protein.

In another embodiment, modulators of beta-netrin expression are identified. For example, a cell or cell free mixture is contacted with a candidate compound and the expression of beta-netrin mRNA or protein evaluated relative to the level of expression of beta-netrin mRNA or protein in the absence of the candidate compound. When expression of beta-netrin mRNA or protein is greater in the presence of the candidate compound than in its absence, the candidate compound is identified as a stimulator of beta-netrin mRNA or protein expression. Alternatively, when expression of beta-netrin mRNA or protein is less (statistically significantly less) in the presence of the candidate compound than in its absence, the candidate compound is identified as an inhibitor of beta-netrin mRNA or protein expression. The level of beta-netrin mRNA or protein expression can be determined by methods described herein for detecting beta-netrin mRNA or protein.

In another aspect, the invention pertains to a combination of two or more of the assays described herein. For example, a modulating agent can be identified using a cell-based or a cell free assay, and the ability of the agent to modulate the activity of a beta-netrin protein can be confirmed in vivo, e.g., in an animal.

This invention further pertains to residues 203-219 (SEQ ID NO:2), novel agents identified by the above-described screening assays. Accordingly, it is within the scope of this invention to further use an agent identified as described herein (e.g., a beta-netrin modulating agent, an antisense beta-netrin nucleic acid molecule, a beta-netrin-specific antibody, or a beta-netrin-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate beta-netrin with a disease; (ii) identify an individual from a minute biological sample (tissue typing); and (iii) aid in forensic identification of a biological sample. These applications are described in the subsections below.

Chromosome Mapping

The beta-netrin nucleotide sequences or portions thereof can be used to map the location of the beta-netrin genes on a chromosome. This process is called chromosome mapping. Chromosome mapping is useful in correlating the beta-netrin sequences with genes associated with disease.

Briefly, beta-netrin genes can be mapped to chromosomes by preparing PCR primers (preferably 15-25 bp in length) from the beta-netrin nucleotide sequences. These primers can then be used for PCR screening of somatic cell hybrids containing individual human chromosomes. Only those hybrids containing the human gene corresponding to the beta-netrin sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919-924).

Other mapping strategies e.g., in situ hybridization (described in Fan, Y. et al. (1990) *Proc. Natl. Acad. Sci. USA*, 87:6223-27), pre-screening with labeled flow-sorted chromosomes, and pre-selection by hybridization to chromosome specific cDNA libraries can be used to map beta-netrin to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783-787.

Moreover, differences in the DNA sequences between individuals affected and unaffected with a disease associated with the beta-netrin gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing beta-netrin sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the beta-netrin nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers which each yield a noncoding amplified sequence of 100 bases. If predicted coding sequences are used, a more appropriate number of primers for positive individual identification would be 500-2,000.

If a panel of reagents from beta-netrin nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial beta-netrin Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use.

The beta-netrin nucleotide sequences described herein can further be used to provide polynucleotide reagents, e.g., labeled or labelable probes which can be used in, for example, an in situ hybridization technique, to identify a specific tissue, e.g., a tissue containing B-netrin activity. This can be very useful in cases where a forensic pathologist is presented with a tissue of unknown origin. Panels of such beta-netrin probes can be used to identify tissue by species and/or by organ type.

In a similar fashion, these reagents, e.g., beta-netrin primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes beta-netrin.

Such disorders include, e.g., a disorder associated with the misexpression of beta-netrin.

The method includes one or more of the following:

detecting, in a tissue of the subject, the presence or absence of a mutation which affects the expression of the beta-netrin gene, or detecting the presence or absence of a mutation in a region which controls the expression of the gene, e.g., a mutation in the 5' control region;

detecting, in a tissue of the subject, the presence or absence of a mutation which alters the structure of the beta-netrin gene;

detecting, in a tissue of the subject, the misexpression of the beta-netrin gene, at the mRNA level, e.g., detecting a non-wild type level of a mRNA;

detecting, in a tissue of the subject, the misexpression of the gene, at the protein level, e.g., detecting a non-wild type level of a beta-netrin polypeptide.

In preferred embodiments the method includes: ascertaining the existence of at least one of: a deletion of one or more nucleotides from the beta-netrin gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from the beta netrin nucleotide sequence, or naturally occurring mutants thereof or 5' or 3' flanking sequences naturally associated with the beta-netrin gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the beta-netrin gene; the presence of a non-wild type splicing pattern of a messenger RNA transcript of the gene; or a non-wild type level of beta-netrin.

Methods of the invention can be used prenatally or to determine if a subject's offspring will be at risk for a disorder.

In preferred embodiments the method includes determining the structure of a beta-netrin gene, an abnormal structure being indicative of risk for the disorder.

In preferred embodiments the method includes contacting a sample form the subject with an antibody to the beta-netrin protein or a nucleic acid, which hybridizes specifically with the gene. There and other embodiments are discussed below.

Diagnostic and Prognostic Assays

Diagnostic and prognostic assays of the invention include method for assessing the expression level of β-netrin molecules and for identifying variations and mutations in the sequence of β-netrin molecules.

Expression Monitoring and Profiling

The presence, level, or absence of a beta-netrin protein or nucleic acid in a biological sample can be evaluated by obtaining a biological sample from a test subject and contacting the biological sample with a compound or an agent capable of detecting beta-netrin protein or nucleic acid (e.g., mRNA, genomic DNA) that encodes beta-netrin protein such that the presence of beta-netrin protein or nucleic acid is detected in the biological sample. The term "biological sample" includes tissues, cells and biological fluids isolated from a subject, as well as tissues, cells and fluids present within a subject. A preferred biological sample is serum. The level of expression of the beta-netrin gene can be measured in a number of ways, including, but not limited to: measuring the mRNA encoded by the beta-netrin genes; measuring the amount of protein encoded by the beta-netrin genes; or measuring the activity of the protein encoded by the beta-netrin genes.

The level of mRNA corresponding to the beta-netrin gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length beta-netrin nucleic acid, such as the nucleic acid of SEQ ID NO:1, or a portion thereof, such as an oligonucleotide of at least 7, 15, 30, 50, 100, 250 or 500 nucleotides in length and sufficient to specifically hybridize under stringent conditions to beta-netrin mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. The probe can be disposed on an address of an array, e.g., an array described below. A skilled artisan can adapt known mRNA detection methods for use in detecting the level of mRNA encoded by the beta-netrin genes.

The level of mRNA in a sample that is encoded by one of beta-netrin can be evaluated with nucleic acid amplification, e.g., by rtPCR (Mullis, 1987, U.S. Pat. No. 4,683,202), ligase chain reaction (Barany, 1991, Proc. Natl. Acad. Sci. USA 88:189-193), self sustained sequence replication (Guatelli et al., 1990, Proc. Natl. Acad. Sci. USA 87:1874-1878), transcriptional amplification system (Kwoh et al., 1989, Proc. Natl. Acad. Sci. USA 86:1173-1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the beta-netrin gene being analyzed.

In another embodiment, the methods further contacting a control sample with a compound or agent capable of detecting beta-netrin mRNA, or genomic DNA, and comparing the presence of beta-netrin mRNA or genomic DNA in the control sample with the presence of beta-netrin mRNA or genomic DNA in the test sample.

A variety of methods can be used to determine the level of protein encoded by beta-netrin. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect beta-netrin protein in a biological sample in vitro as well as in vivo. In vitro techniques for detection of beta-netrin protein include enzyme linked immunosorbent assays (ELISAs), immunoprecipitations, immunofluorescence, enzyme immunoassay (EIA), radioimmunoassay (RIA), and Western blot analysis. In vivo techniques for detection of beta-netrin protein include introducing into a subject a labeled anti-beta-netrin antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-beta-netrin antibody positioned on an antibody array (as described below). The sample can be detected, e.g., with avidin coupled to a fluorescent label.

In another embodiment, the methods further include contacting the control sample with a compound or agent capable of detecting beta-netrin protein, and comparing the presence of beta-netrin protein in the control sample with the presence of beta-netrin protein in the test sample.

The invention also includes kits for detecting the presence of beta-netrin in a biological sample. For example, the kit can include a compound or agent capable of detecting beta-netrin protein or mRNA in a biological sample; and a standard. The compound or agent can be packaged in a suitable container. The kit can further comprise instructions for using the kit to detect beta-netrin protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted beta-netrin expression or activity. As used herein, the term "unwanted" includes an unwanted phenomenon involved in a biological response such as pain or deregulated cell proliferation.

In one embodiment, a disease or disorder associated with aberrant or unwanted beta-netrin expression or activity is identified. A test sample is obtained from a subject and beta-netrin protein or nucleic acid (e.g., mRNA or genomic DNA) is evaluated, wherein the level, e.g., the presence or absence, of beta-netrin protein or nucleic acid is diagnostic for a subject having or at risk of developing a disease or disorder associated with aberrant or unwanted beta-netrin expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted beta-netrin expression or activity. For example, such methods can be used to determine whether a subject can be effectively treated with an agent that modulates beta-netrin expression or activity.

In another aspect, the invention features a computer medium having a plurality of digitally encoded data records. Each data record includes a value representing the level of expression of beta-netrin in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than beta-netrin (e.g., other genes associated with a beta-netrin-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of beta-netrin expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a DISORDERA disorder in a subject wherein an increase in beta-netrin expression is an indication that the subject has or is disposed to having a disorders as described herein. The method can be used to monitor a treatment for such disorders in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of beta-netrin expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an un-contacted cell.

In another aspect, the invention features a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of beta-netrin expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of beta-netrin expression.

Arrays and Uses Thereof

In another aspect, the invention features an array that includes a substrate having a plurality of addresses. At least one address of the plurality includes a capture probe that binds specifically to a beta-netrin molecule (e.g., a beta-netrin nucleic acid or a beta-netrin polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a beta-netrin nucleic acid, e.g., the sense or anti-sense strand. In one preferred embodiment, a subset of addresses of the plurality of addresses has a nucleic acid capture probe for beta-netrin. Each address of the subset can include a capture probe that hybridizes to a different region of a beta-netrin nucleic acid. In another preferred embodiment, addresses of the subset include a capture probe for a beta-netrin nucleic acid. Each address of the subset is unique, overlapping, and complementary to a different variant of beta-netrin (e.g., an allelic variant, or all possible hypothetical variants). The array can be used to sequence beta-netrin by hybridization (see, e.g., U.S. Pat. No. 5,695,940).

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a beta-netrin polypeptide or fragment thereof. The polypeptide can be a naturally-occurring interaction partner of beta-netrin polypeptide. Preferably, the polypeptide is an antibody, e.g., an antibody described herein (see "Anti-beta-netrin Antibodies," above), such as a monoclonal antibody or a single-chain antibody.

In another aspect, the invention features a method of analyzing the expression of beta-netrin. The method includes providing an array as described above; contacting the array with a sample and detecting binding of a beta-netrin-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of beta-netrin. If a sufficient number of diverse samples is analyzed, clustering (e.g., hierarchical clustering, k-means clustering, Bayesian clustering and the like) can be used to identify other genes which are co-regulated with beta-netrin. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on beta-netrin expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a beta-netrin-associated disease or disorder; and processes, such as a cellular transformation associated with a beta-netrin-associated disease or disorder. The method can also evaluate the treatment and/or progression of a beta-netrin-associated disease or disorder The array is also useful for ascertaining differential expression patterns of one or more genes in normal and abnormal cells. This provides a battery of genes (e.g., including beta-netrin) that could serve as a molecular target for diagnosis or therapeutic intervention.

In another aspect, the invention features an array having a plurality of addresses. Each address of the plurality includes a unique polypeptide. At least one address of the plurality has disposed thereon a beta-netrin polypeptide or fragment thereof. Methods of producing polypeptide arrays are described in the art, e.g., in De Wildt et al. (2000). *Nature Biotech.* 18, 989-994; Lueking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760-1763; and WO 99/51773A1. In a preferred embodiment, each addresses of the plurality has disposed thereon a polypeptide at least 60, 70, 80, 85, 90, 95, or 99% identical to a beta-netrin polypeptide or fragment thereof. For example, multiple variants of a beta-netrin polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a beta-netrin binding compound, e.g., an antibody in a sample from a subject with specificity for a beta-netrin polypeptide or the presence of a beta-netrin-binding protein or ligand.

The array is also useful for ascertaining the effect of the expression of a gene on the expression of other genes in the same cell or in different cells (e.g., ascertaining the effect of beta-netrin expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express beta-netrin or from a cell or subject in which a beta-netrin mediated response has been elicited, e.g., by contact of the cell with beta-netrin nucleic acid or protein, or administration to the cell or subject beta-netrin nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express beta-netrin (or does not express as highly as in the case of the beta-netrin positive plurality of capture probes) or from a cell or subject which in which a beta-netrin mediated response has not been elicited (or has been elicited to a lesser extent than in the first sample); contacting the array with one or more inquiry probes (which is preferably other than a beta-netrin nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express beta-netrin or from a cell or subject in which a beta-netrin-mediated response has been elicited, e.g., by contact of the cell with beta-netrin nucleic acid or protein, or administration to the cell or subject beta-netrin nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express beta-netrin (or does not express as highly as in the case of the beta-netrin positive plurality of capture probes) or from a cell or subject which in which a beta-netrin mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing beta-netrin, e.g., analyzing structure, function, or relatedness to other nucleic acid or amino acid sequences. The method includes: providing a beta-netrin nucleic acid or amino acid sequence; comparing the beta-netrin sequence with one or more preferably a plurality of sequences from a collection of sequences, e.g., a nucleic acid or protein sequence database; to thereby analyze beta-netrin.

Detection of Variations or Mutations

The methods of the invention can also be used to detect genetic alterations in a beta-netrin gene, thereby determining if a subject with the altered gene is at risk for a disorder characterized by mis-regulation in beta-netrin protein activity or nucleic acid expression, such as an immune disorder, a neurodegenerative disorder, or a cardiovascular disorder. In preferred embodiments, the methods include detecting, in a sample from the subject, the presence or absence of a genetic alteration characterized by at least one of an alteration affecting the integrity of a gene encoding a beta-netrin-protein, or the mis-expression of the beta-netrin gene. For example, such genetic alterations can be detected by ascertaining the existence of at least one of 1) a deletion of one or more nucleotides from a beta-netrin gene; 2) an addition of one or more nucleotides to a beta-netrin gene; 3) a substitution of one or more nucleotides of a beta-netrin gene, 4) a chromosomal rearrangement of a beta-netrin gene; 5) an alteration in the level of a messenger RNA transcript of a beta-netrin gene, 6) aberrant modification of a beta-netrin gene, such as of the methylation pattern of the genomic DNA, 7) the presence of a non-wild type splicing pattern of a messenger RNA transcript of a beta-netrin gene, 8) a non-wild type level of a beta-netrin-protein, 9) allelic loss of a beta-netrin gene, and 10) inappropriate post-translational modification of a beta-netrin-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the beta-netrin-gene. This method can include the steps of collecting a sample of cells from a subject, isolating nucleic acid (e.g., genomic, mRNA or both) from the sample, contacting the nucleic acid sample with one or more primers which specifically hybridize to a beta-netrin gene under conditions such that hybridization and amplification of the beta-netrin-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874-1878), transcriptional amplification system (Kwoh, D. Y. et al., (1989) *Proc. Natl. Acad. Sci. USA* 86:1173-1177), Q-Beta Replicase (Lizardi, P. M. et al. (1988) *Bio-Technology* 6:1197), or other nucleic acid amplification methods, followed by the detection of the amplified molecules using techniques known to those of skill in the art.

In another embodiment, mutations in a beta-netrin gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in beta-netrin can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin, M. T. et al. (1996) *Human Mutation* 7: 244-255; Kozal, M. J. et al. (1996) *Nature Medicine* 2: 753-759). For example, genetic mutations in beta-netrin can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the beta-netrin gene and detect mutations by comparing the sequence of the sample beta-netrin with the corresponding wild-type (control) sequence. Automated sequencing procedures can be utilized when performing the diagnostic assays ((1995) *Biotechniques* 19:448), including sequencing by mass spectrometry.

Other methods for detecting mutations in the beta-netrin gene include methods in which protection from cleavage agents is used to detect mismatched bases in RNA/RNA or RNA/DNA heteroduplexes (Myers et al. (1985) *Science* 230: 1242; Cotton et al. (1988) *Proc. Natl. Acad Sci USA* 85:4397; Saleeba et al. (1992) *Methods Enzymol.* 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in beta-netrin cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662; U.S. Pat. No. 5,459,039).

In other embodiments, alterations in electrophoretic mobility will be used to identify mutations in beta-netrin genes. For example, single strand conformation polymorphism (SSCP) may be used to detect differences in electrophoretic mobility between mutant and wild type nucleic acids (Orita et al. (1989) *Proc Natl. Acad. Sci. USA:* 86:2766, see also Cotton (1993) *Mutat. Res.* 285:125-144; and Hayashi (1992) *Genet. Anal. Tech. Appl.* 9:73-79). Single-stranded DNA fragments of sample and control beta-netrin nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl. Acad. Sci. USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell. Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a beta-netrin nucleic acid.

In a preferred embodiment the set includes a first and a second oligonucleotide. The first and second oligonucleotide can hybridize to the same or to different locations of SEQ ID NO:1, 3, or 4, or the complement of SEQ ID NO:1, 3, or 4. Different locations can be different but overlapping or or nonoverlapping on the same strand. The first and second oligonucleotide can hybridize to sites on the same or on different strands.

The set can be useful, e.g., for identifying SNP's, or identifying specific alleles of beta-netrin. In a preferred embodiment, each oligonucleotide of the set has a different nucleotide at an interrogation position. In one embodiment, the set includes two oligonucleotides, each complementary to a different allele at a locus, e.g., a biallelic or polymorphic, locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a beta-netrin nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a beta-netrin gene.

Use of Beta-Netrin Molecules as Surrogate Markers

The beta-netrin molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the beta-netrin molecules of the invention may be detected, and may be correlated with one or more biological states in vivo. For example, the beta-netrin molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The beta-netrin molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a beta-netrin marker) transcription or expression, the amplified marker may be in a quantity which is more readily detectable than the drug itself. Also, the marker may be more easily detected due to the nature of the marker itself; for example, using the methods described herein, anti-beta-netrin antibodies may be employed in an immune-based detection system for a beta-netrin protein marker, or beta-netrin-specific radiolabeled probes may be used to detect a beta-netrin mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S16-S20.

The beta-netrin molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., beta-netrin protein or RNA) for specific tumor markers in a subject, a drug or course of treatment may be selected that is optimized for the treatment of the specific tumor likely to be present in the subject. Similarly, the presence or absence of a specific sequence mutation in beta-netrin DNA may correlate beta-netrin drug response. The use of pharmacogenomic markers therefore permits the application of the most appropriate treatment for each subject without having to administer the therapy.

Pharmaceutical Compositions

The nucleic acid and polypeptides, fragments thereof, as well as anti-beta-netrin antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/

ED50. Compounds which exhibit high therapeutic indeces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted beta-netrin expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the beta-netrin molecules of the present invention or beta-netrin modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted beta-netrin expression or activity, by administering to the subject a beta-netrin or an agent which modulates beta-netrin expression or at least one beta-netrin activity. Subjects at risk for a disease which is caused or contributed to by aberrant or unwanted beta-netrin expression or activity can be identified by, for example, any or a combination of diagnostic or prognostic assays as described herein. Administration of a prophylactic agent can occur prior to the manifestation of symptoms characteristic of the beta-netrin aberrance, such that a disease or disorder is prevented or, alternatively, delayed in its progression. Depending on the type of beta-netrin aberrance, for example, a beta-netrin, beta-netrin agonist or beta-netrin antagonist agent can be used for treating the subject. The appropriate agent can be determined based on screening assays described herein.

It is possible that some beta-netrin disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed, successful treatment of beta-netrin disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of beta-netrin disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by beta-netrin expression is through the use of aptamer molecules specific for beta-netrin protein. Aptamers are nucleic acid molecules having a tertiary structure which permits them to specifically bind to protein ligands (see, e.g., Osborne, et al. *Curr. Opin. Chem. Biol.* 1997, 1(1): 5-9; and Patel, D. J. *Curr Opin Chem Biol* 1997 Jun. 1(1):32-46). Since nucleic acid molecules may in many cases be more conveniently introduced into target cells than therapeutic protein molecules may be, aptamers offer a method by which beta-netrin protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of beta-netrin disorders. For a description of antibodies, see the Antibody section above.

In circumstances wherein injection of an animal or a human subject with a beta-netrin protein or epitope for stimulating antibody production is harmful to the subject, it is possible to generate an immune response against beta-netrin through the use of anti-idiotypic antibodies (see, for example, Herlyn, D. *Ann Med* 1999; 31(1):66-78; and Bhattacharya-Chatterjee, M., and Foon, K. A. *Cancer Treat Res* 1998; 94:51-68). If an anti-idiotypic antibody is introduced into a mammal or human subject, it should stimulate the production of anti-anti-idiotypic antibodies, which should be specific to the beta-netrin protein. Vaccines directed to a disease characterized by beta-netrin expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993, *Proc. Natl. Acad. Sci*. USA 90:7889-7893).

The identified compounds that inhibit target gene expression, synthesis and/or activity can be administered to a patient at therapeutically effective doses to prevent, treat or ameliorate beta-netrin disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of “free” and “bound” compound in the serum of the test subject. Such assays may utilize antibody mimics and/or “biosensors” that have been created through molecular imprinting techniques. The compound which is able to modulate beta-netrin activity is used as a template, or “imprinting molecule”, to spatially organize polymerizable monomers prior to their polymerization with catalytic reagents. The subsequent removal of the imprinted molecule leaves a polymer matrix which contains a repeated “negative image” of the compound and is able to selectively rebind the molecule under biological assay conditions. A detailed review of this technique can be seen in Ansell, R. J. et al (1996) *Current Opinion in Biotechnology* 7:89-94 and in Shea, K. J. (1994) *Trends in Polymer Science* 2:166-173. Such “imprinted” affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645-647. Through the use of isotope-labeling, the “free” concentration of compound which modulates the expression or activity of beta-netrin can be readily monitored and used in calculations of $IC_{50}$.

Such “imprinted” affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a “biosensor” is discussed in Kriz, D. et al (1995) *Analytical Chemistry* 67:2142-2144.

Another aspect of the invention pertains to methods of modulating beta-netrin expression or activity for therapeutic purposes. Accordingly, in an exemplary embodiment, the modulatory method of the invention involves contacting a cell with a beta-netrin or agent that modulates one or more of the activities of beta-netrin protein activity associated with the cell. An agent that modulates beta-netrin protein activity can be an agent as described herein, such as a nucleic acid or a protein, a naturally-occurring target molecule of a beta-netrin protein (e.g., a beta-netrin substrate or receptor), a beta-netrin antibody, a beta-netrin agonist or antagonist, a peptidomimetic of a beta-netrin agonist or antagonist, or other small molecule.

In one embodiment, the agent stimulates one or beta-netrin activities. Examples of such stimulatory agents include active beta-netrin protein and a nucleic acid molecule encoding beta-netrin. In another embodiment, the agent inhibits one or more beta-netrin activities. Examples of such inhibitory agents include antisense beta-netrin nucleic acid molecules, antibeta-netrin antibodies, and beta-netrin inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a beta-netrin protein or nucleic acid molecule. In one embodiment, the method involves administering an agent (e.g., an agent identified by a screening assay described herein), or combination of agents that modulates (e.g., upregulates or downregulates) beta-netrin expression or activity. In another embodiment, the method involves administering a beta-netrin protein or nucleic acid molecule as therapy to compensate for reduced, aberrant, or unwanted beta-netrin expression or activity.

Stimulation of beta-netrin activity is desirable in situations in which beta-netrin is abnormally downregulated and/or in which increased beta-netrin activity is likely to have a beneficial effect. For example, stimulation of beta-netrin activity is desirable in situations in which a beta-netrin is downregulated and/or in which increased beta-netrin activity is likely to have a beneficial effect. Likewise, inhibition of beta-netrin activity is desirable in situations in which beta-netrin is abnormally upregulated and/or in which decreased beta-netrin activity is likely to have a beneficial effect.

Pharmacogenomics

The beta-netrin molecules of the present invention, as well as agents, or modulators which have a stimulatory or inhibitory effect on beta-netrin activity (e.g., beta-netrin gene expression) as identified by a screening assay described herein can be administered to individuals to treat (prophylactically or therapeutically) beta-netrin associated disorders (e.g., cellular growth related disorders) associated with aberrant or unwanted beta-netrin activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a beta-netrin molecule or beta-netrin modulator as well as tailoring the dosage and/or therapeutic regimen of treatment with a beta-netrin molecule or beta-netrin modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10-11): 983-985 and Linder, M. W. et al. (1997) Clin. Chem. 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a beta-netrin protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a beta-netrin molecule or beta-netrin modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a beta-netrin molecule or beta-netrin modulator, such as a modulator identified by one of the exemplary screening assays described herein.

The present invention further provides methods for identifying new agents, or combinations, that are based on identifying agents that modulate the activity of one or more of the gene products encoded by one or more of the beta-netrin genes of the present invention, wherein these products may be associated with resistance of the cells to a therapeutic agent. Specifically, the activity of the proteins encoded by the beta-netrin genes of the present invention can be used as a basis for identifying agents for overcoming agent resistance. By blocking the activity of one or more of the resistance proteins, target cells, e.g., cancer cells, will become sensitive to treatment with an agent that the unmodified target cells were resistant to.

Monitoring the influence of agents (e.g., drugs) on the expression or activity of a beta-netrin protein can be applied in clinical trials. For example, the effectiveness of an agent determined by a screening assay as described herein to increase beta-netrin gene expression, protein levels, or upregulate beta-netrin activity, can be monitored in clinical trials of subjects exhibiting decreased beta-netrin gene expression, protein levels, or downregulated beta-netrin activity. Alternatively, the effectiveness of an agent determined by a screening assay to decrease beta-netrin gene expression, protein levels, or downregulate beta-netrin activity, can be monitored in clinical trials of subjects exhibiting increased beta-netrin gene expression, protein levels, or upregulated beta-netrin activity. In such clinical trials, the expression or activity of a beta-netrin gene, and preferably, other genes that have been implicated in, for example, a beta-netrin-associated disorder can be used as a "read out" or markers of the phenotype of a particular cell.

OTHER EMBODIMENTS

Included in the invention are: allelic variations; natural mutants; induced mutants; proteins encoded by DNA that hybridizes under high or low stringency conditions to a nucleic acid which encodes a polypeptide of SEQ ID NO:2 or SEQ ID NO:5 (for definitions of high and low stringency see Current Protocols in Molecular Biology, John Wiley & Sons, New York, 1989, 6.3.1-6.3.6, hereby incorporated by reference); and, polypeptides specifically bound by antisera to β-netrin.

Nucleic acids and polypeptides of the invention include those that differ from the sequences disclosed herein by virtue of sequencing errors in the disclosed sequences.

The invention also includes fragments, preferably biologically active fragments, or analogs of β-netrin. A biologically active fragment or analog is one having any in vivo or in vitro activity which is characteristic of β-netrin shown in SEQ ID NO:2 or SEQ ID NO:5, or of other naturally occurring β-netrin, e.g., one or more of the biological activities described above. Especially preferred are fragments which exist in vivo, e.g., fragments which arise from post transcriptional processing or which arise from translation of alternatively spliced RNA's. Fragments include those expressed in native or endogenous cells, e.g., as a result of post-translational processing, e.g., as the result of the removal of an amino-terminal signal sequence, as well as those made in expression systems, e.g., in CHO cells. Particularly preferred fragments are fragments, e.g., active fragments, which are generated by proteolytic cleavage or alternative splicing events.

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a 1983, 52881, 2398, 45449, 50289, or 52872, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the β-netrin nucleic acid, polypeptide, or antibody.

The capture probes can be a set of nucleic acids from a selected sample, e.g., a sample of nucleic acids derived from a control or non-stimulated tissue or cell.

The method can include contacting the β-netrin nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of β-netrin. Such methods can be used to diagnose a subject, e.g., to evaluate risk for a disease or disorder, to evaluate suitability of a selected treatment for a subject, to evaluate whether a subject has a disease or disorder. β-netrin is associated with ovarian cancer, tumorigenesis, and renal, cardiovascular, ovarian, and neurological disorders.

The method can be used to detect SNPs, as described herein.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express β-netrin or from a cell or subject in which a β-netrin mediated response has been elicited, e.g., by contact of the cell with β-netri nucleic acid or protein, or administration to the cell or subject β-netrin nucleic acid or protein; contacting the array with one or more inquiry probe, wherein an inquiry probe can be a nucleic acid, polypeptide, or antibody (which is preferably other than β-netrin nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express β-netrin (or does not express as highly as in the case of the β-netrin positive plurality of capture probes) or from a cell or subject which in which a β-netrin mediated response has not been elicited (or has been elicited to a lesser extent than in the first sample); contacting the array with one or more inquiry probes (which is preferably other than a β-netrin nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing β-netrin, e.g., analyzing structure, function, or relatedness to other nucleic acid or amino acid sequences. The method includes: providing a β-netrin nucleic acid or amino acid sequence, e.g., a nucleotide sequence from 300-1916 or a portion thereof; comparing the β-netrin sequence with one or more preferably a plurality of sequences from a collection of sequences, e.g., a nucleic acid or protein sequence database; to thereby analyze β-netrin.

The method can include evaluating the sequence identity between a β-netrin sequence and a database sequence. The method can be performed by accessing the database at a second site, e.g., over the internet.

In another aspect, the invention features, a set of oligonucleotides, useful, e.g., for identifying SNP's, or identifying specific alleles of β-netrin. The set includes a plurality of oligonucleotides, each of which has a different nucleotide at an interrogation position, e.g., an SNP or the site of a mutation. In a preferred embodiment, the oligonucleotides of the plurality are identical in sequence with one another (except for differences in length). The oligonucleotides can be provided with diferential labels, such that an oligonucleotide which hybridizes to one allele provides a signal that is distinguishable from an oligonucleotide which hybridizes to a second allele.

Other embodiments are within the following claims.

What is claimed is:

1. A substantially pure polypeptide which comprises at least 90% sequence identity to the amino acid sequence of SEQ ID NO:2, wherein the polypeptide has an activity of promoting neurite outgrowth in vitro or of reducing tumor growth in vitro.

2. The beta-netrin polypeptide of claim 1 comprising the amino acid sequence of SEQ ID NO:2.

3. A substantially pure beta-netrin polypeptide which is encoded by a nucleic acid having at least 90% sequence identity with the nucleic acid of SEQ ID NO:1, SEQ ID NO:3, or SEQ ID NO:5.

4. The polypeptide of claim 1, wherein the polypeptide has any one or more of the following properties:
   (i) it includes a laminin N-terminal VI Domain;
   (ii) it includes an EGF-like Domain V;
   (iii) it includes a C-terminal frz domain;
   (iv) it has the ability to modulate neurite guidance, or stability;
   (v) it has the ability to modulate development of the vascular system;
   (vi) it has the ability to modulate angiogenesis;
   (vii) it has the ability to modulate muscular development or innervation; and
   (viii) it has a molecular weight characteristic of beta-netrin of SEQ ID NO:2.

5. An immunogen comprising the polypeptide of claim 1 in an immunogenic preparation, the immunogen being capable of eliciting an immune response specific for the polypeptide.

6. A substantially pure polypeptide encoded by a nucleic acid that hybridizes under high stringency conditions to a nucleic acid consisting of nucleotides 452-2333 of SEQ ID NO:1 or its full complement, wherein the polypeptide has a β-netrin activity of promoting neurite outgrowth in vitro or of reducing tumor growth in vitro.

7. A substantially pure polypeptide comprising an amino acid sequence at least 90% identical to the amino acid sequence of a domain of SEQ ID NO:2, wherein the domain is selected from the group consisting of:

(i) a laminin N-terminal VI Domain;
(ii) an EGF-like Domain V; and
(iii) a C-terminal frz domain.

8. The polypeptide of claim 1 which has at least 95% sequence identity to the amino acid sequence of SEQ ID NO:2.

9. The polypeptide of claim 1 which has at least 98% sequence identity to the amino acid sequence of SEQ ID NO:2.

* * * * *

UNITED STATES PATENT AND TRADEMARK OFFICE
CERTIFICATE OF CORRECTION

PATENT NO. : 7,531,625 B2  Page 1 of 1
APPLICATION NO. : 10/831979
DATED : May 12, 2009
INVENTOR(S) : Pamela Olson et al.

It is certified that error appears in the above-identified patent and that said Letters Patent is hereby corrected as shown below:

On Title page, column 1, item (73), "The General Hospital Corporation, Boston, MA (US)" should read --The General Hospital Corporation, Boston, MA (US); Tufts University, Medford, MA (US)--

Signed and Sealed this

Ninth Day of March, 2010

David J. Kappos
*Director of the United States Patent and Trademark Office*

SEQUENCE LISTING

<160> NUMBER OF SEQ ID NOS: 15

<210> SEQ ID NO 1
<211> LENGTH: 3626

```
<212> TYPE: DNA
<213> ORGANISM: Homo sapiens
<220> FEATURE:
<221> NAME/KEY: CDS
<222> LOCATION: (452)...(2335)
<220> FEATURE:
<221> NAME/KEY: misc_feature
<222> LOCATION: 1-18, 101-117, 201-217, 3171
<223> OTHER INFORMATION: n = a, t, c, or g

<400> SEQUENCE: 1
```

| | | |
|---|---|---|
| nnnnnnnnnn nnnnnnnngc agccagaaga ggtgggaaaa gcggaggagg acgcccagga | 60 | |
| ggaggcggcg gcggcggccg ggaagtgaaa ggtctcgcaa nnnnnnnnnn nnnnnnncgg | 120 | |
| gcgccgagcc ccgggatagc ggcagacgag cccgcagggc cgctccgcgg ggcagcgcag | 180 | |
| ccaggccggc tatggtcccg nnnnnnnnnn nnnnnnncag gtgcccggga cccgccaggc | 240 | |
| cggtgcgcga gggtcacccc acctccccgc gcggtcccgg ccctggctc ccagctgccg | 300 | |
| gcgaccgctg accgagcccg cgccccagg aggaggaaga aaccagggcc ccgttccctc | 360 | |
| ccgaggacgg cggcgcttca tcccgcagcc cagaggtctc ggctccctcc ggcacccgcc | 420 | |
| cggcccggct gctccctggc tcctcccggc c atg ggg agc tgc gcg cgg ctg | 472 |
| | Met Gly Ser Cys Ala Arg Leu | |
| | 1   5 | |

```
ctg ctg ctc tgg ggc tgc acg gtg gtg gcc gca gga ctg agt gga gta      520
Leu Leu Leu Trp Gly Cys Thr Val Val Ala Ala Gly Leu Ser Gly Val
        10                  15                  20 gct gga gtg agt tcc cgc tgt gaa aaa gcc tgc aac cct cgg atg gga      568
Ala Gly Val Ser Ser Arg Cys Glu Lys Ala Cys Asn Pro Arg Met Gly
 25                  30                  35 aat ttg gct ttg ggg cga aaa ctc tgg gca gac acc acc tgc ggt cag      616
Asn Leu Ala Leu Gly Arg Lys Leu Trp Ala Asp Thr Thr Cys Gly Gln
 40                  45                  50                  55 aat gct acc gaa ctg tac tgc ttc tac agt gag aac aag gat ctg act      664
Asn Ala Thr Glu Leu Tyr Cys Phe Tyr Ser Glu Asn Lys Asp Leu Thr
                 60                  65                  70 tgt cgg cag ccc aaa tgt gac aag tgc aat gct gcc tat cct cac ctg      712
Cys Arg Gln Pro Lys Cys Asp Lys Cys Asn Ala Ala Tyr Pro His Leu
             75                  80                  85 gct cac ctg cca tct gcc atg gca gac tca tcc ttc cgg ttt cct cgc      760
Ala His Leu Pro Ser Ala Met Ala Asp Ser Ser Phe Arg Phe Pro Arg
         90                  95                 100 aca tgg tgg cag tct gcg gag gat gtg cac aga gaa aag atc cag tta      808
Thr Trp Trp Gln Ser Ala Glu Asp Val His Arg Glu Lys Ile Gln Leu
    105                 110                 115 gac ctg gaa gct gaa ttc tac ttc act cac cta att gtg atg ttc aag      856
Asp Leu Glu Ala Glu Phe Tyr Phe Thr His Leu Ile Val Met Phe Lys
120                 125                 130                 135 tcc ccc agg ccg gct gcc atg gtg ctg gac cgc tcc cag gac ttt ggg      904
Ser Pro Arg Pro Ala Ala Met Val Leu Asp Arg Ser Gln Asp Phe Gly
                140                 145                 150 aaa aca tgg aag cct tat aag tac ttt gcg act aac tgc tcc gct aca      952
Lys Thr Trp Lys Pro Tyr Lys Tyr Phe Ala Thr Asn Cys Ser Ala Thr
            155                 160                 165 ttt ggc ctg gaa gat gat gtt gtc aag aag ggc gct att tgt act tct     1000
Phe Gly Leu Glu Asp Asp Val Val Lys Lys Gly Ala Ile Cys Thr Ser
        170                 175                 180 aaa tac tcc agt cct ttt cca tgc act gga gga gag gtt att ttc aaa     1048
Lys Tyr Ser Ser Pro Phe Pro Cys Thr Gly Gly Glu Val Ile Phe Lys
    185                 190                 195 gct ttg tca cca cca cac gat aca gag aac cct tac agt gcc aaa gtt     1096
```

```
                     Ala Leu Ser Pro Pro His Asp Thr Glu Asn Pro Tyr Ser Ala Lys Val
                     200                 205                 210                 215 cag gag cag ctg aag atc acc aac ctt cgc gtg cag ctg ctg aaa cga         1144
Gln Glu Gln Leu Lys Ile Thr Asn Leu Arg Val Gln Leu Leu Lys Arg
                    220                 225                 230 cag tct tgt ccc tgt cag aga aat gac ctg aac gaa gag cct caa cat         1192
Gln Ser Cys Pro Cys Gln Arg Asn Asp Leu Asn Glu Glu Pro Gln His
                235                 240                 245 ttt aca cac tat gcg atc tat gat ttc att gtc aag ggc agc tgc ttc         1240
Phe Thr His Tyr Ala Ile Tyr Asp Phe Ile Val Lys Gly Ser Cys Phe
            250                 255                 260 tgc aat ggc cac gcc gat caa tgc ata cct gtt cat ggc ttc aga cct         1288
Cys Asn Gly His Ala Asp Gln Cys Ile Pro Val His Gly Phe Arg Pro
265                 270                 275 gtc aag gcc cca gga aca ttc cac atg gtc cat ggg aag tgt atg tgt         1336
Val Lys Ala Pro Gly Thr Phe His Met Val His Gly Lys Cys Met Cys
280                 285                 290                 295 aag cac aac aca gca ggc agc cac tgc cag cac tgt gcc ccg tta tac         1384
Lys His Asn Thr Ala Gly Ser His Cys Gln His Cys Ala Pro Leu Tyr
                300                 305                 310 aat gac cgg cca tgg gag gca gct gat ggc aaa acg ggg gct ccc aac         1432
Asn Asp Arg Pro Trp Glu Ala Ala Asp Gly Lys Thr Gly Ala Pro Asn
                315                 320                 325 gag tgc aga gcc tgc aag tgt aat ggg cat gct gat acc tgt cac ttc         1480
Glu Cys Arg Ala Cys Lys Cys Asn Gly His Ala Asp Thr Cys His Phe
                330                 335                 340 gac gtt aat gtg tgg gag gca tca ggg aat cgt agt ggt ggt gtc tgt         1528
Asp Val Asn Val Trp Glu Ala Ser Gly Asn Arg Ser Gly Gly Val Cys
345                 350                 355 gat gac tgt cag cac aac aca gaa gga cag tat tgc cag agg tgc aag         1576
Asp Asp Cys Gln His Asn Thr Glu Gly Gln Tyr Cys Gln Arg Cys Lys
360                 365                 370                 375 cca ggc ttc tat cgt gac ctg cgg aga ccc ttc tca gct cca gat gct         1624
Pro Gly Phe Tyr Arg Asp Leu Arg Arg Pro Phe Ser Ala Pro Asp Ala
                380                 385                 390 tgc aaa ccg tgt tcc tgc cat cca gta gga tca gct gtc ctt cct gcc         1672
Cys Lys Pro Cys Ser Cys His Pro Val Gly Ser Ala Val Leu Pro Ala
                395                 400                 405 aac tca gtg acc ttc tgc gac ccc agc aat ggt gac tgc cct tgc aag         1720
Asn Ser Val Thr Phe Cys Asp Pro Ser Asn Gly Asp Cys Pro Cys Lys
            410                 415                 420 cct ggg gtg gca ggg cga cgt tgt gac agg tgc atg gtg gga tac tgg         1768
Pro Gly Val Ala Gly Arg Arg Cys Asp Arg Cys Met Val Gly Tyr Trp
425                 430                 435 ggc ttc gga gac tat ggc tgt cga cca tgt gac tgt gcg ggg agc tgt         1816
Gly Phe Gly Asp Tyr Gly Cys Arg Pro Cys Asp Cys Ala Gly Ser Cys
440                 445                 450                 455 gac cct atc acc gga gac tgc atc agc agc cac aca gac ata gac tgg         1864
Asp Pro Ile Thr Gly Asp Cys Ile Ser Ser His Thr Asp Ile Asp Trp
                460                 465                 470 tgt cat gaa gtt cct gac ttc cgt ccc gtg cac aat aag agc gaa cca         1912
Cys His Glu Val Pro Asp Phe Arg Pro Val His Asn Lys Ser Glu Pro
                475                 480                 485 gcc tgg gag tgg gag gat gcg cag ggg ttt tct gca ctt cta cac tca         1960
Ala Trp Glu Trp Glu Asp Ala Gln Gly Phe Ser Ala Leu Leu His Ser
                490                 495                 500 ggt aaa tgc gaa tgt aag gaa cag aca tta gga aat gcc aag gca ttc         2008
Gly Lys Cys Glu Cys Lys Glu Gln Thr Leu Gly Asn Ala Lys Ala Phe
505                 510                 515
```

```
tgt gga atg aaa tat tca tat gtg cta aaa ata aag att tta tca gct      2056
Cys Gly Met Lys Tyr Ser Tyr Val Leu Lys Ile Lys Ile Leu Ser Ala
520                 525                 530                 535 cat gat aaa ggt act cat gtt gag gtc aat gtg aag att aaa aag gtc      2104
His Asp Lys Gly Thr His Val Glu Val Asn Val Lys Ile Lys Lys Val
                540                 545                 550 tta aaa tct acc aaa ctg aag att ttc cga gga aag cga aca tta tat      2152
Leu Lys Ser Thr Lys Leu Lys Ile Phe Arg Gly Lys Arg Thr Leu Tyr
            555                 560                 565 cca gaa tca tgg acg gac aga gga tgc act tgt cca atc ctc aat cct      2200
Pro Glu Ser Trp Thr Asp Arg Gly Cys Thr Cys Pro Ile Leu Asn Pro
        570                 575                 580 ggt ttg gaa tac ctt gta gca gga cat gag gat ata aga aca ggc aaa      2248
Gly Leu Glu Tyr Leu Val Ala Gly His Glu Asp Ile Arg Thr Gly Lys
    585                 590                 595 cta att gtg aat atg aaa agc ttt gtc cag cac tgg aaa cct tct ctt      2296
Leu Ile Val Asn Met Lys Ser Phe Val Gln His Trp Lys Pro Ser Leu
600                 605                 610                 615 gga aga aaa gtc atg gat att tta aaa aga gag tgc aag tagcattaag      2345
Gly Arg Lys Val Met Asp Ile Leu Lys Arg Glu Cys Lys
                620                 625 atggatagca cataatggca cttgtctatg tacaaaacac aaactttaga gcaagaagac    2405
ctcagacagg aaactggaat tttttaaagt gccaaaacat atagaaatgt ttgaatgcat    2465
gggtcttatc taatttatct cttctggacc catgtttaaa tacagttta tttcatgaag     2525 agaaatgaaa acccctacac tgatatctgt tttctatggg actgattctg aaattcttaa    2585
ctattaagaa tattttaata gcagcatgac atttagcagt aatccattaa gggcagtacc    2645
tctaacaagg acgccttcca gcttcagcta tgttacttac gtttgatgct acttaaagta    2705
atgaatgacg ttttaaggaa tccctaaccc tactatcaga aaaggtgttt gttaaagagc    2765
cttctcttgt gtgttacgca tgaactttgg tctgtaggtg ttaaatggaa cctctccatg    2825
tgtatatagt atttccttgt ataaagcact ttactaccta ccacttgtgt tgtgaacgtt    2885
tggtgactgc tgttgaaaga aggaaaaggg tgtgtgagaa agcctactga agcagctgca    2945
cggccactac atgtggacaa aagtgaacat ataaaagaag ttgtgctatt taactctgaa    3005
tacttggaga aactaggtga agatgcaacc agaaaggaga atatgtatgc gtgaagtctc    3065
agctttgagc kggaggctag ayyccaagak gmcagccakg akgaamctttt ttaaaaamct    3125 aamccagaag agmctttaaa ataagagaaa gaaatcataa atgtangaca tatgcttggc    3185 taaagggggaa atggacttta aattttaaag agctcatttg caatgcactt gtatacactt    3245
caaaaattat tgtagacaca gaatttgtta tattttgtg cttagtattt aaacctgaac     3305
attgaaacag ttttcctcct tgtctttctt aacagtaata gtcattatat ttacctgttt    3365
tttaacacaa tgtatgtgat agtcaaaaaa tcacagtttt tcattattat tcatcttctg    3425
tacccacgca taaccactat acatagtttc ttttctactt gaatatacaa aacatgaaca    3485
cagtgccata tgaataattt cacatacaga accttttttt ctctgaagtc ctgtggactt    3545
gcaaatatat atatatattg ctttgttaat ttgttttttat atttcatata tgtaataaag   3605
gaatatgatc tgaaaaaaaa a                                              3626

<210> SEQ ID NO 2
<211> LENGTH: 628
<212> TYPE: PRT
<213> ORGANISM: Homo sapiens

<400> SEQUENCE: 2
```

-continued

```
Met Gly Ser Cys Ala Arg Leu Leu Leu Leu Trp Gly Cys Thr Val Val
 1               5                  10                  15

Ala Ala Gly Leu Ser Gly Val Ala Gly Val Ser Ser Arg Cys Glu Lys
            20                  25                  30

Ala Cys Asn Pro Arg Met Gly Asn Leu Ala Leu Gly Arg Lys Leu Trp
        35                  40                  45

Ala Asp Thr Thr Cys Gly Gln Asn Ala Thr Glu Leu Tyr Cys Phe Tyr
    50                  55                  60

Ser Glu Asn Lys Asp Leu Thr Cys Arg Gln Pro Lys Cys Asp Lys Cys
65                  70                  75                  80

Asn Ala Ala Tyr Pro His Leu Ala His Leu Pro Ser Ala Met Ala Asp
                85                  90                  95

Ser Ser Phe Arg Phe Pro Arg Thr Trp Trp Gln Ser Ala Glu Asp Val
            100                 105                 110

His Arg Glu Lys Ile Gln Leu Asp Leu Glu Ala Glu Phe Tyr Phe Thr
        115                 120                 125

His Leu Ile Val Met Phe Lys Ser Pro Arg Pro Ala Ala Met Val Leu
    130                 135                 140

Asp Arg Ser Gln Asp Phe Gly Lys Thr Trp Lys Pro Tyr Lys Tyr Phe
145                 150                 155                 160

Ala Thr Asn Cys Ser Ala Thr Phe Gly Leu Glu Asp Asp Val Val Lys
                165                 170                 175

Lys Gly Ala Ile Cys Thr Ser Lys Tyr Ser Ser Pro Phe Pro Cys Thr
            180                 185                 190

Gly Gly Glu Val Ile Phe Lys Ala Leu Ser Pro Pro His Asp Thr Glu
        195                 200                 205

Asn Pro Tyr Ser Ala Lys Val Gln Glu Gln Leu Lys Ile Thr Asn Leu
    210                 215                 220

Arg Val Gln Leu Leu Lys Arg Gln Ser Cys Pro Cys Gln Arg Asn Asp
225                 230                 235                 240

Leu Asn Glu Glu Pro Gln His Phe Thr His Tyr Ala Ile Tyr Asp Phe
                245                 250                 255

Ile Val Lys Gly Ser Cys Phe Cys Asn Gly His Ala Asp Gln Cys Ile
            260                 265                 270

Pro Val His Gly Phe Arg Pro Val Lys Ala Pro Gly Thr Phe His Met
        275                 280                 285

Val His Gly Lys Cys Met Cys Lys His Asn Thr Ala Gly Ser His Cys
    290                 295                 300

Gln His Cys Ala Pro Leu Tyr Asn Asp Arg Pro Trp Glu Ala Ala Asp
305                 310                 315                 320

Gly Lys Thr Gly Ala Pro Asn Glu Cys Arg Ala Cys Lys Cys Asn Gly
                325                 330                 335

His Ala Asp Thr Cys His Phe Asp Val Asn Val Trp Glu Ala Ser Gly
            340                 345                 350

Asn Arg Ser Gly Gly Val Cys Asp Asp Cys Gln His Asn Thr Glu Gly
        355                 360                 365

Gln Tyr Cys Gln Arg Cys Lys Pro Gly Phe Tyr Arg Asp Leu Arg Arg
    370                 375                 380

Pro Phe Ser Ala Pro Asp Ala Cys Lys Pro Cys Ser Cys His Pro Val
385                 390                 395                 400

Gly Ser Ala Val Leu Pro Ala Asn Ser Val Thr Phe Cys Asp Pro Ser
                405                 410                 415
```

```
Asn Gly Asp Cys Pro Cys Lys Pro Gly Val Ala Gly Arg Arg Cys Asp
            420                 425                 430
Arg Cys Met Val Gly Tyr Trp Gly Phe Gly Asp Tyr Gly Cys Arg Pro
        435                 440                 445
Cys Asp Cys Ala Gly Ser Cys Asp Pro Ile Thr Gly Asp Cys Ile Ser
    450                 455                 460
Ser His Thr Asp Ile Asp Trp Cys His Glu Val Pro Asp Phe Arg Pro
465                 470                 475                 480
Val His Asn Lys Ser Glu Pro Ala Trp Glu Trp Asp Ala Gln Gly
            485                 490                 495
Phe Ser Ala Leu Leu His Ser Gly Lys Cys Glu Cys Lys Glu Gln Thr
        500                 505                 510
Leu Gly Asn Ala Lys Ala Phe Cys Gly Met Lys Tyr Ser Tyr Val Leu
    515                 520                 525
Lys Ile Lys Ile Leu Ser Ala His Asp Lys Gly Thr His Val Glu Val
    530                 535                 540
Asn Val Lys Ile Lys Lys Val Leu Lys Ser Thr Lys Leu Lys Ile Phe
545                 550                 555                 560
Arg Gly Lys Arg Thr Leu Tyr Pro Glu Ser Trp Thr Arg Gly Cys
            565                 570                 575
Thr Cys Pro Ile Leu Asn Pro Gly Leu Glu Tyr Leu Val Ala Gly His
        580                 585                 590
Glu Asp Ile Arg Thr Gly Lys Leu Ile Val Asn Met Lys Ser Phe Val
        595                 600                 605
Gln His Trp Lys Pro Ser Leu Gly Arg Lys Val Met Asp Ile Leu Lys
    610                 615                 620
Arg Glu Cys Lys
625

<210> SEQ ID NO 3
<211> LENGTH: 1887
<212> TYPE: DNA
<213> ORGANISM: Homo sapiens

<400> SEQUENCE: 3
atggggagct gcgcgcggct gctgctgctc tggggctgca cggtggtggc cgcaggactg      60
agtggagtag ctggagtgag ttcccgctgt gaaaaagcct gcaaccctcg gatgggaaat     120
ttggctttgg ggcgaaaact ctgggcagac accacctgcg gtcagaatgc taccgaactg     180
tactgcttct acagtgagaa caaggatctg acttgtcggc agcccaaatg tgacaagtgc     240
aatgctgcct atcctcacct ggctcacctg ccatctgcca tggcagactc atccttccgg     300
tttcctcgca catggtggca gtctgcggag gatgtgcaca gagaaaagat ccagttagac     360
ctggaagctg aattctactt cactcaccta attgtgatgt tcaagtcccc caggccggct     420
gccatggtgc tggaccgctc ccaggacttt gggaaaacat ggaagcctta aagtactttt     480
gcgactaact gctccgctac atttggcctg aagatgatgt tgtcaagaa gggcgctatt     540
tgtacttcta atactccag tcctttccca tgcactggag agaggttat tttcaaagct     600
ttgtcaccac cacacgatac agagaaccct tacagtgcca agttcagga gcagctgaag     660
atcaccaacc ttcgcgtgca gctgctgaaa cgacagtctt gtccctgtca gagaaatgac     720
ctgaacgaag agcctcaaca ttttacacac tatgcgatct atgatttcat tgtcaagggc     780
agctgcttct gcaatggcca cgccgatcaa tgcataccctg ttcatggctt cagacctgtc     840
aaggccccag gaacattcca catggtccat gggaagtgta tgtgtaagca caacacagca     900
```

```
ggcagccact gccagcactg tgccccgtta tacaatgacc ggccatggga ggcagctgat      960
ggcaaaacgg gggctcccaa cgagtgcaga gcctgcaagt gtaatgggca tgctgatacc     1020
tgtcacttcg acgttaatgt gtgggaggca tcagggaatc gtagtggtgg tgtctgtgat     1080
gactgtcagc acaacacaga aggacagtat tgccagaggt gcaagccagg cttctatcgt     1140
gacctgcgga gacccttctc agctccagat gcttgcaaac cgtgttcctg ccatccagta     1200
ggatcagctg tccttcctgc caactcagtg accttctgcg accccagcaa tggtgactgc     1260
ccttgcaagc ctggggtggc agggcgacgt tgtgacaggt gcatggtggg atactggggc     1320
ttcggagact atggctgtcg accatgtgac tgtgcgggga gctgtgaccc tatcaccgga     1380
gactgcatca gcagccacac agacatagac tggtgtcatg aagttcctga cttccgtccc     1440
gtgcacaata agagcgaacc agcctgggag tgggaggatg cgcaggggtt ttctgcactt     1500
ctacactcag gtaaatgcga atgtaaggaa cagacattag gaaatgccaa ggcattctgt     1560
ggaatgaaat attcatatgt gctaaaaata aagattttat cagctcatga taaaggtact     1620
catgttgagg tcaatgtgaa gattaaaaag gtcttaaaat ctaccaaact gaagattttc     1680
cgaggaaagc gaacattata tccagaatca tggacggaca gaggatgcac ttgtccaatc     1740
ctcaatcctg gtttggaata ccttgtagca ggacatgagg atataagaac aggcaaacta     1800
attgtgaata tgaaaagctt tgtccagcac tggaaacctt ctcttggaag aaaagtcatg     1860
gatattttaa aaagagagtg caagtag                                         1887

<210> SEQ ID NO 4
<211> LENGTH: 2048
<212> TYPE: DNA
<213> ORGANISM: Mus musculus
<220> FEATURE:
<221> NAME/KEY: CDS
<222> LOCATION: (127)...(2010)

<400> SEQUENCE: 4
gcggctctgt gcccacggtg cccactgagc gagcctggcg ctccgggagg aggaagaaca     60
cagagccccc ggtgctcccg aggaccactg ccgcttcatc ccacccgctc ccgcagctgc    120 ccggcc atg ggg agc tgc gca cgg ctg ctg ctg ctc tgg ggc tgc tcc        168
       Met Gly Ser Cys Ala Arg Leu Leu Leu Leu Trp Gly Cys Ser
        1               5                   10 gcg gtg gcc gca ggc ttg aat gga gta gcc gga gcg aac tcc cgc tgt       216
Ala Val Ala Ala Gly Leu Asn Gly Val Ala Gly Ala Asn Ser Arg Cys
 15                  20                  25                  30 gag aag gca tgc aac cct cgc atg gga aac ttg gct ttg gga aga aag       264
Glu Lys Ala Cys Asn Pro Arg Met Gly Asn Leu Ala Leu Gly Arg Lys
                 35                  40                  45 ctc cgg gca gac act atg tgt ggc cag aac gcc acc gaa ctc ttc tgc       312
Leu Arg Ala Asp Thr Met Cys Gly Gln Asn Ala Thr Glu Leu Phe Cys
             50                  55                  60 ttc tac agt gag aat gct gac ctc act tgc cgg cag ccc aag tgt gat       360
Phe Tyr Ser Glu Asn Ala Asp Leu Thr Cys Arg Gln Pro Lys Cys Asp
 65                  70                  75 aaa tgc aac gct gcc cat tct cac cta gct cac cca ccc tct gcc atg       408
Lys Cys Asn Ala Ala His Ser His Leu Ala His Pro Pro Ser Ala Met
             80                  85                  90 gca gac tca tcc ttc agg ttt ccc cgg aca tgg tgg cag tct gca gag       456
Ala Asp Ser Ser Phe Arg Phe Pro Arg Thr Trp Trp Gln Ser Ala Glu
 95                 100                 105                 110 gat gtg cac agg gaa aag att cag cta gac ctg gaa gca gaa ttc tac       504
```

```
                Asp Val His Arg Glu Lys Ile Gln Leu Asp Leu Glu Ala Glu Phe Tyr
                                115                 120                 125 ttc act cac cta att atg gtg ttc aag tct ccc agg cct gca gcc atg          552
Phe Thr His Leu Ile Met Val Phe Lys Ser Pro Arg Pro Ala Ala Met
            130                 135                 140 gtg ctg gac cgg tcc cag gac ttt ggg aag acc tgg aag cct tac aag          600
Val Leu Asp Arg Ser Gln Asp Phe Gly Lys Thr Trp Lys Pro Tyr Lys
            145                 150                 155 tac ttt gca aca aac tgc tcg gct act ttt ggc ctg gaa gat gat gtt          648
Tyr Phe Ala Thr Asn Cys Ser Ala Thr Phe Gly Leu Glu Asp Asp Val
160                 165                 170 gtc aag aag gga gct att tgc acg tct aga tac tca aat cct ttc ccg          696
Val Lys Lys Gly Ala Ile Cys Thr Ser Arg Tyr Ser Asn Pro Phe Pro
175                 180                 185                 190 tgc acc gga gga gag gtt att ttc aga gcc ctg tca cca cca tac gac          744
Cys Thr Gly Gly Glu Val Ile Phe Arg Ala Leu Ser Pro Pro Tyr Asp
                    195                 200                 205 ata gaa aac cct tac agt gcc aaa gtg cag gag cag ctg aag atc acc          792
Ile Glu Asn Pro Tyr Ser Ala Lys Val Gln Glu Gln Leu Lys Ile Thr
                210                 215                 220 aac ctc cga gtg cgg ctc ctc aag cga cag tcc tgc cct tgt cag ata          840
Asn Leu Arg Val Arg Leu Leu Lys Arg Gln Ser Cys Pro Cys Gln Ile
            225                 230                 235 aac gac ctg aac gca aaa cct cac cat ttt atg cac tac gca gtc tat          888
Asn Asp Leu Asn Ala Lys Pro His His Phe Met His Tyr Ala Val Tyr
240                 245                 250 gac ttc atc gtc aag ggc agc tgc ttc tgc aac ggc cac gct gac cag          936
Asp Phe Ile Val Lys Gly Ser Cys Phe Cys Asn Gly His Ala Asp Gln
255                 260                 265                 270 tgc tta cct gtg gag ggc ttc aga ccc atc aag gcc ccg gga gcg ttc          984
Cys Leu Pro Val Glu Gly Phe Arg Pro Ile Lys Ala Pro Gly Ala Phe
                    275                 280                 285 cac gtg gtc cac ggg agg tgt atg tgt aag cac aac aca gca ggc agc         1032
His Val Val His Gly Arg Cys Met Cys Lys His Asn Thr Ala Gly Ser
                290                 295                 300 cac tgc cag cac tgt gca cca ttg tac aat gac cgg ccc tgg gag gca         1080
His Cys Gln His Cys Ala Pro Leu Tyr Asn Asp Arg Pro Trp Glu Ala
            305                 310                 315 gca gat ggc aga aca ggg gct cct aac gaa tgc aga act tgc aag tgc         1128
Ala Asp Gly Arg Thr Gly Ala Pro Asn Glu Cys Arg Thr Cys Lys Cys
320                 325                 330 aat ggg cac gcg gac acc tgt cac ttc gac gtc aac gtg tgg gag gcg         1176
Asn Gly His Ala Asp Thr Cys His Phe Asp Val Asn Val Trp Glu Ala
335                 340                 345                 350 tcg ggg aac cgc agc ggc ggt gtc tgc aac aac tgt cag cac aac act         1224
Ser Gly Asn Arg Ser Gly Gly Val Cys Asn Asn Cys Gln His Asn Thr
                    355                 360                 365 gag ggt cag cac tgt cag cgc tgt aag ccc ggt ttc tac cgc gac ctc         1272
Glu Gly Gln His Cys Gln Arg Cys Lys Pro Gly Phe Tyr Arg Asp Leu
                370                 375                 380 aga aga ccc ttc tcc gcc cct gac gct tgc aaa gcg tgt tcc tgc cac         1320
Arg Arg Pro Phe Ser Ala Pro Asp Ala Cys Lys Ala Cys Ser Cys His
            385                 390                 395 ccg gtt gga tca gcg atc ctt cct ttc agc tca gtg acc ttc tgc gac         1368
Pro Val Gly Ser Ala Ile Leu Pro Phe Ser Ser Val Thr Phe Cys Asp
400                 405                 410 ccc agc aat ggt gac tgc ccc tgc aag cct ggg gtg gcg ggg cca cat         1416
Pro Ser Asn Gly Asp Cys Pro Cys Lys Pro Gly Val Ala Gly Pro His
415                 420                 425                 430
```

| | | | | | | | | | | | | | | | |
|---|---|---|---|---|---|---|---|---|---|---|---|---|---|---|---|
| tgt | gac | aga | tgc | atg | gtg | gga | tac | tgg | ggt | ttt | gga | gac | tac | ggc | tgc | 1464 |
| Cys | Asp | Arg | Cys | Met | Val | Gly | Tyr | Trp | Gly | Phe | Gly | Asp | Tyr | Gly | Cys | |
| | | | 435 | | | | 440 | | | | | 445 | | | | |

```
tgt gac aga tgc atg gtg gga tac tgg ggt ttt gga gac tac ggc tgc     1464
Cys Asp Arg Cys Met Val Gly Tyr Trp Gly Phe Gly Asp Tyr Gly Cys
            435             440                 445 aga cct tgc gat tgt gcg ggg agc tgc gac ccg ctc acg gga gac tgc     1512
Arg Pro Cys Asp Cys Ala Gly Ser Cys Asp Pro Leu Thr Gly Asp Cys
            450             455                 460 atc agc agt aac gct gat gta gac tgg tac cac gaa gtc ccc acc ttt     1560
Ile Ser Ser Asn Ala Asp Val Asp Trp Tyr His Glu Val Pro Thr Phe
            465             470                 475 cac tcg atg cac aat aag agt gag ccc agc tgg gaa tgg gag gat gag     1608
His Ser Met His Asn Lys Ser Glu Pro Ser Trp Glu Trp Glu Asp Glu
            480             485                 490 caa gga ttt tct gcc ctc cga cac tca ggt aaa tgt gaa tgt aag gaa     1656
Gln Gly Phe Ser Ala Leu Arg His Ser Gly Lys Cys Glu Cys Lys Glu
495             500             505                 510 cag gtg tta gga aac ccc aaa gcc ttc tgt gga atg aag tat tca tat     1704
Gln Val Leu Gly Asn Pro Lys Ala Phe Cys Gly Met Lys Tyr Ser Tyr
                515             520                 525 gtg tta aaa atc aag atc tta tca gcc cat gac aaa ggc tcc cat gcc     1752
Val Leu Lys Ile Lys Ile Leu Ser Ala His Asp Lys Gly Ser His Ala
            530             535                 540 gaa gtc aat gtg aag att aag aaa gtc tta aag tcc acc aaa ctg aag     1800
Glu Val Asn Val Lys Ile Lys Lys Val Leu Lys Ser Thr Lys Leu Lys
            545             550                 555 atc tta cga ggc aag aga acg cta tac cca gag tcc tgg act aac aga     1848
Ile Leu Arg Gly Lys Arg Thr Leu Tyr Pro Glu Ser Trp Thr Asn Arg
            560             565                 570 ggc tgc acc tgt cca atc ctc aat cca gga ttg gag tac ctg gtc gcc     1896
Gly Cys Thr Cys Pro Ile Leu Asn Pro Gly Leu Glu Tyr Leu Val Ala
575             580             585                 590 ggc cac gag gac gta aga acg ggc aaa tta att gtg aat atg aaa agc     1944
Gly His Glu Asp Val Arg Thr Gly Lys Leu Ile Val Asn Met Lys Ser
                595             600                 605 ttt gtc cag cac tgg aaa cca gct ctt ggc aga aga gtc atg cac atc     1992
Phe Val Gln His Trp Lys Pro Ala Leu Gly Arg Arg Val Met His Ile
            610             615                 620 tta aaa aga gac tgc gtg tagcactgaa ggtcttaagc acacaagggc           2040
Leu Lys Arg Asp Cys Val
            625 ttttctac                                                            2048
```

<210> SEQ ID NO 5
<211> LENGTH: 628
<212> TYPE: PRT
<213> ORGANISM: Mus musculus

<400> SEQUENCE: 5

```
Met Gly Ser Cys Ala Arg Leu Leu Leu Trp Gly Cys Ser Ala Val
1               5                   10                  15

Ala Ala Gly Leu Asn Gly Val Ala Gly Ala Asn Ser Arg Cys Glu Lys
                20                  25                  30

Ala Cys Asn Pro Arg Met Gly Asn Leu Ala Leu Gly Arg Lys Leu Arg
            35                  40                  45

Ala Asp Thr Met Cys Gly Gln Asn Ala Thr Glu Leu Phe Cys Phe Tyr
        50                  55                  60

Ser Glu Asn Ala Asp Leu Thr Cys Arg Gln Pro Lys Cys Asp Lys Cys
65                  70                  75                  80

Asn Ala Ala His Ser His Leu Ala His Pro Pro Ser Ala Met Ala Asp
                85                  90                  95
```

```
Ser Ser Phe Arg Phe Pro Arg Thr Trp Trp Gln Ser Ala Glu Asp Val
            100                 105                 110

His Arg Glu Lys Ile Gln Leu Asp Leu Glu Ala Glu Phe Tyr Phe Thr
        115                 120                 125

His Leu Ile Met Val Phe Lys Ser Pro Arg Pro Ala Ala Met Val Leu
        130                 135                 140

Asp Arg Ser Gln Asp Phe Gly Lys Thr Trp Lys Pro Tyr Lys Tyr Phe
145                 150                 155                 160

Ala Thr Asn Cys Ser Ala Thr Phe Gly Leu Glu Asp Asp Val Val Lys
                165                 170                 175

Lys Gly Ala Ile Cys Thr Ser Arg Tyr Ser Asn Pro Phe Pro Cys Thr
                180                 185                 190

Gly Gly Glu Val Ile Phe Arg Ala Leu Ser Pro Pro Tyr Asp Ile Glu
                195                 200                 205

Asn Pro Tyr Ser Ala Lys Val Gln Glu Gln Leu Lys Ile Thr Asn Leu
        210                 215                 220

Arg Val Arg Leu Leu Lys Arg Gln Ser Cys Pro Cys Gln Ile Asn Asp
225                 230                 235                 240

Leu Asn Ala Lys Pro His His Phe Met His Tyr Ala Val Tyr Asp Phe
                245                 250                 255

Ile Val Lys Gly Ser Cys Phe Cys Asn Gly His Ala Asp Gln Cys Leu
                260                 265                 270

Pro Val Glu Gly Phe Arg Pro Ile Lys Ala Pro Gly Ala Phe His Val
                275                 280                 285

Val His Gly Arg Cys Met Cys Lys His Asn Thr Ala Gly Ser His Cys
        290                 295                 300

Gln His Cys Ala Pro Leu Tyr Asn Asp Arg Pro Trp Glu Ala Ala Asp
305                 310                 315                 320

Gly Arg Thr Gly Ala Pro Asn Glu Cys Arg Thr Cys Lys Cys Asn Gly
                325                 330                 335

His Ala Asp Thr Cys His Phe Asp Val Asn Val Trp Glu Ala Ser Gly
                340                 345                 350

Asn Arg Ser Gly Gly Val Cys Asn Asn Cys Gln His Asn Thr Glu Gly
        355                 360                 365

Gln His Cys Gln Arg Cys Lys Pro Gly Phe Tyr Arg Asp Leu Arg Arg
        370                 375                 380

Pro Phe Ser Ala Pro Asp Ala Cys Lys Ala Cys Ser Cys His Pro Val
385                 390                 395                 400

Gly Ser Ala Ile Leu Pro Phe Ser Ser Val Thr Phe Cys Asp Pro Ser
                405                 410                 415

Asn Gly Asp Cys Pro Cys Lys Pro Gly Val Ala Gly Pro His Cys Asp
                420                 425                 430

Arg Cys Met Val Gly Tyr Trp Gly Phe Gly Asp Tyr Gly Cys Arg Pro
                435                 440                 445

Cys Asp Cys Ala Gly Ser Cys Asp Pro Leu Thr Gly Asp Cys Ile Ser
        450                 455                 460

Ser Asn Ala Asp Val Asp Trp Tyr His Glu Val Pro Thr Phe His Ser
465                 470                 475                 480

Met His Asn Lys Ser Glu Pro Ser Trp Glu Trp Glu Asp Glu Gln Gly
                485                 490                 495

Phe Ser Ala Leu Arg His Ser Gly Lys Cys Glu Cys Lys Glu Gln Val
                500                 505                 510
```

```
Leu Gly Asn Pro Lys Ala Phe Cys Gly Met Lys Tyr Ser Tyr Val Leu
        515                 520                 525

Lys Ile Lys Ile Leu Ser Ala His Asp Lys Gly Ser His Ala Glu Val
530                 535                 540

Asn Val Lys Ile Lys Val Leu Lys Ser Thr Lys Leu Lys Ile Leu
545                 550                 555                 560

Arg Gly Lys Arg Thr Leu Tyr Pro Glu Ser Trp Thr Asn Arg Gly Cys
                565                 570                 575

Thr Cys Pro Ile Leu Asn Pro Gly Leu Glu Tyr Leu Val Ala Gly His
                580                 585                 590

Glu Asp Val Arg Thr Gly Lys Leu Ile Val Asn Met Lys Ser Phe Val
            595                 600                 605

Gln His Trp Lys Pro Ala Leu Gly Arg Arg Val Met His Ile Leu Lys
        610                 615                 620

Arg Asp Cys Val
625

<210> SEQ ID NO 6
<211> LENGTH: 23
<212> TYPE: DNA
<213> ORGANISM: Artificial Sequence
<220> FEATURE:
<223> OTHER INFORMATION: primer for PCR

<400> SEQUENCE: 6
ctgaaacgac agtcttgtcc ctg                                          23

<210> SEQ ID NO 7
<211> LENGTH: 23
<212> TYPE: DNA
<213> ORGANISM: Artificial Sequence
<220> FEATURE:
<223> OTHER INFORMATION: primer for PCR

<400> SEQUENCE: 7
taatgtctgt tccttacttc gca                                          23

<210> SEQ ID NO 8
<211> LENGTH: 24
<212> TYPE: DNA
<213> ORGANISM: Artificial Sequence
<220> FEATURE:
<223> OTHER INFORMATION: primer for PCR

<400> SEQUENCE: 8
cattgtcaag ggcagctgct tctg                                         24

<210> SEQ ID NO 9
<211> LENGTH: 23
<212> TYPE: DNA
<213> ORGANISM: Artificial Sequence
<220> FEATURE:
<223> OTHER INFORMATION: primer for PCR

<400> SEQUENCE: 9
gccaccccag gcttgcaagg gca                                          23

<210> SEQ ID NO 10
<211> LENGTH: 20
<212> TYPE: DNA
<213> ORGANISM: Artificial Sequence
<220> FEATURE:
<223> OTHER INFORMATION: primer for PCR
```

```
<400> SEQUENCE: 10
tgaaggtcgg tgtgaacgga                                                  20

<210> SEQ ID NO 11
<211> LENGTH: 20
<212> TYPE: DNA
<213> ORGANISM: Artificial Sequence
<220> FEATURE:
<223> OTHER INFORMATION: primer for PCR

<400> SEQUENCE: 11
gatggcatgg actgtggtca                                                  20

<210> SEQ ID NO 12
<211> LENGTH: 24
<212> TYPE: DNA
<213> ORGANISM: Artificial Sequence
<220> FEATURE:
<223> OTHER INFORMATION: primer for PCR

<400> SEQUENCE: 12
gtaagcccgg tttctaccgc gacc                                             24

<210> SEQ ID NO 13
<211> LENGTH: 24
<212> TYPE: DNA
<213> ORGANISM: Artificial Sequence
<220> FEATURE:
<223> OTHER INFORMATION: primer for PCR

<400> SEQUENCE: 13
cccttgtgtg cttaagacct tcag                                             24

<210> SEQ ID NO 14
<211> LENGTH: 5164
<212> TYPE: DNA
<213> ORGANISM: Mus musculus

<400> SEQUENCE: 14
tggtctgtag ctaggaaact cttgaaataa gaaacagcac cattggaaag aggcttagat      60
tcaagcttga ggaaattccc gaggtgatat tcctaagggc agccgaatgg cagaggcctg     120
gtaaaaacca gaatgggaga tgatttcagt gggaacactt tatccgacct tcttcacaca     180
aggttgtagc cacagaagac ggacaagcaa tgcaatcctg atctaggaac ccaggttctt     240
gagccaatga gctcatttgg atgtgtacat atttatgatc taagtttggt gatgatatcc     300 cctcccccccc gacactatct ctttgtacaa ttctttgtgg gttgcaatat gcacacattc     360
attcaagagg ggcaaaagag gtgatgtttc ttgttccttg aagaaagaat atcagatacc     420
atgataataa gtctctttcc aaagtccccc attctgttgg tgatatagaa taagtgtcac     480
ataaagtata ctggccttat tcaggaagca gatatatatt tttctattag gataataagc     540
ttgttttaaa tatcctgact tttttttatc ttttacctt tgtgtgtgtg tgtgtgtgtg     600
tgtgtgtgtg agagagagag agagagagag agagagagag agagagagag taggaacccc     660
agatcaccct ctccaccttc ctcagtgcta agcacggttt caacggtcag catcttcttg     720
gtaaaacacg ggttctgagg gtgaagccca ggccctcatt gcttcgaagg ctagcacctt     780
tttagacaga gctatctctc ccaactattt tttaatttag aaatgtgacc ctgaggatct     840
tttttttttt aaacttaata ctgtttgaat gtttcctata tgtattcaag cactaaatct     900
```

```
taacggcctg taagaaatca atacatacaa aaagtttatt ctgactccaa gctatgttag    960
ccagtgttac aaagctgcag gtgtgttctt aggctacgta agtacaagtc ctagactcaa   1020
ggacactgta agttttattt tatttttattc taattgatca cacttacagt tgacttatat   1080
gtgtactgtg caattggagt atatctgaaa agggatgaag aagagttttt caaagcactt   1140
ggagaaggtg cttaaataga gcaatcaaac ctgggttcaa cgtctcagag acctaacagg   1200
tggtccgtgc tttcatccca gcactcagaa gactaaggca agaaacacta agagtttggg   1260
gtcagcctgg gctacatcaa tagcaggttt caggccaggc caacctgggc tatttaatga   1320
gaccttgtct caactcttgc atgcacgcgc gcgcgcacac acacacacac atacattaaa   1380
gagagaactg gtatttatct gtatagctgc aaatgtctat aaagaggtag tgcacagtta   1440
aataaaacca gtgctgaaat cgagtgatgc ttttgattct tttgtttatt gggatgctca   1500
gaagaaaacc tgtgtgacca atggcagagt tttcacggtg aatgaagggc tccgggtagg   1560
gtgagagttg gggcccaggg tcccatctga ttctgaacat ctttcggtca ttagactttg   1620
tgctgggttt ttagagatct cttcagagct ttgtggtgct ttgtctctgt gctaacaggc   1680
cttgggctgc tggaagattt tttgctttga aggaggatgg atactgctgc catgttttg   1740
tctttacgtc tgctgtttcg ccatcctctt gcttctaggc tgccacagtt tatcccttct   1800
tctgagcagg atcctgttcc gcttgggctt gttctcctca tacactgagc cccagaaaag   1860
caccctgcac agtcacactg aaattggagg agaaacttaa atgtggccca gaggcgcttg   1920
ggaatgaggt cttggtgta tggacctta gcctttctga tgtagatata tattagcggt   1980
cctgtcaaca tccttccaag tcgtcaggaa tgttctacat taaatttgtg gatttgtggc   2040
tttggaaaac ctgctattga aatcctgcaa tttatccaac cctccctgta atccatgaca   2100
cctggaaagt tctgagtcag ttcttgacat tttcataaca cgaagacata atgagcaatg   2160
tccccacccg gaacacattt tcctcacatt ggccaactct cttgggtcct ttttcaaaa   2220
tgaaaatata atttgtaaga atgtatacta gatatgcact ttaaaaaaaa aaacttcttg   2280
cctctaccaa tgactaaggt tacaggcgga aaccaccaca ttgcgcccag acaacattta   2340
ttcgaatgct cattaccgtt tctctgagct agtccacact taaagtattg ctgtggagag   2400
cccacattcc tctagaatcc tgggaatcgt tcttatttcg ccgctttatt ctcagtctct   2460
attcttagca tataacaata gttttgagat aactgtcaaa acatttattg catgtctgac   2520
aagtgttttc agttaagaat aacgagcaat gtaagaaaaa aaacataatt gtgtcttgca   2580
tagtctaagt gtctagctgc catttaagga tcttgctgtt tattaaagga gcgacaaacc   2640
agttacaaag cgatcagggg agtacccagc aaatgcttct gaaattcata atcaggcatg   2700
gattagccct gcctcaactt aatatattgt ctcagagatt aatagtaaat actgtctttc   2760
tcttcctttt tcttggcctg taggctagtg tttaggctgg gagctttagc ctgttacgat   2820
cccctgtcgt tcatttaata aaagaacag agaagcattt tagcaactgc atcagaagca   2880
tcacctgtga gagccaaagg aggctccagc gtggccagta tttgaaagct cagagtttgt   2940
tttctaaagc tggtgacggt tctcatgtcg cctgccactt ccagtactgg ccaaaataat   3000
aattttaacg ccttcccagt ggattatgct aacctcaact cagttccttt agagagatag   3060
aaacctatat gtctccagct cggtcattat aaataatatc tacgtgtgcc cccaaagctc   3120
taattggccc catctgtatt tctgacaatt tataataact gaatggtatc tgcaaagcag   3180
ttaacttcct ggaaaatact caaagacaca cactgaatgc tgcaatacag aattgccttc   3240
gactcaacgt ttgccaattt ctttgcatgt gtaagcagaa ctatattttc agagaagtta   3300
```

| | |
|---|---:|
| cagaagtccc aggctgaagt gctatttaat ctcctttcat aaacaccagc cctgagctac | 3360 |
| aattagctgc ttgtggttgc tgctaaattg ctccccataa gatatttcat aactttatgg | 3420 |
| ttcccctgct caccatacta tgaagaatgt gtgaatgcac ctaggaccca ggcattctta | 3480 |
| tgtcgatgtt ccagactgag atgttcttaa acagttgatt ccctgatcat ggatcctggt | 3540 |
| ctttcaggcc gtgtgagaac atcttttaca ccaaaacggg tacaccttcg actcctttgg | 3600 |
| gctgcacccc ccaaaaaggt agcagagact taaaggacct tagcatttgg tgcgcgttca | 3660 |
| ctggcagtac cctaggcaga attggggggtc tgggggtggt cctaacccag accgtgggac | 3720 |
| tcacagagaa tgggtgctgt ggagtggtgt tgggggaggg gggaaggctt gttttgctgg | 3780 |
| gtgattttttg aaagtagtcg ctcgcctgtt tcgcgggttt ttaagcccct tggcatgccc | 3840 |
| tgaccctgat ccggagggag tcaactgctc tcaggaatgt tcctggagaa aggtgggaga | 3900 |
| ctgtttccca ggcgaggccc ttgggtgctg gagggcaccc gcgaggtcag gcagggagat | 3960 |
| gcgcgcagcg ggggctgcag acacccctc cccctgggcg gcggcggcgg cgacaatgac | 4020 |
| cggacccgcg cgtctgcacc acccggctgt caagcgcggg gggcgggcgg gaggaagggg | 4080 |
| tggaggtgcg aggggaggag gaggctggca ccggagcgcc gcggtgtcgg tgcaataaaa | 4140 |
| atgcatccca tggaactgcc catggagaag gacgggaccg agcctcggcg gccacagaag | 4200 |
| gtgggaaaag cggaggagga cagccgggag gcggcggcg ccgggaagtg aaaggtctcg | 4260 |
| caaagttcag cgtcggctgc gggcgccgag ccctgggcga gcggcgcacc cgccctcagg | 4320 |
| gccgctcagc cggcagcggc caggccggct atgatcccgg ggctcccgcc gctgctgagc | 4380 |
| tgccccgggc cccgccaggc cggtgcgcga cggtcacccc gccccctggc gcggccccgg | 4440 |
| cccgcggctc tgtgcccacg gtgcccactg agcgagcctg gcgctccggg aggaggaaga | 4500 |
| accacagagc ccccggtgct cccgaggacc actgccgctt catcccaccc gctcccgcag | 4560 |
| ctgcccggcc atggggagct gcgcacggct gctgctgctc tggggctgct ccgcggtggc | 4620 |
| cgcaggcttg aatggagtag ccggagcgaa ctcccgctgt gagaaggcat gcaaccctcg | 4680 |
| catgggaaac ttggctttgg gaagaaagct ccgggcagac actatgtgtg ccagaacgc | 4740 |
| caccgaactc ttctgcttct acagtgagaa tgctgacctc acttgccggc agcccaagtg | 4800 |
| tgataaatgc aacgctgccc attctcacct agctcaccca ccctctgcca tggcagactc | 4860 |
| atccttcagg tttccccgga catggtggca gtctgcagag gatgtgcaca gggaaaagat | 4920 |
| tcagctagac ctggaagcag aattctactt cactcaccta attatggtgt tcaagtctcc | 4980 |
| caggcctgca gccatggtgc tggaccggtc ccaggacttt gggaagacct ggaagcctta | 5040 |
| caagtacttt gcaacaaact gctcggctac ttttggcctg gaagatgatg ttgtcaagaa | 5100 |
| gggagctatt tgcacgtcta gatactcaaa tcctttcccg tgcaccggag agaggttat | 5160 |
| tttc | 5164 |

<210> SEQ ID NO 15
<211> LENGTH: 1882
<212> TYPE: DNA
<213> ORGANISM: Homo sapiens

<400> SEQUENCE: 15

| | |
|---|---:|
| atggggagct gcgcgcggct gctgctgctc tggggctgca cggtggtggc cgcaggactg | 60 |
| agtggagtag ctggagtgag ttcccgctgt gaaaaagcct gcaaccctcg gatgggaaat | 120 |
| ttggctttgg ggcgaaaact ctgggcagac accacctgcg gtcagaatgc taccgaactg | 180 |

-continued

```
tactgcttct acagtgagaa caaggatctg acttgtcggc agcccaaatg tgacaagtgc    240
aatgctgcct atcctcacct ggctcacctg ccatctgcca tggcagactc atccttccgg    300
tttcctcgca catggtggca gtctgcggag gatgtgcaca gagaaaagat ccagttagac    360
ctggaagctg aattctactt cactcaccta attgtgatgt tcaagtcccc caggccggct    420
gccatggtgc tggaccgctc ccaggacttt gggaaaacat ggaagcctta taagtacttt    480
gcgactaact gctccgctac atttggcctg gaagatgatg ttgtcaagaa gggcgctatt    540
tgtacttcta aatactccag tccttttcca tgcactggag gagaggttat tttcaaagct    600
ttgtcaccac cacacgatac agagaaccct tacagtgcca aagttcagga gcagctgaag    660
atcaccaacc ttcgcgtgca gctgctgaaa cgacagtctt gtccctgtca gagaaatgac    720
ctgaacgaag agcctcaaca tttacacac tatgcgatct atgatttcat tgtcaagggc    780
agctgcttct gcaatggcca cgccgatcaa tgcatacctg ttcatggctt cagacctgtc    840
aaggccccag gaacattcca catggtccat gggaagtgta tgtgtaagca caacacagca    900
ggcagccact gccagcactg tgccccgtta tacaatgacc ggccatggga ggcagctgat    960
ggcaaaacgg gggctcccaa cgagtgcaga gcctgcaagt gtaatgggca tgctgatacc   1020
tgtcacttcg acgttaatgt gtgggaggca tcagggaatc gtagtggtgg tgtctgtgat   1080
gactgtcagc acaacacaga aggacagtat tgccagaggt gcaagccagg cttctatcgt   1140
gacctgcgga gaccttctc agctccagat gcttgcaaac cgtgttcctg ccatccagta   1200
ggatcagctg tccttcctgc caactcagtg accttctgcg accccagcaa tggtgactgc   1260
ccttgcaagc ctggggtggc agggcgacgt tgtgacaggt gcatggtggg atactggggc   1320
ttcggagact atggctgtcg accatgtgac tgtgcgggga gctgtgaccc tatcaccgga   1380
gactgcatca gcagccacac agacatagac tggtgtcatg aagttcctga cttccgtccc   1440
gtgcacaata agagcgaacc agcctgggag tgggaggatg cgcaggggtt ttctgcactt   1500
ctacactcag gtaaatgcga atgtaaggaa cagacattag gaaatgccaa ggcattctgt   1560
ggaatgaaat attcatatgt gctaaaaata aagatttat cagctcatga taaaggtact   1620
catgttgagg tcaatgtgaa gattaaaaag gtcttaaaat ctaccaaact gaagattttc   1680
cgaggaaagc gaacattata tccagaatca tggacggaca gaggatgcac ttgtccaatc   1740
ctcaatcctg gtttggaata ccttgtagca ggacatgagg atataagaac aggcaaacta   1800
attgtgaata tgaaaagctt tgtccagcac tggaaacctt ctcttggaag aaaagtcatg   1860
gatattttaa aagagagtg ca                                              1882
```